United States Patent
Sauter

(10) Patent No.: US 12,383,793 B2
(45) Date of Patent: Aug. 12, 2025

(54) ASSEMBLY, SYSTEM AND METHOD FOR IMPROVED TRAINING

(71) Applicant: EGYM GMBH, Munich (DE)

(72) Inventor: Florian Sauter, Munich (DE)

(73) Assignee: EGYM GMBH, Munich (DE)

( * ) Notice: Subject to any disclaimer, the term of this patent is extended or adjusted under 35 U.S.C. 154(b) by 85 days.

(21) Appl. No.: 17/845,919

(22) Filed: Jun. 21, 2022

(65) Prior Publication Data

US 2022/0314071 A1 Oct. 6, 2022

Related U.S. Application Data

(63) Continuation of application No. 17/787,916, filed as application No. PCT/EP2020/086547 on Dec. 16, (Continued)

(30) Foreign Application Priority Data

Dec. 23, 2019 (EP) .................................... 19219461

(51) Int. Cl.
*A63B 24/00* (2006.01)
*G06T 7/20* (2017.01)
*G06V 10/82* (2022.01)

(52) U.S. Cl.
CPC ...... *A63B 24/0087* (2013.01); *A63B 24/0062* (2013.01); *G06T 7/20* (2013.01);
(Continued)

(58) Field of Classification Search
CPC ............ A63B 24/0087; A63B 24/0062; A63B 2024/0068; A63B 2024/0093;
(Continued)

(56) References Cited

U.S. PATENT DOCUMENTS 6,045,491 A * 4/2000 McNergney ....... A63B 22/0087
   482/121
8,287,434 B2 * 10/2012 Zavadsky .............. A63B 21/00
   482/901

(Continued)

FOREIGN PATENT DOCUMENTS

| CN | 102574004 A | 7/2012 |
| DE | 102016015109 B3 | 5/2018 |
| WO | 2009124752 A1 | 10/2009 |

OTHER PUBLICATIONS

WIPO, International Search Report (ISR) received in International Application No. PCT/EP2020/086547, Mar. 25, 2021, (4p.).

(Continued)

*Primary Examiner* — Garrett K Atkinson
(74) *Attorney, Agent, or Firm* — Siritzky Law, PLLC

(57) ABSTRACT

A training machine assembly comprises at least one control device and at least one training resistance. Each of the at least one training resistance comprises at least one training resistance value, such as a force applied towards the user contact element, e.g. a handle. The training resistance value can also comprise a function or a vector, for example a function linking a speed of movement of a user and/or a user contact element and a force applied against said movement. The control device can be a control device for controlling the training machine assembly. The training resistance can comprise an actuator. The actuator can comprise an electric motor. The training resistance can comprise a weight. The training resistance can comprise an element configured to provide a resistance against a movement of the user. The training machine assembly can comprise at least one camera.

19 Claims, 4 Drawing Sheets

Related U.S. Application Data 2020, now Pat. No. 12,109,457, application No. 17/845,919 is a continuation of application No. PCT/EP2020/086547, filed on Dec. 16, 2020.

(52) U.S. Cl.
CPC ...... *G06V 10/82* (2022.01); *A63B 2024/0068* (2013.01); *A63B 2024/0093* (2013.01); *A63B 2220/05* (2013.01); *A63B 2220/807* (2013.01); *A63B 2225/09* (2013.01); *A63B 2230/062* (2013.01); *A63B 2230/625* (2013.01); *G06T 2207/30196* (2013.01); *G06T 2207/30241* (2013.01)

(58) Field of Classification Search
CPC .......... A63B 2220/05; A63B 2220/807; A63B 2225/09; A63B 2230/062; A63B 2230/625; A63B 23/0244; A63B 21/00; A63B 21/4029; A63B 23/0405; A63B 2220/806; G06T 7/20; G06T 2207/30196; G06T 2207/30241; G06V 10/82; A61B 2503/10; A61B 5/0245; A61B 5/1116; G06F 18/24137
See application file for complete search history.

(56) References Cited

U.S. PATENT DOCUMENTS

| | | | | |
|---|---|---|---|---|
| 9,586,089 | B2 * | 3/2017 | Lagree | A63B 22/203 |
| 9,622,686 | B1 * | 4/2017 | Berme | A63B 69/0053 |
| 10,150,003 | B2 * | 12/2018 | Lagree | A63B 24/0087 |
| 10,716,969 | B2 * | 7/2020 | Hoang | A63B 21/0058 |
| 11,117,019 | B1 * | 9/2021 | Lagree | A63B 23/0405 |
| 11,517,792 | B2 * | 12/2022 | Lagree | A63B 23/03508 |
| 11,638,857 | B2 * | 5/2023 | Lagree | A63B 24/0062 482/130 |
| 2007/0202992 | A1 * | 8/2007 | Grasshoff | A63B 24/00 482/8 |
| 2008/0176713 | A1 * | 7/2008 | Olivera Brizzio | A63B 24/00 482/8 |
| 2010/0267524 | A1 * | 10/2010 | Stewart | A63B 22/0015 482/52 |
| 2011/0152045 | A1 * | 6/2011 | Horne | A63B 21/0628 482/131 |
| 2011/0237400 | A1 * | 9/2011 | King | A63B 21/4017 482/8 |
| 2013/0210578 | A1 * | 8/2013 | Birrell | A63B 22/0017 482/4 |
| 2014/0066257 | A1 * | 3/2014 | Shavit | A63B 23/03541 482/5 |
| 2015/0360083 | A1 * | 12/2015 | Lagree | A63B 23/0405 482/130 |
| 2017/0361165 | A1 * | 12/2017 | Miller | A63B 21/00178 |
| 2019/0015701 | A1 * | 1/2019 | Changchien | A63B 24/0062 |
| 2019/0118066 | A1 * | 4/2019 | Cardona | A63B 24/0062 |
| 2019/0126099 | A1 | 5/2019 | Hoang | |
| 2021/0402281 | A1 * | 12/2021 | McCready | A63B 24/0087 |

OTHER PUBLICATIONS

WIPO, International Written Opinion (WO) received in International Application No. PCT/EP2020/086547, Mar. 25, 2021, (5p.).
WIPO, International Preliminary Report received in International Application No. PCT/EP2020/086547, Jun. 28, 2022, (6p.).
EPO, European Search Report received in European Application No. 20829906.5, May 27, 2024, (6p.).

* cited by examiner

ASSEMBLY, SYSTEM AND METHOD FOR IMPROVED TRAINING

RELATED APPLICATIONS

This application is a continuation of application Ser. No. 17/787,916, filed Jun. 21, 2022, which is the National Phase in the U.S.A. (a 371) of International Application No. PCT/EP2020/086547, filed Dec. 16, 2020, the entire contents of each of which are hereby fully incorporated herein by reference for all purposes. PCT/EP2020/086547 claims the priority benefit of European patent application EP 19219461.1, filed Dec. 23, 2019, the entire contents of which are hereby fully incorporated herein by reference for all purposes. This application is a continuation of PCT/EP2020/086547.

Field of Invention

The invention relates to machines for training and exercising. The invention further relates to an operation of such machines based sensor data and to a system of such training machines.

The invention can further relate to a control of training machine assemblies in a circuit training setup.

Technical Background

U.S. Pat. No. 8,287,434B2 discloses facilitating a strength training exercise by a video gaming system (VGS). VGS communicates information about the exercise resistance force with an exercise device. Strength training machine coupled with the VGS and acts as a game controller. The machine provides resistance by an electrical motor. Resistance can be adjusted using data send from the VGS. Further, the resistance can pulsate during an exercise motion, providing internal muscle massage. The video gaming system uses a non-contact method to monitor a physiological parameter of the user. For example, a video camera is used to detect heart rate. Pose tracking information is used to detect the level of user exhaustion. Those and other monitored parameters are used to adjust the regime for either current or future exercises. The regime is optimized to increase workout efficiency. An activity not directly related to exercise, for example game, is unlocked if exercise performance is on track.

WO2009124752A1 discloses a system (10) for promoting fitness and for the medical rehabilitation of a person undergoing training, and to a method for operating said system. The system (10) comprises at least one training device (80) having at least one actuator which is equipped to pre-adjust the training device (80) automatically for the person undergoing training, and a device, preferably a body scanner (50), for the automated capture of physical dimensions and/or body geometry data of the person undergoing training. The at least one training device (80) is pre-adjusted for the person undergoing training based on the automatically captured physical dimensions and/or body geometry data of the person undergoing training. The training device (80) and the device for capturing physical dimensions and/or body geometry data is preferably integrated into a local network together with a server (20). The server (20) determines the pre-adjustments for the training device based on the physical dimensions and/or body geometry data of the person undergoing training and controls the training device accordingly. Alternatively, the physical dimensions and the body geometry data can be stored during capture on a data carrier, preferably a chip card, of the person undergoing training. Said chip card can be carried by the measured person undergoing training and can be inserted in a corresponding data carrier reader on the training device, the training device being then adjusted to the pre-adjusted values contained on the data carrier.

DE102016015109B3 discloses a resistance source (102, 202) for applying a training resistance force (F) along a training path (104, 204) of a strength training device (100, 200), comprising a control unit (122, 222) by means of which the resistance to be applied can be adjusted during training is, characterized in that the control unit is adapted, at a reversal point (x) or another risk point (x, $\alpha$, $\alpha$) of the training track to limit the force applied by the resistance source force to a predetermined maximum.

OBJECT OF THE INVENTION

It is an objective of the invention to provide an improved training machine assembly.

Furthermore, it is an objective of the invention to provide an improved system of training machine assemblies.

It is another objective of the present invention to provide an improved method for using at least one of said training machine assemblies.

It is an optional objective of the present invention to provide a system of training machine assemblies and a corresponding method for improved use of sensor data relating to at least one user.

It is another optional objective of the present invention to provide a system and method for adapting a training a performance and/or individual physiological features of the at least one user.

SUMMARY

In a first embodiment, a training machine assembly is disclosed.

The training machine assembly comprises at least one control device and at least one training resistance. Each of the at least one training resistance comprises at least one training resistance value, such as a force applied towards the user contact element, e.g. a handle. The training resistance value can also comprise a function or a vector, for example a function linking a speed of movement of a user and/or a user contact element and a force applied against said movement. The control device can be a control device for controlling the training machine assembly.

The training resistance can comprise an actuator. The actuator can comprise an electric motor.

The training resistance can comprise a weight.

The training resistance can comprise another element configured to provide a resistance against a movement of the user.

The training machine assembly can comprise at least one camera.

The at least one training resistance can be automatically adjustable. That is, its at least one training resistance value may be automatically adjustable. In other words, the at least one training resistance can be configured to be adjusted automatically. The training machine assembly can be configured to adjust the at least one training resistance.

That is, the training machine assembly can be configured for automatically adjusting the training resistance.

In case that the training resistance comprises the actuator, the machine can comprise a component configured for controlling the actuator.

At least one of the at least one control device can be configured for controlling the actuator. Th control device can comprise a data processing-unit configured.

The training machine assembly can further comprise a sensing unit configured to sense the training resistance value and/or an indicator thereof.

Such an indicator can for example be a power provided to or by the actuator, e.g. an electric current flowing by an electric motor, wherein the actuator comprises the electric motor.

Such an indicator can also be a torque measuring device and/or a force measuring device.

Such an indicator can also be a sensing unit configured to sense a configuration of the training resistance, e.g. of a locking mechanism of the training resistance when the training resistance comprises weights and pins for locking the weights in order to choose a defined weight.

The training machine assembly can comprise at least one automatically adjustable user support element. The user support element can for example be a seat and/or a back rest. The adjustable element of the training machine assembly can also be an element that is in contact with the user but that is not moved by the user during an exercise.

The training machine assembly can comprise a heart-rate detection component. The heart-rate detection component can be a component that is configured to detect a heart-rate of the user. The heart-rate detection component can also be a component that is configured to sense the heart-rate of the user. The heart-rate detection component can be a portion of a handle of the training machine assembly or such a handle. The heart-rate detection component can also be said handle or said portion of said handle, further comprising an appropriate sensor.

The heart-rate detection component can be configured to sense the heart-rate of the user when the user touches said heart-rate detection component.

The heart-rate detection component can also be configured for contact-less sensing.

The training machine assembly can be configured to be connected to a heart-rate sensing device. The heart-rate sensing device can be configured to sense the heart-rate of the user.

The connection can be wired.

The connection can also be wireless. An optional advantage can be a higher flexibility, an easier connection and/or less constraints while wearing the heart-rate sensing device.

The heart-rate sensing device can be configured sense the heart-rate of the user when in physical contact to the user. For example, the heart-rate sensing device can be configured to sense the heart-rate of the user when the user touches the heart-rate sensing device.

The heart-rate sensing device can portable. The heart-rate sensing device can be configured to be worn by the user.

The heart-rate sensing device can be at least one of a smart watch, a bracelet and another wearable fitness tracker device configured for sensing the heart-rate of the user. Another wearable fitness tracker device can for example be a ring configured for heart-rate sensing, that is a ring comprising at least one corresponding sensing unit that is configured for sensing the heart-rate of the user.

The heart-rate detection component can be mounted to the training machine assembly. The heart-rate detection component can also be a portion of the machine.

The heart-rate detection component can be configured to be touched by the user.

The heart-rate detection component can be configured to for sensing the heart-rate of the user.

The heart-rate detection component can be configured to for sensing a heart-rate variability of the user. The heart-rate variability can be a variability of a length of a time interval between single heart-beats of the user. It can be measured by a variation in the length of the time intervals between the heart-beats of the user. The heart-rate variability can also be referred to as "cycle length variability".

The training machine assembly can be configured for generating heart-rate data of the user. The heart-rate data can comprise data relating to a pulse of the user. The heart-rate data can be stored as a frequency of heart-beats. The heart-rate data can be stored as time intervals between heart-beats or parts thereof, such as a length of an R-R interval. However, the heart-rate data may also be stored differently.

The training machine assembly can be configured for generating the heart-rate data of the user by means of the heart-rate detection component.

The training machine assembly can be configured for generating the of a user based on image data captured by the at least one camera. That is, the training machine assembly can be configured for processing the image data of the at least one camera so as to extrapolate, sense and/or estimate the heart-rate of the user and generate corresponding heart-rate data.

Methods for estimating the heart-rate of a person based on image data are generally known to the person skilled in the art. Examples are discussed in Wang C., Pun T. & Chanel G. (2018): "A comparative Survey of Methods for Remote Heart Rate Detection From Frontal Face Videos", in *Frontiers of Bioengineering and Biotechnology*, 6:33, doi: 10.3389/fbioe.2018.00033

The training machine assembly can be configured for generating the heart-rate data of the user based on the image data, wherein the image data can comprise a sequence of images.

In other words, the image data can comprise data relating to a plurality of images that relate to different times. A video can be an example for such a sequence.

The training machine assembly can be configured for generating the heart-rate data of the user based on the image data. The image data can comprise a timestamped sequence of images.

That is, in the sequence of images, each image can comprise a timestamp.

However, also only one or only some images can comprise a timestamp, as long as timestamps corresponding to other images of the sequence can be determined.

The training machine assembly can be configured for generating the heart-rate data of the user based on video data captured by the camera.

The video data can comprise a data representation of a sequence of images, particularly a sequence of images with a constant sampling rate. In other words, the video data can comprise a data representation of a sequence of images, wherein the images relate to equidistant points in time.

The image data can be captured with a frequency of at least 6.67 Hz. In other words, at least 396 images per minute can be taken, stored and/or generated.

This can be optionally advantageous, as heart-rates up to 200 BPM (beats per minute) can be inferred at such a sampling frequency, which correspond to a frequency of 3.34 Hz and require a sampling frequency of at least 6.67 Hz according to the Nyquist-Shannon sampling theorem. Heart-rates above 200 BPM are rare in humans.

The image data can be captured with a frequency of at least 7.4 Hz. In other words, at least 444 images per minute can be captured.

This can be optionally advantageous, as heart rates up to 222 BPM can be captured as discussed above. Heart-rates above 220 BPM are very rare even in young and healthy users who can typically have the highest heart-rates.

The training machine assembly can be configured for generating skeleton data of the user based on the image data captured by the at least one camera.

The skeleton data can comprise data relating to joint positions, distances of joints and/or other anatomical features of the user, such as a length of body parts, asymmetries, injuries limiting the user's movements, such as a broken leg, a broken arm, and/or consequences of injuries.

Generating the skeleton data can for example comprise fitting a model of a human to the image data.

The training machine assembly can be configured for generating skeleton-trajectory data of the user based on image data captured by the at least one camera.

The skeleton-trajectory data can comprise data relating to a position over time of joints or other parts of a body of the user. In other words, the skeleton-trajectory data can relate to a trajectory of parts, portions and/or features of the body of the user.

Methods for determining and/or estimating skeleton data as well as skeleton-trajectory data of the user from image data are known to the person skilled in the art. Examples are discussed inter alia in Wandt B., Ackermann H. & Rosenhahn B.: "3D Reconstruction of Human Motion from Monocular Image Sequences", available at http://www.tnt.uni-hannover.de/papers/data/1168/pami final.pdf, retrieved at 22 Nov. 2019

Alldieck T., Kassubeck M. & Magnor M. (2017): "Optical Flow-based 3D Human Motion Estimation from Monocular Video", available at https://arxiv.org/pdf/1703.00177.pdf, retrieved at 22 Nov. 2019

Yasin H., Kruger B. & Weber, A. (2013): "Model based Full Body Human Motion Reconstruction from Video Data", available at https://cg.cs.uni-bonn.de/aigaion2root/attachments/yasin2013a.pdf, retrieved at 22 Nov. 2019

An example is further provided at https://github.com/derzu/BodySkeletonTracker, retrieved at 22 Nov. 2019.

The training machine assembly can be configured for generating the heart-rate data, the skeleton data and/or the generating the skeleton-trajectory data and using at least one or a plurality of boundary condition(s) corresponding to a geometry of the training machine assembly.

That is, the training machine assembly can be configured for generating the heart-rate data using the boundary condition(s) corresponding to the geometry of the training machine assembly.

The training machine assembly can also be configured for generating the skeleton data using the boundary condition(s) corresponding to the geometry of the training machine assembly.

The training machine assembly can also be configured for generating the skeleton-trajectory data using the boundary condition(s) corresponding to the geometry of the training machine assembly.

The boundary condition(s) can comprise at least one condition that limits a quantity of data and/or results that are corresponding to an input.

The boundary condition(s) can comprise at least one limitation regarding the image data.

For example, regarding generating the heart-rate data, the boundary condition(s) can comprise an indication of a section of an image input in which a patch of skin of the user, such as the user's forehead or neck, can be expected. Said section can be corresponding to the geometry of the training machine assembly. For example, when the training machine assembly is configured for having the user is sitting on it while exercising, his/her head can have a certain position relative to the machine.

As another example, a contact element of the training machine assembly can limit a position where a corresponding part of the body of the user is located while the user is exercising. An example for such a contact element can be the handle that the training machine assembly. A corresponding boundary condition can limit possible positions of a hand of the user and/or provide a corresponding initial pose and/or position for a determining operation.

An optional advantage of using the boundary conditions can be a reduced computing time in comparison to not using said boundary conditions.

Another optional advantage of using the boundary conditions can further be a reduction of errors in results.

An optional advantage of using the boundary conditions corresponding to the geometry of the training machine assembly can furthermore be that the geometry of the training machine assembly is known and/or can be sensed reliably. An example for the sensing can be sensing a relative position of a movable part of the training machine assembly, for example an angle of rotation of a rotatable part such as a handle bar mounted to the machine and which can be rotated by the user during exercising.

An optional advantage can be that the image data can have a lower quality at a given error rate than would be necessary to obtain a comparable or same error rate without the boundary condition(s).

An optional advantage can be that from a (2D-) image, which image may be typically ambiguous regarding a third dimension, information regarding said third dimension (or "depth") can be extracted by certain boundary conditions, for example by knowledge of trajectories which comprise a projection to the 2D image that is bijective. In other words, an optional advantage can be that 3D-data can be generated based on a 2D-image based on certain the boundary conditions, such as a trajectory of the handle of the training machine assembly.

At least one of the boundary condition(s) can be at least one possible position of at least one part of the body of the user.

An example can be a possible pose, a set of possible poses and/or at least one possible component of the possible pose or set of possible poses respectively.

The pose can be a pose of the hand of the user in a case where the training machine assembly comprises a handle.

The pose can also be a pose of a hip of the user in a case where the training machine assembly comprises a seat and/or another element that is in contact with the hip of the user.

The pose can also be a pose of another part or portion of the body of the user.

At least one of the boundary condition(s) can be at least one or a plurality of possible trajectories of movable parts of the training machine assembly.

The movable parts can comprise parts that can be moved during use of the training machine assembly, such as handles and weights. The movable parts can also comprise parts and/or portions that can be moved before and/or after use of the training machine assembly, for example to adjust the training machine assembly to the user. An example can be a movable seat or the like.

Possible trajectories are intended to refer to possible without damaging, "tricking" and/or improperly using the training machine assembly.

At least one of the boundary condition(s) can be at least one or a plurality of possible trajectories of at least parts of the body of the user interacting with the training machine assembly.

Such parts of the body of the user can for example be the hand of the user, the hip of the user or the other part of the body as discussed above.

The training machine assembly can comprise a supplementary sensing unit.

Said supplementary sensing unit can be a sensing unit for sensing an effort, a force and/or a torque. Said supplementary sensing unit can be a sensing unit for sensing an effort of the user during exercising.

Said supplementary sensing unit can also be configured for sensing a weight of a user.

Said supplementary sensing unit can also be configured for sensing an ambient temperature.

Said supplementary sensing unit can also be configured for sensing another variable.

Each of the at least one training resistance can be configured for sensing a training effort of the user.

The training effort of the user can be the effort of the user during exercising. The training effort of the user can be a force and/or a torque that the user applies during the exercise and/or a portion thereof. The training effort of the user can also be the force and/or the torque that the user applies during the exercise at a pre-defined point of time or space, for example at a beginning, a centre and/or an end of a movement.

Each of the at least one training resistance can comprise a sensing unit that is configured for sensing the user's training effort.

The training machine assembly may comprise not more than one camera. That is, in some embodiments, the training machine may only comprise one camera, but not more than one camera. In other words, the training machine assembly may comprise exactly one camera.

The at least one camera can be at least one 2D-camera. That is, the camera can be a camera configured for sensing light intensities and generate a 2D-representation of the sensed light intensities, such as a 2D image.

Light is intended to refer to electro-magnetic radiation, such as light in a visible spectrum, but also infrared radiation, radio waves and/or ultraviolet light.

An optional advantage of using the at least one 2D-camera may be that the training machine assembly can be easier, require fewer complex parts (such as a 3D-camera), parts that are less complex and/or be more cost-efficient.

The at least one camera can be at least one 3D-camera. That is, the at least one camera can be at least one camera configured to sense 3D-data.

The 3D-camera can be a compound comprising at least two 2D-cameras or at least one 2D-camera and at least one sender. The 3D-camera can further comprise an adapted processing unit which processing unit is configured for generating 3D-data from data sensed by the 3D-camera.

The at least one camera can be a set of at least one 2D-camera and at least one 3D-camera.

The at least one 2D-camera and the at least one 3D-camera can be configured to sense radiation of different wavelengths. For example, the 2D-camera can be configured to sense infrared radiation, and the 3D-camera can be configured to sense light in the visible spectrum.

At least one of the at least one 2D-camera can be configured for sensing light in the visible spectrum. An example can be an RGB-camera.

An optional advantage of the 2D-camera being configured for sensing light in the visible spectrum can be that the pulse of the user can be sensed or at least estimated by sensing a change of colour of a skin of the user.

An optional advantage of the RGB-camera can be that is can be easier to identify a red component of light reflected from the skin of the user, which may be further advantageous to detect a blood flow and hence the pulse of the user.

At least one of the at least one 3D-camera can comprise a projected infrared depth camera.

The at least one 3D-camera can also be projected infrared depth camera.

An optional advantage of a projected infrared depth camera can be a reliable but however cost-efficient and technically simple sensing of 3D-data.

The at least one of the at least one 3D-camera can comprise a time-of-flight depth camera.

The training machine assembly can be configured for combining data of the at least one camera. That is, the training machine assembly can be configured for processing data from the at least one camera.

This can be optionally advantageous in cases where the at least one camera is a plurality of cameras.

The training machine assembly can be configured for combining data of the at least one 2D-camera and the at least one 3D-camera. That is, the training machine assembly can be configured for generating data based on the data of the at least one 2D-camera and the at least one 3D-camera.

The training machine assembly can comprise a user interface.

The user interface can be configured for outputting data. The user interface can be any device configured for outputting data. It can comprise at least one of a screen, a speaker and/or a visual indicator.

The training machine assembly can be configured for storing the heart-rate data of the user. The training machine assembly can also be configured for transmitting the heart-rate data of the user. That is, the training machine assembly can be configured for sending the heart-rate data of the user.

The training machine assembly can for example be configured for sending the heart-rate data of the user to a third system.

The training machine assembly can be configured for comparing the heart-rate data of the user to predetermined heart-rate data.

The predetermined heart-rate data can be predetermined at least by prior measurements of the heart-rate.

The predetermined heart-rate data can be predetermined at least based on data.

The predetermined heart-rate data can be predetermined at least based on further measurements, such as the weight of the user.

The predetermined heart-rate data can further be predetermined at least based on demographic data, such as an age of the user.

The predetermined heart-rate data can comprise a maximum heart rate for the user.

The predetermined heart-rate data can comprise a resting pule for the user.

The training machine assembly can be configured for comparing the heart-rate data of the user to at least one of the at least one training resistance value.

In other words, the training machine assembly can be configured for comparing the heart-rate data, such as the pulse, of the user to the training resistance value.

This can be optionally advantageous, as the comparison can yield information on which training resistance is too high, right or too low for the user according to his/her heart-rate.

The training machine assembly can be configured for comparing the heart-rate data of the user corresponding to different activity levels of the user.

An activity level of the user can be a level of physical activity, such as a resting state in which the user is in which the user is resting and an exercising state in which the user is exercising.

An optional advantage can be that a difference between the pulse of the user in the resting state and in the exercising state can be a measure for an overall fitness of the user.

The training machine assembly can be configured for generating heart-rate comparison data.

The training machine assembly can be configured for generating heart-rate comparison data at least by comparing the heart-rate data of the user to the predetermined heart-rate data.

For example, in a case where the predetermined heart-rate data comprise the maximum heart-rate, the training machine assembly can be configured for comparing the heart-rate data of the user to said maximum heart-rate.

The training machine assembly can be configured for generating heart-rate comparison data at least by comparing the heart-rate data of the user corresponding to different activity levels of the user. That is, the training machine assembly can be configured for example for comparing a heart-rate of the user in the resting state, i.e. the resting pulse rate, to a heart-rate in an exercising state.

The training machine assembly can be configured for generating heart-rate comparison data at least by comparing the heart-rate data of the user to at least one of the at least one training resistance value.

An optional advantage can be that the heart rate of the user as well as a difference between the heart rate under different conditions can be indicators for a fitness level and/or a performance level of the user and that said comparison data can hence be an indicator of said fitness level and/or performance level.

The training machine assembly can be configured for generating the heart-rate comparison data by determining the heart-rate variability.

The heart-rate variability can be a measure for a general fitness of the user. The heart-rate variability can also be a measure for a fitness of the user on a training day.

Hence, an optional advantage of determining the heart-rate variability and/or of generating the heart-rate comparison data by determining the heart-rate variability can be that thus, a measure for the fitness of the user can be provided.

The training machine assembly can be configured for determining the heart-rate variability based on the heart-rate data.

The heart-rate comparison data can comprise heart-rate variability data. The heart-rate variability data can comprise data relating to the heart-rate variability of the user. The heart-rate variability data can comprise a measure for the heart-rate variability.

The training machine assembly can be configured for comparing the skeleton data to skeleton-reference data and to thus generating skeleton-comparison data.

The skeleton-reference data can comprise reference data regarding to the skeleton data, e.g. standard sizes, standard proportions and/or the like.

An optional advantage of generating the skeleton-comparison data can be that the skeleton-comparison data can be an indicator for anomalies in a physiology of the user.

Another optional advantage of generating said skeleton-comparison data can be that said skeleton-comparison data can be an indicator for a potential improvement of a training of the user by an adjustment of the training machine assembly.

An example can be a potential improvement by an adjustment of the automatically adjustable user support element based on the skeleton-comparison data, e.g. an adjustment of the contact element of the training machine assembly.

Another example can be a potential improvement by an adjustment of the automatically adjustable training resistance.

The training machine assembly can be configured for comparing the skeleton-trajectory data to skeleton-reference data and to thus generating trajectory-comparison data.

An optional advantage of generating the trajectory-comparison data can be that these data can be a measure for a proper execution of the exercise by the user. These data can also be measure for a potential improvement of the training of the user, for example by an adjustment of the training machine assembly.

An example can be a potential improvement by an adjustment of the automatically adjustable user support element based on the trajectory-comparison data, e.g. an adjustment of the contact element of the training machine assembly.

Another example can be a potential improvement by an adjustment of the automatically adjustable training resistance. For example, when the user starts exercising improperly, the resistance can be reduced to avoid injuries.

Comparing the skeleton-trajectory data to the skeleton-reference data can comprise adapting the skeleton-reference data. The training machine assembly can be configured for adapting the skeleton-reference data.

The adapted skeleton-reference data can be stored. They can be stored with data relating to the user. They can also be deleted and/or not stored permanently.

The skeleton-reference data can be generated for example based on skeleton-trajectory data of users who are exercising properly, such as instructors who use the training machine assembly. The skeleton-reference data can also be generated from a simulation of a user correctly exercising, for example a kinematics model.

The skeleton-reference data can be adapted when they are compared with the skeleton-trajectory data.

The skeleton-reference data, more particularly a portion referring to the trajectory-data, can be adapted based on the skeleton-data and/or the skeleton-comparison data.

This can be optionally advantageous, as it allows to compensate for differences between users, and more particularly between the user(s) whose data was used to generate the skeleton-reference data referring to the skeleton-trajectory data or to the simulation parameters used for the simulation.

The training machine assembly can be configured to transmit the heart-rate comparison data.

The training machine assembly can be configured to transmit the skeleton-comparison data.

The training machine assembly can be configured to transmit the trajectory-comparison data.

An optional advantage of transmitting at least one of said data can be that a second entity, such as other devices, assemblies and/or systems, can process said data.

An optional advantage of transmitting the heart-rate comparison data can be that the second entity can adapt a training resistance based on the current heart-rate comparison data and/or that said second entity can instruct and/or recommend the user to adapt a training resistance and/or a training intensity accordingly. The latter can for example be the case if the user uses the training machine assembly, performs other exercises afterwards and the second entity is for example a smart phone with a corresponding application installed.

An optional advantage of transmitting the skeleton-comparison data can be that the second entity can adjust a user support element based on the skeleton-comparison data. The second entity can also generate instruction data and/or recommendation data for such an adjustment.

An optional advantage of transmitting the trajectory-comparison data can be that the second entity can process a proper execution of the exercise that the user performed at the training machine assembly. The second entity can for example store data relating to proper executions of the exercise over time. The second entity can also output data to the user and/or another person, such as an instructor, based on the proper execution of the exercise.

The training machine assembly can be configured to transmit said data to a data-processing system.

Optional advantages can be according to the above-mentioned advantages. Another optional advantage can be that operations in order to process said data can be performed by an adapted data-processing system and do not need to be performed by the training machine assembly. A further optional advantage can be that said data can be available for a plurality of user exercises.

The training machine assembly can be configured to transmit said data to an end user computer device.

Optional advantages can be according to the above-mentioned optional advantages.

The end user computer device can be portable.

The training machine assembly can be configured to transmit said data to a server system.

The server system can comprise a server. The server system can also comprise a plurality of servers. The server system can comprise a cloud computing system and/or a portion thereof. The server system can also be a customised data-processing system configured to process data for a plurality of training machine assemblies and/or a plurality of end user computer devices.

The training machine assembly can be configured to transmit said data to at least one or a plurality of further training machine assemblies.

The training machine assembly can be configured to receive at least one of the heart-rate comparison data, the skeleton-comparison data and the trajectory-comparison data.

The respective advantages of sending said data to other training machines can optionally apply.

The training machine assembly can be configured to receive said data from the data-processing system.

The training machine assembly can be configured to receive said data from the at least one or a plurality of further training machine assemblies.

The training machine assembly can be configured for adjusting at least one of the at least one automatically adjustable user support element based on at least one of the skeleton-comparison data and the trajectory-comparison data.

This can be optionally advantageous to adapt the machine according to physiological measures of the user and to hence render the exercising more effective. Said physiological measures can for example be indicated by the skeleton-comparison data.

This can further be optionally advantageous to avoid improper or unhealthy exercising by the user and to support proper exercising. The improper or unhealthy exercising can for example be indicated by the trajectory comparison data.

The training machine assembly can be configured for adjusting at least one of the at least one training resistance based on at least one of the skeleton-comparison data and the trajectory-comparison data.

For example, in case of a user exercising improperly, which the trajectory-comparison data can indicate, the training resistance can be reduced.

In another example, the training resistance can be adapted based on the skeleton-comparison data, if the latter indicate an injury of the user.

An optional advantage of adjusting at least one training resistance based on at least one of the skeleton comparison data and the trajectory comparison data can be that injuries or adverse effects can be avoided and a proper exercising can be supported.

The training machine assembly can be configured for outputting data via the user interface based on at least one of the skeleton-comparison data and the trajectory-comparison data.

The training machine assembly can be configured for outputting data via the user interface based on the heart-rate comparison data.

The training machine assembly can be configured for receiving user plan data.

The training machine assembly can be configured for adjusting the training resistance based on the user plan data.

The user plan data can comprise an indication of exercises to perform. The user plan data can comprise an indication of an order of exercises. The user plan data can comprise an indication regarding the heart-rate data.

For example, the user plan data can comprise an indication of the training resistance value. The user plan data can also comprise an indication of different training resistance values for different exercises.

The user plan data can further comprise conditions, such as conditions relating to at least one of the heart-rate data of the user, the skeleton-trajectory and the trajectory-comparison data of the user.

The training machine assembly can be a strength training machine assembly.

The strength training machine assembly can for example comprise a contact element, via which the user can interact with the machine, e.g. a handle, a grip or the like. The contact element can be for example be configured to be touched, grabbed and/or pushed by the user. For example, the user can interact with the contact element by his arms, feet and/or other portions of his/her body.

The strength training machine assembly can for example further comprise the training resistance. The training resistance can for example comprise at least one of a weight stack, a motor, a spring, a hydraulic cylinder and a pneumatic cylinder.

The strength training machine assembly can further comprise an element connecting said contact element and the training resistance.

Further, the strength training machine assembly can further comprise a frame to which at least two of the training resistance, the connecting element and the contact element can be connected.

The training machine assembly can be configured for user identification. That is, the training machine assembly can be configured for identifying a user.

The training machine assembly can comprise a user identification device. The user identification device can comprise a camera. The user identification device can comprise a microphone. The user identification device can comprise a device for wireless communication configured for receiving data from a user device, such as the end user computer device or an RFID-chip.

The training machine assembly can be configured for user identification by a user identification device.

The user identification device can be the end user computer device. The user identification device can be the portable end user computer device.

The user identification device can comprise a component configured for wireless communication. The user identification device can comprise a component configured for RFID-communication.

The user identification device can comprise an RFID-chip. The component configured for wireless communication can comprise the RFID-chip.

The user identification device can be a bracelet. The bracelet can comprise a data storage component, such as an integrated circuit.

The bracelet can comprise the component configured for wireless communication.

The bracelet can comprise the RFID-chip. The RFID-chip can comprise the data storage component.

The training machine assembly can be configured for user identification by facial recognition.

The training machine assembly can be configured for capturing and/or receiving image data comprising image data relating to a face of the user.

The training machine assembly can be configured for processing the image data comprising the image data relating to the face of the user. The control device can be configured for processing the image data relating to the face of the user.

The training machine assembly can be configured for sending the image data relating to the face of the user to a data-processing system, such as the server system. The training machine assembly can be configured for receiving identification data from the data-processing system.

The camera can be mounted to the control device. The camera can be a part of the control device.

The camera can be connected to the control device via a wired connection.

An optional advantage can be a reliable, energy efficient and however releasable connection.

The camera can be connected to the control device via a wireless connection.

An optional advantage can be an easy mounting of the camera and/or a simplified assembly of the training machine assembly compared to a wired or integrated camera.

The training machine assembly can be configured to adjust the at least one training resistance based on the heart-rate of the user.

The training machine assembly can be configured to adjust the at least one training resistance based on the heart-rate variability of the user.

The training machine assembly can be configured to receive data indicating the heart-rate of the user. The training machine assembly can be further configured to adjust the at least one training resistance based on the data indicating the heart-rate of the user.

The data indicating the heart-rate of the user can be the heart-rate data.

The training machine assembly can be configured to receive data indicating the heart-rate variability of the user and to adjust the at least one training resistance based on the data indicating the heart-rate variability of the user.

The training machine assembly can be configured for adjusting the training resistance based on the user plan data which user plan data were updated at a preceding exercise of the user. An optional advantage can be that the training machine assembly can provide the training resistance so as to provide an optimal training effect for the user during the training.

The training machine assembly can be configured to adjust the at least one training resistance based on the heart-rate of the user during at least one of the preceding exercise of the user and a time between the preceding exercise of the user and a current exercise at the training machine assembly. An optional advantage can be that an optimal training as regards the heart-rateof the user can be provided. An optional advantage of adapting the training resistance based on the data of the preceding exercise can be that oscillations of the heart-rate during the exercise can be easily compensated for. An optional advantage of adjusting the at least one training resistance based on the heart-rate of the user during the time between the preceding and the current exercise can be that the training resistance can also be adjusted based on a drop of the heart-rate after the end of the preceding exercise, which can be a measure for an exhaustion of the user.

The training machine assembly can be configured to adjust the at least one training resistance based on the heart-rate variability of the user before the current exercise at the training machine assembly. This can be optionally advantageous, as the training resistance can then be adapted based on the heart-rate variability of the user when the user is not exercising.

The training machine assembly can be configured to receive data indicating the heart-rate of the user at least during the preceding exercise of the user and to adjust the at least one training resistance based on the data indicating the heart-rate of the user. The above advantages can apply accordingly.

In a second embodiment, a system is disclosed.

Advantages and definitions of terms discussed in the context of the training machine assembly can apply respectively to the disclosed system. That is, also if certain terms, definitions and advantages are discussed again in the disclosure regarding the system, the advantages, terms and definitions disclosed with the training machine assembly can be respectively applicable.

The system, comprises at least one or a plurality of training machine assemblies.

A plurality of the training machine assemblies can be according to any of the above-mentioned embodiments of a training machine assembly.

All the training machine assemblies can be according to any of the above-mentioned embodiments of a training machine assembly.

The system can comprise a communication network.

The communication network can be configured to enable data transmission between a plurality of the training machine assemblies of the system.

The communication network can be configured to enable data transmission between all training machine assemblies of the system.

The system is configured for data transmission to the server system.

The server system can be a server system as discussed in the context of the training machine assembly.

The system can comprise at least one communication component configured for the data transmission.

The system can be configured for receiving data from the server system.

The system can comprise at least one communication component configured for receiving the data.

The system can comprise a data-processing system. The data processing system can a server system.

The data-process system can comprise the at least one control devices of the at least one training machine assembly.

The data-processing system can comprise a server system.

The data-processing system can comprise the end user computer device.

The data processing system can comprise means of data processing, such as, processor units, hardware accelerators and/or microcontrollers. The data processing system can comprise memory components, such as, main memory (e.g. RAM), cache memory (e.g. SRAM) and/or secondary memory (e.g. HDD, SDD). The data processing system can comprise busses configured to facilitate data exchange between components of the data processing device, such as, the communication between the memory components and the processing components. The data processing system can comprise network interface cards that can be configured to connect the data processing device to a network, such as, to the Internet. The data processing system can comprise user interfaces, such as:

an output user interface, such as:
screens or monitors configured to display visual data,
speakers configured to communicate audio data (e.g. playing audio data to the user),
input user interface, such as:
the at least one camera configured to capture visual data (e.g. capturing images and/or videos of the user),
a microphone configured to capture audio data (e.g. recording audio from the user),
a keyboard configured to allow the insertion of text and/or other keyboard commands (e.g. allowing the user to enter text data and/or other keyboard commands by having the user type on the keyboard) and/or
a trackpad, mouse, touchscreen, joystick.

To put it simply, the data processing system can be or comprise a processing unit configured to carry out instructions of a program. The data processing system can be or comprise a system-on-chip comprising processing units, memory components and busses. The data processing system can be or comprise at least one of a personal computer, a laptop, a pocket computer, a smartphone, a tablet computer. The data processing system can be or comprise a server. The data processing device can be or comprise a processing unit or a system-on-chip that can be interfaced with at least one of a personal computer, a laptop, a pocket computer, a smartphone, a tablet computer and user interfaces (such as the above-mentioned user interfaces).

The data processing system can be configured for storing user data.

The data processing system can comprise a data storage component.

The data-processing system can comprise a plurality of devices that are portable.

The devices that are portable can be portable end user computer devices.

The data-processing system comprises a plurality of data-devices that are configured to be worn, carried and/or hold the by users.

The data-devices can for example user identification devices as discussed in the context of the training machine assembly.

The data-devices can for example be at least one of bracelets, smart watches, smart phone and the end user computer devices.

The data-devices can be configured for identification of a user. The data-devices can each comprise the features of the user identification device as disclosed in the context of the training machine assembly.

The data devices can each be specific to the user.

The data devices can be configured to capture user data, such as login data.

The data-devices can be configured for data storage.

The data-devices can comprise a data storage unit.

Each of the data-devices can comprise a data storage unit.

The data-devices can be configured for data transmission to another portion of the system. For example, the data-devices can be configured for data transmission to the data processing system. The data-devices can also be configured for data transmission to the server system. The data-devices can further be configured for data transmission to the control device.

The system can be configured for storing user data on the data-devices.

The data-devices can be configured for receiving data from another portion of the system.

The data-devices can comprise a transmission element configured for wired communication.

Such a transmission element can be a USB-plug and/or socket, or another plug and socket combination.

The data-devices can comprise a transmission element configured for wireless communication. Such a transmission element can comprise for example at least one of a WLAN data-transmitter, a component configured for RFID/NFC-communication and/or a Bluetooth™ data-transmitter.

The system can comprise at least one camera.

The at least one camera can be a 2D-camera. The term "2D-camera" is intended to be interpreted as discussed in the context of the disclosed training machine assembly.

Optionally, the system may not comprise more cameras than training machine assemblies. In other words, optionally, the system comprises at most as much cameras at training machine assemblies.

An optional advantage can be a cost-efficiency and simplicity of the system, in particular in cases where each training machine assembly comprises one camera. In such cases, also a modular design of the system can be an optional advantage, as it may not be necessary to provide for a separate camera.

The at least one camera can be at least one 2D-camera.

For example, each training machine assembly can comprise a 2D-camera.

The at least one camera can be at least one 3D-camera. The term "3D-camera" is intended to be interpreted as discussed in the context of the disclosed training machine assembly.

The at least one camera can be a set of at least one 3D-camera and at least one 2D-camera.

The at least one camera can be a set of at least one 3D-camera and a plurality of 2D-cameras.

An optional advantage can be that the 3D-camera can generate an image of the user from which data such as lengths of bones or distances of joints can be derived more precisely than from images captured by the 2D-cameras, and that from images captured by the 2D-cameras, more precise information can be derived based on the data captured by the 3D-camera.

The at least one camera can be a set of a plurality of 3D-cameras and a plurality of 2D-cameras.

At least one of the at least one 3D-camera can be a time-of-flight depth camera.

At least one of the at least one 3D-camera can be projected infrared depth camera.

At least one of the at least one 2D-camera is configured for sensing light in the visible spectrum.

For example, the at least one of the at least one 2D-camera can be an RGB-camera.

Optional advantages as discussed in the context of the disclosed training machine assembly can apply.

At least one of the at least one 2D-camera can be configured for sensing light in the infrared spectrum.

At least one of the at least one 2D-camera can be configured for sensing a reflection of ultrasonic waves and wherein the system comprises a source of ultrasonic waves.

In other words, at least one of the 2D-camera(s) can be a microphone configured for sensing ultrasonic waves, and/or at least one of the 2D-camera(s) can comprise such a microphone.

In such cases, the system can further comprise at least one corresponding emitter of ultrasonic waves.

At least one of the at least one 2D-camera can be configured for sensing a reflection of radar and wherein the system comprises a radar sender.

In other words, at least one of the 2D-camera(s) can comprise a radar antenna.

In such cases, the system can further comprise at least one corresponding emitter of electro-magnetic waves.

At least one of the at least one 2D-camera can be configured for sensing a reflection of laser light and wherein the system comprises a source of laser light.

A plurality or all of the training machine assemblies can each comprise a sensing unit that is configured for sensing the user's training effort as discussed in the disclosure of the training machine assembly.

The system can be configured for generating the heart-rate data of the user.

The heart-rate data can comprise the heart-rate variability data.

Advantages and definitions regarding the heart-rate data of the user and the heart-rate variability data can optionally apply according to the disclosure regarding the training machine assembly.

A plurality of training machine assemblies of the system can each comprise a heart-rate detection component. Each of the heart-rate detection components can be configured for sensing the heart-rate variability as discussed in the context of the training machine assemblies.

A plurality of training machine assemblies of the system can each comprise at least one automatically adjustable user support element as discussed in the context of the training machine assemblies.

The system can be configured for generating the heart-rate data of the user based on image data captured by at least one of the cameras. The system can be configured to perform this operation as discussed in the disclosure regarding the training machine assemblies.

The training machine assembly can be configured for generating the heart-rate data of the user based on the timestamped image data. The timestamped image data can comprise the features as discussed above.

The system can be configured for generating the heart-rate data of the user based on video data captured by the at least one camera.

The system can comprise a plurality of heart-rate sensing devices.

An optional advantage can be that the heart-rate of a plurality of users can be sensed. Another optional advantage can be that the heart-rate of the user can be sensed at different training machine assemblies.

The heart-rate sensing devices can be configured for generating the heart-rate data when in physical contact to the user. In other words, the heart-rate sensing devices can be configured for sensing the heart-rate of the user by physical contact.

Such heart-rate sensing devices can comprise electrodes, such as chest strap heart-rate monitors and/or handle bars comprising electrodes.

An optional advantage can be that sensing the heart-rate of the user by physical contact can provide precise results with a good reliability during training compared to results of contactless heart-rate sensing.

Each of a plurality of the training machine assemblies can comprise at least one of the heart-rate sensing devices. For example, each of the training machine assemblies can comprise a heart-rate sensing device in the user contact element, such as the handle.

An optional advantage can be that the heart-rate of the user can be sensed at each training machine assembly comprising a heart-rate sensing device, which can further be optionally advantageous in case of a circuit training setup of the training machine assemblies of the system.

The heart-rate sensing devices can be portable. The heart-rate sensing devices can be configured to be worn by a user.

The data devices can comprise the heart-rate sensing devices.

A plurality of end user computer devices can comprise the heart-rate sensing devices.

Each heart-rate sensing device can be at least one of a smart watch, a bracelet and another wearable fitness tracker device configured for heart-rate sensing.

The heart-rate sensing devices can be at least one of smart watches, bracelets and another wearable fitness tracker device configured for heart-rate sensing.

Another wearable fitness tracker device can for example be a fitness tracker comprising a shape of a ring and configured to be worn at a finger or a set of such rings, wherein the ring or each of the rings comprises a heart-rate sensing unit.

Each data-device can comprise at least one of the heart-rate sensing devices.

The system can be configured for generating the skeleton data of the user.

An optional advantage can be that the skeleton data of the user can be used for adjusting a plurality of training machine assemblies. Hence, generating the skeleton data of the user by the system can be more efficient.

The system can be configured for generating the skeleton data of the user based on image data captured by at least one of the at least one camera.

The system can be configured for generating the skeleton-trajectory data of the user based on image data captured by at least one of the at least one camera.

The system can be configured for at least one of the generating of the heart-rate data, the generating of the skeleton data and/or the generating of the skeleton-trajectory data of at least one or a plurality of users using training machine assemblies of the system.

The system can further be configured for using the at least one boundary condition corresponding to the respective training machine assemblies' geometries.

The respective training machine is intended to refer to a training machine where input data where generated and/or captured. For example, when skeleton-trajectory data are generated from image data of a user using a first training machine assembly, then the respective training machine assembly is said first training machine.

Furthermore, regarding the boundary conditions and their optional features, reference is made to the disclosure of the training machine assembly.

At least one of the at least one boundary condition can be possible positions of at least one part of the body of the user.

At least one of the at least one boundary condition can be possible trajectories of movable parts of at least one of the respective training machine assembly.

At least one of the at least one boundary condition can be possible trajectories of at least parts of the body of the user interacting with at least one of the respective training machine assemblies.

The system can be configured to sense the training effort of the user at a group of training machine assemblies.

Said group can comprise at least one training machine assembly configured for effort sensing.

The group of training machine assemblies can also comprise a plurality of the training machine assemblies of the system, which training machine assembly can be configured for effort sensing.

The group of training machine assemblies can comprise all training machine assemblies of the system. In other words, each training machine assembly can be configured for effort sensing.

The training machine assemblies of the group of training machine assemblies can each be configured for generating at least one of the heart-rate data, the skeleton data and the skeleton-trajectory data, and for using at least one or a plurality of boundary condition(s) corresponding to the geometry of the training machine assembly.

Each training resistance of the group of training machine assemblies can comprises a sensing unit that is configured for sensing the user's training effort.

The data processing system can be configured for storing data relating to the training-resistance value for at least one user of the at least one training machine assembly.

The data relating to the training-resistance value can be a measure for the training resistance value, such as at least one of a force, a torque and a force and/or a torque depending on another quantity (such as a velocity of a movement of a part of the respective training machine assembly).

The data relating to the training-resistance value can also be an indirect measure for the training resistance value, such as a control parameter for the training resistance. Such a control parameter can e.g. be a parameter used by the control device of the training machine assembly.

The system can be configured for generating activity data of the user based at least on an interaction of the user with at least one of the training machine assemblies.

The activity data can relate to the activity level of the user.

The system can be configured for generating heart-rate reference data.

The system can be configured for generating the heart-rate reference data based on at least one of the predetermined heart-rate data, the heart-rate data of the user corresponding to different activity levels of the user, the heart-rate data of the user corresponding to at least one of the at least one training resistance value, a comparison of portions or points of the heart-rate data of the user, and a gradient in the heart-rate data of the user.

The gradient in the heart-rate data of the user can be a gradient of the heart-rate of the user.

A plurality of the training machine assemblies of the system can each comprise the training resistance which is automatically adjustable. Said training machine assemblies can be configured to adjust the at least one training resistance.

The system can be configured for generating performance data for at least one user.

Generating the performance data for the at least one user can be based at least on the heart-rate data of the at least one user.

In other words, the system can be configured for generating the performance data of the user at least based on the heart-rate data of said user. The heart-rate data can for example be an indicator for an overall activity level of the user.

Generating the performance data for the at least one user can also be based at least on the heart-rate variability data of the at least one user.

For example, the heart-rate variability data can be an indicator for a fitness level and hence for a possible and/or healthy performance for the user.

Generating the performance data for the at least one user can also be based at least on the heart-rate reference data of the at least one user.

Generating the performance data can also be based at least on comparing the heart-rate data and the heart-rate reference data.

For example, a heart-rate above a threshold stored in the heart-rate reference data can be an indicator for an activity of the user.

Generating the performance data for the at least one user can also be based at least on the skeleton data of the at least one user.

For example, the system can be configured for detecting an injury of the user.

Generating the performance data for the at least one user can further be based at least on the skeleton-trajectory data of the at least one user.

For example, a correctness of an execution of an exercise can be a part of the performance data, which can be generated based at least on the skeleton-trajectory data.

Generating the performance data for the at least one user can further be based at least on the training resistance value of the training resistance used by the at least one user.

Generating the performance data for the at least one user can also be based at least on comparing a change of activity data and a change of the heart-rate data.

For example, a change of the heart-rate of the user after a change of the activity level can be compared. An optional advantage can be that a relation of these can be an indicator of a performance and/or a possible performance of the user.

Generating the performance data for the at least one user can also be based at least on comparing the training resistance value of the training resistance used by the at least one user and the heart-rate reference data.

As stated above, the system can be configured for generating the performance data in any of the above-disclosed ways.

The system can be configured for identifying a deviation in the performance data relating to the user and to thus generate performance-deviation data for the user.

The performance-deviation data can comprise data relating to an exhaustion level of the user.

The data relating to the exhaustion level of the user can be generated at least based on the heart-rate variability data.

In other words, the system can be configured for generating the data relating to the exhaustion level of the user based on the heart-rate variability data.

The system can be configured for generating the instruction data.

The system can further be configured for outputting the instruction data.

The system can comprise at least one user interface. The at least one user interface can be configured for outputting the instruction data.

The at least user interface can comprise the features discussed in the disclosure of the training machine assembly.

The system can comprise a plurality of user interfaces that are configured for outputting the instruction data.

Each of the user interfaces can be associated to a training machine assembly.

The system can be configured for generating the instruction data based at least on the performance data.

This can be optionally advantageous in order to instruct the user so as to exercise in a way leading to an optimal output.

The system can be configured to generate the instruction data based at least on the performance-deviation data.

This can be optionally advantageous to provide improved instruction data.

The system can be configured for adjusting at least one of the training resistances.

The system can be configured for adjusting all training resistances.

At least one or a plurality of the training machine assemblies of the system can be configured to adjust the at least one training resistance.

The system can be configured for automatically adjusting at least one or all automatically adjustable user support elements.

An optional advantage of the above-disclosed options for adjusting the training resistances can be that the system enables to user to train optimally with respect to a physiology and a training effect for the user.

At least one or a plurality of the training machine assemblies of the system can be configured to receive said data from the at least one or the plurality of further training machine assemblies.

The system can be configured for adjusting at least one or all of the training resistances based on the heart-rate data.

The system can be configured for adjusting at least one or all of the training resistances based on the heart-rate variability data.

The system can be configured to process the user plan data.

The user plan data can comprise data relating to at least one user exercise. The at least one user exercise can comprise a next exercise.

The user plan data can comprise data relating to a plurality of the user exercises. The plurality of the user exercises can comprise the next exercise.

The user plan data can comprise rule data for the user exercise(s).

The user plan data can comprise parameters for the user exercise(s).

The user plan data can comprise target performance data.

The user plan data can comprise target heart-rate data.

The target heart-rate data can comprise a target range for the heart-rate of the user.

The target range can comprise an upper and a lower end.

The user plan data can comprise types of the user exercise(s).

The user plan data can comprise an indication of at least one suitable training machine assembly for each user exercise.

The user plan data can comprise an indication of at least one order of the user exercise(s).

In such cases, for example, the rule data can comprise rules relating to the order of the user exercises and/or to admissible changes of the order of the user exercises.

The user plan data can comprise data relating to a training resistance for at least one user exercise.

The user plan data can comprise data relating to training resistances for a plurality of exercises.

In such cases, for example, the data relating to the training resistance(s) can comprise at least one training resistance value for the user exercises.

An optional advantage can be that the system can automatically adjust the training resistance to the user plan data. Hence, optionally advantageously, a risk of errors can be reduced and/or a reproducibility of a machine behaviour can be increased.

The system can be configured for receiving the user plan data.

The system can be configured for transmitting the user plan data.

An optional advantage of receiving and/or transmitting the user plan data can that a user can use different system to perform a same, similar and/or coordinated training.

The system can be configured for adapting the user plan data. That is, the system can be configured for modifying the user plan data.

The data-processing system can be configured for adapting the user plan data.

Adapting the user plan data can be based at least on the performance-deviation data of the user.

In other words, the system can be configured for adapting the user plan data based at least on the performance-deviation data of the user. Furthermore, the data-processing system can be configured for said adapting.

Adapting the user plan data can be based at least on the heart-rate data.

That is, the system can be configured for adapting the user plan data based at least on the heart-rate data. Furthermore, the data-processing system can be configured for said adapting.

Adapting the user plan data can be based at least on the heart-rate variability data.

In other words, the system can be configured for adapting the user plan data based at least on the heart-rate variability data. Furthermore, the data-processing system can be configured for said adapting.

Adapting of the user plan data can based at least on temporal changes of the heart rate of the user.

In other words, the system can be configured for adapting the user plan data based at least on the temporal changes of the heart rate of the user. Furthermore, the data-processing system can be configured for said adapting.

Adapting of the user plan data can be based at least on a measure for an increase and/or a decrease of the heart-rate of the user.

In other words, the system can be configured for adapting the user plan data based at least on the measure for the increase or the decrease of the heart-rate of the user. Furthermore, the data-processing system can be configured for said adapting.

The measure for the increase and/or the decrease of the heart-rate of the user can be a measure for a change of the heart-rate of the user.

The measure for the increase and/or the decrease of the heart-rate of the user can comprise a rise-time and/or a fall time of the heart-rate of the user to a certain value.

For example, said measure can comprise a rise-time of the heart-rate to a maximum desired pulse for training, e.g. after a start of a user exercise. Said measure can also comprise a fall-time of the heart-rate to a heart-rate near the resting heart rate of the user.

Said measure can also comprise a gradient, such as a first, a second and/or a higher derivative of the heart-rate. Such a derivative is intended to be understood as a first, second and/or higher derivative of the heart-rate with respect to time.

The user plan data can comprise data relating to the training resistance.

Furthermore, adapting of the user plan data can comprise adapting the data relating to the training resistance based on the performance data and the target performance data.

In other words, the system can be configured for adapting the data relating to the training resistance based on the performance data and the target performance data. Furthermore, the data-processing system can be configured for said adapting.

Furthermore, adapting of the user plan data can comprise adapting the data relating to the training resistance based on the heart-rate variability of the user.

In other words, the system can be configured for adapting the data relating to the training resistance based on the heart-rate variability of the user. Furthermore, the data-processing system can be configured for said adapting Adapting of the user plan data can comprise adapting the data relating to the training resistance based on the heart-rate data and the target heart-rate data.

In other words, the system can be configured for adapting the data relating to the training resistance based on the heart-rate data and the target heart-rate data. Furthermore, the data-processing system can be configured for said adapting.

For example, the system can be configured for adapting the user plan data by increasing the at least one training resistance value for at least one or a plurality of next user exercises in a case where the heart-rate of the user does not rise to the target heart-rate within a current exercise.

In another or the same example, the system can be configured for adapting the user plan data by decreasing the at least one training resistance value for the at least one or a plurality of next user exercises in a case where the heart-rate of the user exceeds the target heart-rate within a current exercise.

Adapting of the user plan data can comprise adapting the data relating to the training resistance based on the measure for the increase and/or the decrease of the heart-rate of the user.

That is, the system can be configured for adapting the data relating to the training resistance based on the measure for the increase and/or the decrease of the heart-rate of the user. The data-processing system can be configured for said adapting.

Adapting of the data relating to the training resistance can be based on history data relating to adapting the at least one training resistance and a change of the respective measure for the user performance.

The respective measure for the user performance can be at least one of any of the performance data, the heart-rate variability of the user, the heart-rate of the user and the measure for the increase and/or the decrease of the heart-rate of the user.

The history data can hence comprise data relating to the at least one training resistance and to at least one of these measures.

The system can be configured to perform the adapting based on the history data by a machine-learning algorithm trained with the history data. The data-processing system can be configured for performing the adapting in this way.

The machine learning-algorithm can for example be a pattern recognition algorithm and/or a time series analysis algorithm. The term machine learning is however intended to refer to machine learning and/or artificial intelligence in a more general sense, so that it can also comprise neural network-algorithms and deep learning algorithms.

The system can be configured for adjusting at least one of the training resistances based on at least a portion of the user plan data. The data-processing system can be configured for adjusting at least one of the training resistances based on at least a portion of the user plan data.

The system can be configured to generate the instruction data based on at least a portion of the user plan data.

Furthermore, the data-processing system can be configured to generate the instruction data based on at least the portion of the user plan data.

The instruction data can comprise data relating to a further exercise of the user, such as the next exercise and/or at least one or a plurality of possible training machine assemblies for the next exercise.

An optional advantage can be that the system can provide the user with instructions of which training machine assembly to use for an exercise when the user uses different systems which comprise different training machine assemblies. A merely exemplary application can be a user using different gyms at different days of the week, but still following single training plan.

The system can be configured to transmit at least a portion of the performance data.

The system can for example be configured to transmit said data to an end user computer device of an instructor and/or a medical practitioner.

The system can be configured to transmit at least a portion of the performance-deviation data.

For example, the system can be configured for transmitting data generated based on the user heart-rate, such as the maximum heart-rate of the user and/or the increase and/or decrease of the heart-rate of the user. Also, an exhaustion-level based on the user heart-rate can be transmitted.

Furthermore, the system can be configured for transmitting a portion of the performance-deviation data relating to the skeleton-trajectory data. An advantage can be that the they can indicate a quality of an exercise and that they may be helpful for a medical practitioner for further assessment of the user's health.

The system can be configured to transmit at least a portion of the heart-rate data.

The system can be configured to transmit at least a portion of the heart-rate reference data.

The system can be configured to transmit at least a portion of the skeleton data.

The system can be configured to transmit at least a portion of the skeleton-trajectory data.

The system can be configured to transmit at least a portion of the instruction data.

The system can be configured to transmit at least a portion of the user plan data.

The system can be configured to transmit the data to the server system.

The system can be configured to transmit the data to the end user computer device.

An optional advantage can be that a user of the end user computer device can access and/or visualise the data and hence provide improved and/or more efficient advice to the user.

The end user computer device can be portable, as discussed above.

The system can comprise the end user computer device.

The end user computer device can be configured for outputting at least a part of the instruction data.

The end user computer device can be configured for outputting at least a part of the user plan data.

An optional advantage can be that the user can access her/his user plan data.

The system can be configured for automatically adjusting at least one or all automatically adjustable user support elements based on comparison data.

The system can be configured for comparing the skeleton data to the skeleton-reference data and to thus generating skeleton-comparison data. The comparison data comprise at least a portion of the skeleton-comparison data.

Furthermore, the data-processing system can be configured for comparing the skeleton data to the skeleton-reference data.

The system can be configured for comparing the skeleton-trajectory data to the skeleton-reference data and to thus generating trajectory-comparison data. The comparison data can comprise at least a portion of the trajectory-comparison data.

The data processing system can be configured for comparing the skeleton-trajectory data to the skeleton-reference data.

Comparing the skeleton-trajectory data to the skeleton-reference data can comprise adapting the skeleton-reference data. The system can be configured for adapting the skeleton-reference data. The data-processing system can be configured for adapting the skeleton-reference data.

The adapted skeleton-reference data can be stored.

Said adapted skeleton-reference data can be stored with data relating to the user. An optional advantage can be that the adapted data do not need to be generated each time the trajectory-comparison data are generated.

Said adapted skeleton-reference data can also be deleted and/or not stored permanently. An optional advantage can be at least one of an improved privacy protection and lower storage requirements.

The skeleton-reference data can be generated for example based on skeleton-trajectory data of users who are exercising properly, such as instructors who use the training machine assembly. The skeleton-reference data can also be generated from a simulation of a user correctly exercising, for example a kinematics model.

The skeleton-reference data can be adapted when they are compared with the skeleton-trajectory data.

The skeleton-reference data, more particularly a portion referring to the trajectory-data, can be adapted based on the skeleton-data and/or the skeleton-comparison data.

This can be optionally advantageous, as it allows to compensate for differences between users, and more particularly between the user(s) whose data was used to generate the skeleton-reference data referring to the skeleton-trajectory data or to the simulation parameters used for the simulation.

The system can be configured for adjusting at least one of the at least one training resistance based on at least one of the comparison data, the skeleton-comparison data and the trajectory-comparison data.

The system can be configured for outputting the instruction data based on at least one of the comparison data, the skeleton-comparison data and the trajectory-comparison data.

For example, the system can output a portion of the instruction data corresponding to a certain part of the comparison data, such as an instruction regarding proper execution of the user exercise when the trajectory-comparison data indicate that the user does not properly execute the user exercise.

The system can be a system for strength training.

A plurality of the training machine assemblies of the system can be configured for adjusting the respective training resistance(s) based on the user plan data as discussed in the disclosure of the training machine assembly.

The system can be configured for user identification.

Details, options and advantages as discussed in the disclosure of the training machine assembly may optionally apply.

An optional advantage of the system being configured for user identification can be that the system can merge data from different training machine assemblies regarding a same user.

The system can further be configured for user identification by facial recognition.

Details, options and advantages as discussed in the disclosure of the training machine assembly may optionally apply.

The system can be a system for circuit training.

Each of the training machine assemblies can be configured for at least one user exercise. At least some user exercises can be different from each other.

The at least one user can be a plurality of users. The system can be configured for performing the steps that it performs for the at least one user for each of the plurality of the users respectively.

The system can be configured for performing the steps at different times.

For example, at least one or all of the heart-rate data, the skeleton-data, the skeleton-trajectory data and the types of comparison data can be generated for each user at a time when the respective user uses one of the at least one or the plurality of the training machine assemblies.

In the same or another example, the system can be configured for adjusting the at least one training resistance of one of the at least one training machine assembly according to each user's data respectively.

An optional advantage can be that the system can provide an improved training for a plurality of users. Another optional advantage can be that the system can provide an improved training for a plurality of users at a same time, particularly in cases where the at least one training machine assembly is a plurality of training machine assemblies.

The system can be configured for adjusting at least one or all of the training resistances for at least one of the user(s) respectively based on a portion of the heart-rate data relating to the heart-rate of the respective user during a preceding exercise performed by the user. The system can also be configured for adjusting said at least one or all of the training resistances for the respective user based on a portion of the heart-rate data relating to the heart-rate of the user during a time between the preceding exercise of the user and a respectively current exercise at the training machine assembly of the system that the user uses.

Adjusting the training resistance for a user based on his/her heart-rate during the preceding exercise can be optionally advantageous, as it can for example enable adapting the training resistances so as to keep the heart-rate of the user within a certain range.

Adjusting the training resistance for a user based on his/her heart-rate during a time between a preceding and the current exercise can be optionally advantageous as it can enable adapting the training resistances based on the drop of the heart-rate of the user after an end of the preceding exercise.

The system can be configured for adjusting at least one or all of the training resistances for the at least one user based on the heart-rate variability of the at least one user before the current exercise at the training machine assembly.

Corresponding advantages discussed in the training machine assembly embodiments can respectively apply.

The system can be configured for adapting the user plan data relating to a next exercise of the at least one user.

Adapting the user plan data relating to the next exercise of the user can be optionally advantageous, as it can enable adapting the next exercise based on at least one of the performance, the exhaustion, a measure for any of the two and another measure. Furthermore, adapting the user plan data for the next exercise of the user can be optionally advantageous as it enables providing a training that can be dynamically adapted to the user and/or his/her daily condition.

The adapting the user plan data relating to the next exercise of the user can be based at least on the performance-deviation data relating to at least one of the current and the current as well as at least one preceding user exercise of the user.

This can be optionally advantageous as it can allow to adapt the training resistance based on an actual performance, exhaustion or fitness of the user which can optionally be assessed based on the performance deviation data.

The adapting the user plan data relating to the next exercise of the user can be based at least on the heart-rate data relating to at least one of the current and the current as well as at least one preceding user exercise of the user. The above-disclosed advantages can optionally apply.

Adapting the user plan data relating to the next exercise of the user can be based at least on the heart-rate variability data relating to at least one of the current and the current as well as at least one preceding user exercise of the user.

Adapting the user plan data relating to the next exercise of the user can also based at least on temporal changes of the heart rate of the user during at least one of the current and the current as well as at least one preceding user exercise of the user.

Adapting the user plan data relating to the next exercise of the user can be based at least on a measure for an increase and/or a decrease of the heart-rate of the user during at least one of the current and the current as well as at least one preceding user exercise of the user.

Adapting of the user plan data can further comprise adapting the data relating to the respectively next training resistance based on the above-discussed types of data relating to at least one of the current and the current as well as at least one preceding user exercise of the user based on which the user-plan data relating to the training resistance can be adapted.

In a third embodiment, a data-processing system is disclosed.

Advantages and definitions of terms discussed in the context of the training machine assembly and/or of the system can apply respectively to the disclosed data-processing system. That is, also if certain terms, definitions and advantages are discussed again in the disclosure regarding the data-processing system, the advantages, terms and definitions disclosed with the training machine assembly and/or the system can be respectively applicable.

The data-processing system can be configured to receive data, send data and process data.

The data-processing system can be configured to receive the user plan data.

The data-processing system can be configured to generate the user plan data.

The data-processing system can be configured to receive and/or store the user plan data.

The user plan data can comprise data relating to the at least one user exercise, such as the next user exercise.

The user plan data can comprise data relating to the plurality of user exercises, such as the next user exercises.

The user plan data can comprise rule data for the user exercise(s).

The user plan data can comprise parameters for the user exercise(s). The parameters can be as disclosed in the context of the training machine assembly and/or the system.

The user plan data can comprise the target performance data.

The user plan data comprise target heart-rate data.

The target performance data can comprise the target heart-rate data.

The target heart-rate data can comprise a target range for the user heart-rate.

The user plan data can comprise types of the user exercise(s).

The user plan data can comprise an indication of the suitable training machine assemblies for each user exercise(s).

The user plan data can comprise an indication of the at least one order of the user exercise(s).

The user plan data can comprise data relating to the training resistance for at least one exercise.

The user plan data can comprise data relating to the training resistances for a plurality of exercises.

The data-processing system can be configured for processing the instruction data.

The data-processing system can be configured for generating the instruction data.

Generating the instruction data can comprise selecting the instruction data from a set of instruction data.

The set of instruction data can for example comprise different instructions. The set of instruction data can for example be a database comprising instruction data for different purposes.

The data-processing system can be configured for outputting instruction data. The data-processing system can also be configured for sending instruction data.

In other words, the data-processing system can be configured for sending and/or outputting at least a portion of the instruction data.

The data-processing system can be configured for generating the instruction data based on the user plan data.

The instruction data can comprise at least an indication relating to the training resistance for at least one exercise.

The instruction data can comprise at least an indication relating to the training resistances for the plurality of exercises.

The data-processing system can be configured for controlling at least one training resistance of at least one training machine assembly.

For example, the data-processing system can send data to the at least one training machine assembly based on which the at least one training machine assembly adjusts the at least one training resistance.

The data-processing can be configured for communication with the control device(s) of the at least one training machine assembly.

The at least one training machine assembly can comprise any of the features disclosed regarding the training machine assembly.

The at least one training machine assembly can be a plurality of training machine assemblies.

The at least one training resistance can be a plurality of training resistances.

The data-processing system is configured for controlling the at least one training resistance based on the user plan data.

The data-processing system can be configured for controlling the at least one training resistance based on the instruction data.

The data-processing system can be configured for controlling the at least one training machine assembly by sending data to the at least one training machine assembly.

The data-processing system can be configured for storing the heart-rate data of the user.

The data-processing system can be configured for processing the heart-rate data of the user.

The data-processing system can be configured for generating the heart-rate data of the user.

For example, the data-processing system can be configured for receiving data from the heart-rate sensing device and process said data in order to generate the heart-rate data.

The data-processing system can be configured for storing the heart-rate variability data of the user.

The data-processing system can also be configured for processing the heart-rate variability data of the user.

The data-processing system can be configured for generating heart-rate variability data of the user.

For example, the data-processing system can be configured for generating the heart-rate variability data based on the heart-rate data.

The data-processing system can be configured for determining the temporal changes of the heart rate of the user.

The data-processing system can be configured for processing the temporal changes of the heart rate of the user.

The data-processing system can be configured for determining the measure for the increase and/or the decrease of the heart-rate of the user.

The data-processing system can be configured processing the measure for the increase and/or the decrease of the heart-rate of the user.

The data-processing system can be configured for generating the image data of the user. The data-processing system can comprise at least one camera. The at least one camera can be configured for generating the image data.

The data-processing system can be configured for receiving the image data of the user. The data-processing system can be configured for receiving the image data from at least one camera. The data-processing system does not need to comprise the at least one camera. The camera can be remote from the data-processing system.

The data-processing system can be configured for generating at least one of the skeleton data and the skeleton-trajectory data of the user.

The data-processing system can be configured for receiving at least one of the skeleton data and the skeleton-trajectory data of the user.

The data-processing system can be configured for generating at least one of the skeleton data and the skeleton-trajectory data of the user based on the image data of the user.

Some possible implementations for generating the skeleton data as well as the skeleton-trajectory data are disclosed in the context of the training machine assembly.

The data-processing system can be configured for generating the heart-rate data of the user based on the image data of the user.

Some possible implementations for generating the heart-rate data are disclosed in the context of the training machine assembly.

The data-processing system can be configured for using the at least one boundary condition corresponding to the exercise of the user for generating the skeleton data of the user.

The data-processing system can be configured for using at least one of the at least one boundary condition corresponding to the exercise of the user for generating the heart-rate data of the user.

At least one of the at least one boundary condition can relate to the training machine assembly used to perform the user exercise.

At least one of the at least one boundary condition can relate to the possible positions of at least one part of the body of the user using the training machine assembly.

At least one of the at least one boundary condition can relate to the possible trajectories of movable parts of at least one of the respective training machine assembly.

At least one of the at least one boundary condition can relate to the possible trajectories of at least parts of the body of the user interacting with at least one of the respective training machine assemblies.

The data-processing system can be configured for storing the performance data. The data-processing system can also be configured for processing the performance data.

The data-processing system can be configured for generating the performance data.

The data-processing system can be configured for generating the performance data for the at least one user based at least on the heart-rate data of the at least one user.

The data-processing system can be configured for generating the performance data for the at least one user based at least on the heart-rate variability data of the at least one user.

The data-processing system can be configured for generating the performance data for the at least one user based at least on the heart-rate reference data of the at least one user.

The data-processing system can be configured for generating the performance data for the at least one user based furthermore on comparing the heart-rate data and the heart-rate reference data of the user.

The data-processing system can be configured for generating the performance data for the at least one user based at least on the skeleton data of the at least one user.

The data-processing system can be configured for processing the history data. The data-processing system can also be configured for processing the history data.

The data-processing system can be configured for generating the history data.

The data-processing system can be configured for storing the history data.

The history-data can comprise the data relating to the training resistances.

The history-data can comprise data relating to at least one training resistance for the at least one user exercise. The history-data can comprise data relating to at least one training resistances for a plurality of the user exercises.

The history-data can comprise the heart-rate data. The history-data can also comprise a portion of the heart-rate data.

The history-data can comprise the heart-rate variability data. The history data can also comprise a portion of the heart-rate variability data.

The history-data can comprise data relating to the temporal changes of the heart rate of the user.

The history-data can also comprise data relating to the measure for the increase and/or the decrease of the heart-rate of the user.

The history-data can comprise the instruction data. The history data can also comprise a portion of the instruction data.

The history-data can comprise the skeleton data. The history data can also comprise a portion of the skeleton data.

The history-data can comprise the skeleton-trajectory data. The history data can also comprise a portion of the skeleton-trajectory data.

The history-data comprise the performance data. The history-data can also comprise a portion of the performance data.

The data-processing system can be configured for receiving the reference data.

The data-processing system can also be configured for processing the reference data.

The data-processing system can be configured for generating the reference data.

The data-processing system can be configured for storing the reference data.

The reference data can comprise at least one of the skeleton-reference data and the heart-rate reference data.

The data-processing system can be configured for generating the comparison data.

The data-processing system can be configured for storing the comparison data.

The data-processing system can be configured for processing the comparison data.

The data-processing system can also be configured for receiving the comparison data.

The data-processing system can be configured for generating the comparison data by comparing data relating to the user to reference data. Said data relating to the user can for example comprise at least one of the skeleton data, the skeleton-trajectory data, the heart-rate data and the heart-rate variability data.

The reference data can comprise the skeleton-reference data.

The comparison data can comprise the skeleton-comparison data. The data-processing system can be configured for generating the skeleton-comparison data by comparing the skeleton data to at least a portion of the skeleton reference-data.

The comparison data can comprise the trajectory-comparison data. The data-processing system can be configured for generating the trajectory-comparison data by comparing the skeleton-trajectory data to the skeleton reference-data.

Comparing the skeleton-trajectory data to the skeleton-reference data can comprise adapting the skeleton-reference data. The data-processing system can be configured for adapting the skeleton-reference data.

The adapted skeleton-reference data can be stored.

Said adapted skeleton-reference data can be stored with data relating to the user.

Said adapted skeleton-reference data can also be deleted and/or not stored permanently.

The skeleton-reference data can be adapted when they are compared with the skeleton-trajectory data. The data-processing system can be configured to adapt the skeleton-reference data.

The skeleton-reference data, more particularly a portion referring to the trajectory-data, can be adapted based on the skeleton-data and/or the skeleton-comparison data.

The data-processing system can be configured for adapting the portion of the skeleton-reference data referring to the trajectory-data based on the skeleton-data and/or the skeleton-comparison data.

The reference data can comprise the heart-rate reference data.

The comparison data can comprise the heart-rate comparison data. The data-processing system can be configured for generating the heart-rate comparison data by comparing the heart-rate data to the heart-rate reference data.

The data-processing system can be configured for adapting the user plan data.

The data-processing system can be configured for adapting the user plan data based on the heart-rate data.

The data-processing system can be configured for adapting the user plan data based on the heart-rate variability data.

The data-processing system can be configured for adapting the user plan data based on the heart-rate variability data.

The data-processing system can be configured for adapting the user plan data based on the temporal changes of the heart rate of the user.

The data-processing system can be configured for adapting the user plan data based on the measure for the increase and/or the decrease of the heart-rate of the user.

The data-processing system can be configured for adapting the user plan data based on the skeleton data.

The data-processing system can be configured for adapting the user plan data based on the skeleton-trajectory data.

The data-processing system can be configured for adapting the user plan data based on the performance data.

The data-processing system can be configured for adapting the user plan data based on the performance target data.

The data-processing system can be configured for adapting the user plan data based on the history data.

The data-processing system can be configured for controlling the at least one training resistance based on the adapted user plan data.

The data-processing system can be configured for controlling the at least one training resistance based on the comparison data.

The data-processing system can be configured for adapting the instruction data based on the adapted user plan data.

The data-processing system can be configured for adapting the instruction data based on the comparison data.

The data-processing system can be configured for adapting the instruction data based on the history data.

The data-processing system can be configured for adapting the user plan data based on the history data.

The data-processing system can be configured for applying machine learning algorithms to the history data.

As discussed above, the term machine learning is intended to be understood in a broad manner, including artificial intelligence algorithms.

The data-processing system can be configured for applying pattern recognition algorithms to the history data.

The data-processing system can be configured for applying reinforcement-learning algorithms to the history data.

The data-processing system can be configured for applying neural-network algorithms to the history data.

The data-processing system can be configured to be connected to the heart-rate sensing device.

The data-processing system can comprise the heart-rate sensing device.

An example can be a data-processing system that comprises a smart watch and/or a fitness tracker which smart watch and/or fitness tracker can comprise the heart-rate sensing device.

The data-processing system can be configured for sensing the heart rate of the user.

The data-processing system can further be configured for sensing the heart-rate variability of the user.

The heart-rate sensing device can be configured for sensing the heart-rate variability of the user.

The data-processing system can be configured to receive data from the at least one wearable device, such as the data-device discussed in the disclosure of the system.

The at least one wearable device can be a plurality of wearable devices, such as the data-devices discussed in the disclosure of the system.

The system can comprise a plurality of heart-rate sensing devices.

Each of the at least one wearable device can comprise a heart-rate sensing device.

The at least one wearable device can further be configured for sensing the heart-rate of the user.

The at least one wearable device can further be configured for sensing the heart-rate variability of the user.

The data-processing system can comprise the end user computer device.

The end user computer device can be portable.

The end user computer device can be a smart mobile device.

The data-processing system can comprise a server system.

The data-processing system can be configured for sending data. The data-processing system can further comprise a communication component, such as a network interface card.

However, the person skilled in the art will easily understand that the communication component can also a different element, such as a transponder for wireless communication.

The data to be sent by the data-processing system can comprise the heart-rate data.

The data to be sent can also comprise a portion of the heart-rate data.

The data to be sent by the data-processing system can comprise the performance data. The data to be sent can also comprise a portion of the performance data.

The data to be sent by the data-processing system can comprise the instruction data.

The data to be sent can also comprise a portion of the instruction data.

The data to be sent by the data-processing system can comprise data relating to the at least one training resistance.

The data to be sent by the data-processing system can comprise data relating to the plurality of training resistances.

The data to be sent by the data-processing system can comprise the performance data. The data to be sent can also comprise a portion of the performance data.

The data to be sent by the data-processing system can comprise the comparison data and/or at least a portion thereof.

The data-processing system can be configured for receiving data.

The data to be received by the data-processing system can comprise the heart-rate data and/or at least a portion thereof.

The data to be received by the data-processing system can comprise the data relating to the at least one training resistance and/or to the plurality of training resistances.

The data to be received by the data-processing system can also comprise a portion of the data relating to the at least one training resistance and/or to the plurality of training resistances.

The data to be received by the data-processing system can comprise the heart-rate variability data or at least a portion thereof.

The data to be received by the data-processing system can comprise the history data.

The data-processing system can be configured to be connected to at least one training machine assembly which is according to the above disclosure of the training machine assemblies.

The at least one training machine assembly can be a plurality of training machine assemblies.

The data-processing system can be configured to be connected to a system according to any of the system embodiments.

The user can be a plurality of users. The data-processing system can be configured for processing data for a plurality of users.

The data-processing system can be configured for performing the steps that it performs for the at least one user for each of the plurality of the users respectively.

The data-processing system can be configured for performing the steps at a plurality of times, for example for each user at a time when a respective user uses the training machine assembly or the system.

The user plan data can comprise data relating to the training resistance for the at least one next exercise of the user.

The user plan data can comprise data relating to the training resistances for a plurality of exercises, comprising the at least one next exercise of the user.

The instruction data can comprise at least an indication relating to the training resistance for the at least one next exercise of the user.

The instruction data can comprise at least an indication relating to the training resistances for the plurality of exercises, comprising the at least one next exercise of the user.

The data-processing system can be configured for adapting the user plan data the user plan data relating to the next exercise of the at least one user.

The advantages disclosed in the context of the training machine assembly and the system can apply respectively.

The data-processing system can be configured for adapting the user plan data relating to the next exercise of the user based on the heart-rate data relating to at least one of the current and the current as well as at least one preceding user exercise of the user. In other words, the user plan data relating to a user exercise can be adapted based on the heart-rate data relating to at least one of the respectively preceding user exercise and a plurality of preceding user exercises.

The data-processing system can be configured for adapting the user plan data relating to the next exercise of the user based on the heart-rate variability data relating to at least one of the current and the current as well as at least one preceding user exercise of the user.

The data-processing system can also be configured for adapting the user plan data relating to the next exercise of the user based on the heart-rate variability data relating to a period between the current and the preceding user exercise.

The data-processing system can be configured for adapting the user plan data relating to the next exercise of the user based on the temporal changes of the heart rate of the user relating to at least one of the current and the current as well as at least one preceding user exercise of the user.

The data-processing system can be configured for adapting the user plan data relating to the next exercise of the user based on the measure for the increase and/or the decrease of the heart-rate of the user relating to at least one of the current and the current as well as at least one preceding exercise of the user The data-processing system can be configured for adapting the user plan data relating to the training resistance of the next exercise of the user based on the data relating to at least one of the current and the current as well as at least one preceding user exercise of the user, which data where above discussed as possible bases for said adapting of the user plan data relating to the training resistance.

The system can comprise a data-processing system according to the above disclosure.

In a fourth embodiment, a method is disclosed.

Advantages and definitions of terms discussed in the context of the training machine assembly, the system and/or of the data-processing system can apply respectively to the disclosed method. That is, also if certain terms, definitions and advantages are discussed again in the disclosure regarding the method, the advantages, terms and definitions disclosed with the training machine assembly, the system and/or the data-processing system can be respectively applicable.

The method comprises using the at least one training machine assembly.

The at least one training machine assembly can be to the above disclosure relating to training machine assembly.

The method can comprise sensing the image data. That is, the method can comprise sensing the image data with the at least one camera.

The method can comprises using the at least one camera.

The method can comprise controlling the at least one training machine assembly.

The method can for example comprise using the at least one control device for controlling the at least one training machine assembly.

The method can further comprise providing the at least one training resistance to the user.

The method can comprise applying the at least one training resistance to the contact element.

The method can further comprise providing at least one of a training force and a training torque to the user by at least one or a plurality of contact elements of the machine.

The contact element(s) can for example comprise at least one of a handle, a seat and a grip. The contact element(s) can for example be configured to be at least one of touched, gripped and pushed by the user.

Each training resistance, training force and/or training torque can comprise a training resistance value.

The method can comprise automatically adjusting the at least one training resistance, training force and/or training torque.

In other words, the method can comprise adjusting the at least one training resistance, training force and/or training torque without further input by an operator or the user.

The method can further comprise automatically adjusting the at least one user support element.

The method can comprise detecting the heart-rate of the user.

The method can comprise detecting the heart-rate of the user by the heart-rate detection component.

The method can comprise detecting the heart-rate of the user by the heart-rate sensing device. The heart-rate sensing device can be a device as discussed above.

The method can comprise sending data from the heart-rate sensing device to the training machine assembly.

The sending can be direct.

The sending can also be indirect, such as via at least one of a server and a data-processing system, wherein the at least one of the server and the data-processing system can for example convert the data. For example, a smart phone can receive data from the heart-rate sensing device, then convert the data, and transmit the converted data to the training machine assembly or the data-processing system.

The method can comprises connecting the heart-rate sensing device to the training machine assembly. The connecting can be direct. The connecting can also be indirect.

The method can comprise generating the heart-rate data of the user.

The method can comprise generating the heart-rate data of the user when the heart-rate sensing device is in contact with the user. In other words, the method can comprise generating the heart-rate data of the user during a time in which the heart-rate sensing device is in contact with the user.

The method can comprise generating the heart-rate data of the user when the heart-rate detection component is in contact with the user.

The method can comprise using the heart-rate sensing device.

The heart-rate sensing device can be portable. The heart-rate sensing device can be configured to be worn by the user.

The heart-rate sensing device can be at least one of a smart watch, a bracelet or another wearable fitness tracker device. The heart-rate sensing device can be as disclosed in the disclosure relating to the training machine assembly.

The heart-rate detection component can be mounted to the training machine assembly.

The heart-rate detection component can be configured to be touched by the user.

The method can comprise sensing the heart-rate of the user by the heart-rate detection component.

The method can comprise sensing the heart-rate variability of the user.

The method can comprise sensing the heart-rate variability of the user by the heart-rate sensing device.

The method can comprise sensing the heart-rate variability of the user by the heart-rate detection component.

The training machine assembly can generate the heart-rate data of the user. In other words, the method can comprise generating the heart-rate data of the user by the training machine assembly.

The method can comprise generating the heart-rate data of the user based at least on the image data. This can be performed as discussed above.

The image data can comprise the sequence of images. In other words, the method can comprise generating the heart-rate data at least based on the sequence of images.

The image data can comprise the timestamped sequence of images. That is, the method can comprise generating the heart-rate data at least based on the timestamped sequence of images.

The method can comprise sensing the video data.

The method can further comprise generating the heart-rate data of the user by the training machine assembly based on the video data. The method can comprise generating the video data by the camera.

The method can comprise capturing the image data with a frequency of at least 6.6 Hz as discussed above.

The method can comprise capturing the image data with a frequency of at least 7.4 Hz as discussed above.

The method can comprise generating the skeleton data.

The method can comprise generating the skeleton data based at least on the image data. For example, the method can comprise deducing positions of joints from fitting a model of a human to the image data.

The method can comprise generating the skeleton-trajectory data.

The method can comprise generating the skeleton-trajectory data based at least on the sensed image data. The skeleton-trajectory data can be as discussed above.

The method can comprise using the boundary conditions.

The boundary conditions can correspond to the training machine assembly's geometry. The geometry of the training machine assembly can be as discussed above.

The method can comprise using the boundary conditions for generating the skeleton-trajectory data based at least one the image data.

The method can comprise using the boundary conditions for generating the heart-rate data based at least one the image data.

The method can comprise using the boundary conditions for generating the skeleton data based at least one the image data.

At least one of the boundary conditions can be possible positions of at least one part of the body of the user, as discussed above.

At least one of the boundary conditions can be the possible trajectory of the at least one movable part of the training machine assembly.

The at least one of the boundary conditions can be possible trajectories of at least parts of the body of the user interacting with the training machine assembly.

The method can comprise using a supplementary sensing unit.

The method can comprise sensing the user's training effort.

The method can comprise sensing the user's training effort by the training resistance(s).

The method can comprise sensing the user's training effort by the supplementary sensing unit. The supplementary sensing unit can for example be a current sensor sensing a motor current, in cases where the training resistances comprise electric motors. The supplementary sensing unit can also be configured for sensing a torque and/or a force.

The method can comprise using not more than one camera as discussed above.

The method can comprise sensing the image data with the at least one 2D-camera.

The above sensing of the image data can be sensing the image data with the at least one 2D-camera.

The at least one camera can be at least one 3D-camera.

The at least one camera can be a set of at least one 2D-camera and at least one 3D-camera.

In other words, the method can comprise the cameras as disclosed in the context of the training machine assembly and/or the system.

At least one of the at least one 2D-camera can be configured to sense the light in the visible spectrum.

In other words, the method can comprise sensing the light in the visible spectrum.

The method can further comprise sensing the light in the visible spectrum by means of the 2D-camera.

The at least one 3D-camera can comprise the projected infrared depth camera.

The method can comprise using the projected infrared depth camera.

The at least one 3D-camera can comprise the time-of-flight depth camera.

The method can comprise using the time-of-flight depth camera.

The method can comprise combining the data of the at least one camera.

The method can comprise combining data of the at least one 2D-camera and the at least one 3D-camera.

The method can comprise outputting data. The outputting can be as discussed above in the context of the system and the training machine assembly.

The method can comprise using the user interface.

The method can comprise outputting the data by the user interface.

The method can comprise storing the heart-rate data of the user.

The training machine assembly can store the heart-rate data of the user. In other words, the method can comprise storing the heart-rate data of the user by the training machine assembly.

The method can comprise transmitting the heart-rate data of the user.

The training machine assembly can transmit the heart-rate data of the user. That is, the method can comprise transmitting the heart-rate data of the user by the training machine assembly.

The method can comprise comparing the heart-rate data of the user to the predetermined heart-rate data. Optional advantages and details can apply as discussed above.

The method comprises comparing the heart-rate data of the user to at least one of the at least one training resistance value.

The training machine assembly can compare the heart-rate data of the user to at least one of the at least one training resistance value. That is, the method can comprise comparing the heart-rate data of the user to at least one of the at least one training resistance value by the training machine assembly.

The method can comprise comparing heart-rate data of the user which heart-rate data correspond to different activity levels. This can for example be a resting pulse rate and a maximum heart-rate during exercise.

The method can comprise the training machine assembly comparing the heart-rate data of the user which heart-rate data correspond to different activity levels.

The method can comprise generating the heart-rate comparison data.

The method can comprise generating the heart-rate comparison data by comparing the heart-rate data of the user to the predetermined heart-rate data.

The method can comprise generating the heart-rate comparison data by comparing the heart-rate data of the user which heart-rate data are corresponding to different activity levels of the user.

The method can comprise generating the heart-rate comparison data by comparing the heart-rate data of the user to at least one of the at least one training resistance value.

The method can comprises generating the heart-rate comparison data by determining the heart-rate variability.

The method can comprise determining the heart-rate variability based on the heart-rate data.

The heart-rate comparison data can comprise the heart-rate variability data.

The method can comprise comparing the skeleton data to the skeleton-reference data and to thus generate the skeleton-comparison data.

The training machine assembly can compare the skeleton data to the skeleton-reference data. In other words, the method can comprise comparing the skeleton data to the skeleton-reference data.

The method can comprise comparing the skeleton-trajectory data to the skeleton-reference data and to thus generate the trajectory-comparison data.

Comparing the skeleton-trajectory data to the skeleton-reference data can comprise adapting the skeleton-reference data.

The method can comprise storing the adapted skeleton-reference data.

The method can comprise storing said adapted skeleton-reference data with data relating to the user.

The method can also comprise deleting and/or not permanently storing said adapted data skeleton-reference data.

The method can comprise generating the skeleton-reference data for example based on skeleton-trajectory data of users who are exercising properly, such as instructors who use the training machine assembly. The method can also comprise generating the skeleton-reference data from a simulation of a user exercising correctly, for example based on a kinematics model.

The method can comprise adapting the skeleton-reference data when they are compared to the skeleton-trajectory data.

The method can comprise adapting the skeleton-reference data, more particularly a portion referring to the trajectory-data, based on the skeleton-data and/or the skeleton-comparison data.

The training machine assembly can compare the skeleton-trajectory data to the skeleton-reference data. In other words, the method can comprise comparing the skeleton-trajectory data to the skeleton-reference data by the training machine assembly.

The method can comprise transmitting the heart-rate comparison data.

The method can further comprise transmitting the skeleton-comparison data.

The method can also comprise transmitting the trajectory-comparison data.

The method can comprise transmitting at least one of the heart-rate comparison data, the skeleton-comparison data and the trajectory-comparison data.

The training machine assembly can transmit the at least one of the heart-rate comparison data, the skeleton-comparison data and the trajectory-comparison data. In other words, the method can comprise transmitting the data by the training machine assembly.

The method can comprise transmitting said data to the data-processing system.

An optional advantage can be that the data-processing system can be configured for further processing of the data.

Another optional advantage can be that a data-processing system which processes data can be more cost-efficient and/or easier to operate than a comparable data-processing unit in the training machine assembly.

The preceding two advantages can respectively apply to the following three options.

The method can comprise transmitting said data to the end user computer device.

The end user computer device can be a portable end user computer device. In other words, the method can comprise using the portable end user computer device as end user computer device.

The method can comprise transmitting said data to the server system.

The method can comprise transmitting said data to at least one or a plurality of further training machine assemblies.

The method can comprise receiving at least one of the heart-rate comparison data, the skeleton-comparison data and the trajectory-comparison data.

The training machine assembly can receive the at least one of the heart-rate comparison data, the skeleton comparison data and the trajectory-comparison data. In other words, the method can comprise receiving said data by the training machine assembly.

The method can comprise receiving said data from the data-processing system.

This can be optionally advantageous as the data-processing system may be able to process, store and/or agglomerate said data more efficiently than a training machine assembly or an adapted data-processing unit therein.

The method can comprise receiving said data from the at least one or a plurality of further training machine assemblies.

The method can comprise adjusting the at least one automatically adjustable user support element based on at least one of the skeleton-comparison data and the trajectory-comparison data.

The method can comprise adjusting the at least one training resistance based on at least one of the skeleton-comparison data and the trajectory-comparison data.

The method can comprise outputting data based on at least one of the skeleton-comparison data and the trajectory-comparison data.

The method can comprise outputting data based on the heart-rate comparison data.

The method can comprise receiving the user plan data.

The training machine assembly can receive the user plan data. That is, the method can comprise receiving the user plan data by the training machine assembly.

The method can comprise adjusting the training resistance based on the user plan data.

The training machine assembly can comprise adjusting the training resistance based on the user plan data.

The method can be a method for strength training.

The method is a method for operating a strength training machine. The strength training machine can for example be the strength training machine assembly. The strength training machine can be configured for strength training, for example in contrast to mere stamina training.

The method can be a method for operating the training machine assembly in a circuit training.

The method can comprise performing a user identification step. The user identification step can comprise verifying an identity of the user.

The method can comprise using the user identification device.

The user identification step can comprise using the user identification device. In other words, the user identification step can comprise identifying the user, using at least the user identification device.

The user identification step can comprise identifying the user by facial recognition.

This can be optionally advantageous, as it can enable simple and contactless identification of the user, particularly if the method comprises using the at least one camera, since image data are already available anyways.

The image data can be sensed with the at least one camera. That is, the method can comprise sensing the image data by means of the at least one camera.

The method can comprise adjusting the at least one the at least one training resistance, training force and/or training torque based on the heart-rate of the user.

The method can comprise adjusting the at least one of the at least one training resistance, training force and/or training torque based on the heart-rate variability of the user.

The at least one training machine assembly can be a plurality of training machine assemblies. The at least one training resistance can be a plurality of training resistances.

The method can comprise performing at least portion and/or a step of the method, as described above, a plurality of times by different training machine assemblies of the plurality of training machine assemblies.

In other words, the method can comprise using a plurality of training machine assemblies and repeating some steps by different training machine assemblies.

For example, if the plurality of training machine assemblies comprises a training machine assembly without adjustable user support element, then the step of adjusting the adjustable user support element can be unnecessary for said machine.

In another example, it may be sufficient to generate the skeleton data only once or only once per training for each user, since they will most probably not chance during the training session.

The method can comprise operating the plurality of the training machine assemblies for a plurality of users. The method can comprise performing the steps of the method for the users at different times, but it can also comprise performing the steps of the method for some users at a same time or substantially at a same time. That is, the method can also comprise performing the method for users that are exercising at the same time.

The user can hence be at least one user or a plurality of users.

The plurality of the training machine assemblies can be according to the disclosed system. That is, the method can comprise operating a system according to at least an aspect of the above description of a system.

The method can comprise performing method steps or portions of the method as described above for each of the training machine assemblies.

A plurality of the plurality of training machine assemblies can be according to an above-described training machine assembly.

All of the plurality of training machine assemblies can be according to an above described training machine assembly.

The method can comprise transmitting data between the training machine assemblies.

The method can comprise operating a communication network that links the training machine assemblies.

The method can comprise transmitting data to the server system.

The method can comprise receiving data from the server system.

The method can comprise using the data processing system.

The method can comprise storing the user data.

The data-processing system can store the user data. In other words, the method can comprise storing the user data by the data-processing system.

The data-processing system can comprise a plurality of devices that are portable.

That is, the method can comprise using a data-processing system comprising a plurality of portable devices.

The data-processing system can comprise a plurality of the data-devices that are configured to be worn, carried and/or hold the by users, as discussed above.

The method can comprise identifying single users by means of at least one data-device. In other words, the method can comprise identifying singles users by means of at least one of the data-devices.

The method can comprise storing data on the data-devices.

The data-devices can transmit data. In other words, the method can comprise transmitting data by the data-devices.

The method can comprise storing the user data on the data-devices.

An optional advantage can be that the user data can be in control of the users, particularly when each data-device is user-specific. Hence, optionally, an improved data protection may be enabled.

The data-devices can receive data. In other words, the method can comprise receiving data by the data-devices.

The data-devices can communicate by wired communication.

The data-devices can communicate by wireless communication, such as WLAN, RFID-communication, NFC and/or other wireless communication.

The method can comprise using the at least one camera.

The at least one camera can be the 2D-camera. In other words, the method can comprise using the 2D-camera.

The method can comprise not using more cameras than training machine assemblies.

This can be analogous to the corresponding optional feature of the disclosed system.

The at least one camera can be the at least one 2D-camera. In other words, the method can comprise using the at least one 2D-camera.

The at least one camera can be at least one 3D-camera. That is, the method can comprise using the at least one 3D-camera.

The at least one camera can be a set of at least one 3D-camera and at least one 2D-camera. That is, the method can comprise using a set of cameras comprising at least one 3D-camera and at least one 2D-camera.

The at least one camera can be a set of at least one 3D-camera and a plurality of 2D-cameras. In other words, the method can comprise using a set of at least one 3D-camera and a plurality of 2D-cameras.

The at least one camera can be a set of a plurality of 3D-cameras and a plurality of 2D-cameras. That is, the method can comprise using a set of cameras comprising a plurality of 3D-cameras and a plurality of 2D-cameras.

The at least one 3D-camera can comprise a time-of-flight depth camera. In other words, the method can comprise using a time-of-flight depth camera as 3D-camera.

The at least one 3D-camera can comprise a projected infrared depth camera. That is, the method can comprise using a projected infrared depth camera as 3D-camera.

At least one of the 2D-camera(s) can sense the light in the visible spectrum. That is, the method can comprise sensing light in the visible spectrum by means of at least one of the at least one 2D-camera.

At least one 2D-camera can sense light in the infrared spectrum. The method can comprise sensing light in the infrared spectrum by means of at least one of the at least one 2D-camera.

At least one 2D-camera can sense the reflection of the ultrasonic waves and wherein the plurality of training machine assemblies comprises a source of ultrasonic waves. In other words, the method can comprise sensing the reflection of the ultrasonic waves by means of at least one 2D-camera, and the method can further comprise generating ultrasonic waves. As discussed above, the method may hence comprise using a 2D-camera that is a microphone adapted for sensing said reflection and further a source of said ultrasonic waves.

The at least one 2D-camera can sense a reflection of radar. That is, the method can comprise sensing a reflection of radar with at least one 2D-camera. The method can further comprise emitting radio waves.

The method can comprise sensing a reflection of laser light with at least one 2D-camera.

The method can further comprise emitting laser light.

The method can comprise generating the heart-rate data of the user.

The heart-rate data can comprise the heart-rate variability data.

A plurality of the training machine assemblies that are used in the method can be according to any of the above-discussed aspects of the disclosed training machine assembly.

A plurality of the training machine assemblies that are used in the method can be according to any of the above-discussed aspects of the disclosed training machine assembly.

The method can comprise using a plurality of the heart-rate sensing devices. The method can further comprise sensing the heart-rate of the user(s) by the plurality of the heart-rate sensing devices.

The heart-rate sensing devices can generate the heart-rate data when in physical contact to the user. In other words, the method can comprise generating the rate-rate data by the heart-rate sensing devices when the latter are in physical contact to the user.

The heart-rate sensing devices can be portable. That is, the method can comprise using portable heart-rate sensing devices.

The generating of the heart-rate data of the user can be based on the image data as discussed above. At least one or each step of generating the heart-rate data can be according to the above disclosure of generating the heart-rate data based on the image data.

The heart-rate sensing devices can be at least one of smart watches, bracelets or another wearable fitness tracker device configured for heart-rate sensing. In other words, the method can comprise using at least one of said types of heart-rate sensing devices.

Each data-device can comprise at least one of the heart-rate sensing devices. The method can thus comprise sensing the heart-rate of the user(s) by means of the data-devices, wherein each data-device can comprise at least one of the heart-rate sensing devices.

The method can comprise generating the skeleton data of the user.

The method can comprise generating skeleton data of the user based on the image data, as discussed above. In other words, the method can comprise generating at least a portion of the skeleton data of the user based on the image data.

The method can comprise generating skeleton-trajectory data of the user based on the image data captured by at least one of the at least one camera.

The method can comprise generating respectively at least one of the heart-rate data, the generating of the skeleton data and the generating of the skeleton-trajectory data of at least one or a plurality of users using the training machine assemblies.

The method can further comprise using the boundary conditions corresponding to the geometries of the respective training machine assemblies.

At least one of the boundary conditions can be possible positions of at least one part of the body of the user using a respective training machine assembly.

The method can hence comprise using possible positions of at least one part of the body of the user using the respective training machine assembly as boundary condition.

The respective training machine assembly can be a training machine assembly with which the user interacts while the image data are captured, e.g. with which the user is exercising or at which the user sits.

At least one of the boundary conditions can be possible trajectories of movable parts of a respective training machine assembly, as discussed above.

At least one of the boundary conditions can be possible trajectories of at least a part of the body of the user interacting with a respective training machine assembly, as discussed above.

The method can comprise sensing efforts of the user at different training machine assemblies.

The method can further comprise sensing efforts of users at different training machine assemblies.

The method can further comprise storing data relating to the training-resistance value for at least one user using at least one of the training machine assemblies. The data relating to the training resistance value can be as described above.

The data-processing system can store the data relating to the training-resistance value. That is, the method can comprise storing the data relating to the training-resistance value by the data-processing system.

The method can comprise generating the activity data of the user based at least on an interaction of the user with at least one of the training machine assemblies.

The method can comprise generating the heart-rate reference data.

The method can comprise generating the heart-rate reference data based on the predetermined heart-rate data.

The method can comprise generating the heart-rate reference data based on the heart-rate data of the respective user corresponding to different activity levels of the respective user.

An example can heart-rate reference data comprising a resting heart-rate of the user under normal conditions as well as a maximum heart-rate.

The method can also comprise generating the heart-rate reference data based on the heart-rate data of the user corresponding to at least one of the at least one training resistance value.

The method can comprise generating the heart-rate reference data based on the comparison of portions or points of the heart-rate data of the user.

The method can also comprise generating the heart-rate reference data based on the gradient in the heart-rate data of the user.

The used training machine assemblies can be according to any aspect of the above-disclosed training machine assembly. Particularly, they can each comprise at least one camera.

The method can comprise generating the performance data for at least one user.

The performance data for the at least one user can be generated based at least on the heart-rate data of the at least one user.

The performance data for the at least one user can be generated based at least on the heart-rate variability data of the at least one user.

The performance data for the at least one user can be generated based at least on the heart-rate reference data of the at least one user.

The performance data for the at least one user can be generated based at least on comparing the heart-rate data and the heart-rate reference data.

The performance data for the at least one user can be generated based at least on the skeleton data of the at least one user.

Generating the performance data for the at least one user can also be based at least on the skeleton-trajectory data of the at least one user.

Generating the performance data for the at least one user can be based at least on the training resistance value of the training resistance used by the at least one user.

Generating the performance data for the at least one user can also be based at least on comparing the change of the activity data and the change of the heart-rate data. For example, the method can comprise generating performance data regarding a drop of the heart-rate of the user after an end of an exercise and a rise of the heart-rate of the user after a start of an exercise.

Generating the performance data for the at least one user can be based at least on comparing the training resistance value of the training resistance used by the at least one user and the heart-rate reference data.

The method can comprise generating the performance-deviation data for the user.

The performance-deviation data can be generated by identifying a deviation in the performance data relating to the user. In other words, the method can comprise identifying a deviation in the performance data relating to the user and thus generating the performance-deviation data for the user.

The performance-deviation data can comprise data relating to the exhaustion level of the user. The method can comprise generating said data relating to the exhaustion level of the user.

The method can comprise generating the data relating to the exhaustion level of the user at least based on the heart-rate variability data.

The method can comprise generating the instruction data. The instruction data can be as discussed above.

Generating the instruction data can comprise selecting instruction data elements from a set of instruction data elements.

The method can further comprise outputting the instruction data.

The method can further comprise using the at least one user interface.

The at least one user interface can output the instruction data. That is, the method can comprise outputting the instruction data by the at least one user interface.

The at least one user interface used in the method can be a plurality of user interfaces. That is, the method can comprise using a plurality of user interfaces. The method can further comprise outputting at least a portion of the instruction data by the user interfaces.

The instruction data can be generated at least based on the performance data. That is, the method can comprise generation the instruction data at least based on the performance data.

The instruction data can be generated at least based on the performance-deviation data. In other words, the method can comprise generating the instruction data at least based on the performance-deviation data.

The method can comprise adjusting at least one of the training resistances.

The method can comprise adjusting all training resistances.

The method can comprise automatically adjusting the at least one user support element.

The method can also comprise automatically adjusting a plurality of user support elements.

Said plurality of user support elements can comprise user support elements belonging to multiple training machine assemblies, wherein each user support element belongs to one training machine assembly.

The method can comprise automatically adjusting at least one user support element of each of the training machine assemblies of the plurality of training machine assemblies.

The training resistances of each of the used training machine assemblies can be automatically adjustable, as discussed for the training machine assembly.

At least one or a plurality of the used training machine assemblies can be according to any aspect of the disclosed training machine assembly, particularly, the can be configured for adjusting at least one of the at least one automatically adjustable user support element based on at least one of the skeleton-comparison data and the trajectory-comparison data.

The method can comprise adjusting the at least one training resistance based on the heart-rate data.

The method can comprise adjusting the at least one training resistance based on the heart-rate variability data.

The method can comprise processing the user plan data. The user plan data can be as discussed above, e.g. in the context of the disclosed system.

The user plan data can comprise data relating to the at least one user exercise, such as the next user exercise.

The user plan data can comprise data relating to the plurality of user exercises.

The user plan data can comprise the rule data for the user exercise(s).

The user plan data can comprise the parameters for the user exercise(s).

The user plan data can comprise the target performance data.

The user plan data can comprise the target heart-rate data.

The target heart-rate data can comprise a target range for the user heart-rate.

The user plan data can comprise the types of the user exercise(s).

The user plan data can comprise the indication of the suitable training machine assemblies for each user exercise(s).

The user plan data can comprise an indication of at least one order of the user exercise(s).

The user plan data can comprise data relating to the training resistance for at least one exercise.

The user plan data can comprise data relating to the training resistances for a plurality of exercises.

The method can comprise receiving the user plan data.

The method can comprise transmitting the user plan data.

The method can comprises adapting the user plan data.

Adapting the user plan data can be based at least on the performance-deviation data of the user. In other words, the method can comprise adapting the user plan data based at least on the performance-deviation data of the user.

Adapting the user plan data can be based at least on the heart-rate data. That is, the method can comprise adapting the user plan data based at least on the heart-rate data.

Adapting the user plan data can be based at least on the heart-rate variability data. In other words, the method can comprise adapting the user plan data based at least on the heart-rate variability data.

Adapting the user plan data can be based at least on the temporal changes of the heart-rate of the user. That is, the method can comprise adapting the user plan data based at least on the temporal changes of the heart-rate of the user.

The user plan data can be based at least on the measure for the increase or decrease of the heart-rate of the user, as discussed above.

The user plan data can comprise the data relating to the training resistance.

Adapting the user plan data can comprise adapting the data relating to the training resistance. That is, the method can comprise adapting a portion of the user plan data relating to the training resistance.

Adapting the data relating to the training resistance can be based at least on the performance data and the target performance data. That is, the method can comprise adapting the data relating to the training resistance based at least one the performance data and the target performance data.

Adapting the data relating to the training resistance can be based at least on the heart-rate variability of the user. That is, the method can comprise adapting the data relating to the training resistance based at least on the heart-rate variability of the user.

Adapting the data relating to the training resistance can be based at least on the heart-rate data and the target heart-rate data. That is, the method can comprise adapting the data relating to the training resistance based at least on the heart-rate data and the target hart-rate data.

Adapting the data relating to the training resistance can be based at least on the measure for the increase or decrease of the heart-rate of the user. In other words, the method can comprise adapting the data relating to the training resistance based on the measure for the increase or decrease of the heart-rate of the user.

Adapting the data relating to the training resistance can also be based on history data relating to adapting the training resistance and the change of the respective measure for the user performance, as discussed in the respective part of the disclosure relating to the system.

The method can further comprise adapting the data relating to the training resistance based on the history data by a machine-learning algorithm trained with the history data, as discussed in the respective part of the disclosure relating to the system.

The method can further comprise adjusting at least one of the training resistances based on at least a portion of the user plan data.

The method can comprise generating the instruction data based on at least a portion of the user plan data.

The instruction data can comprise data relating to a further exercise of the user, such as the type of the next exercise or the next training machine assembly to use.

The method can comprise transmitting at least a portion of the performance data.

The method can comprise transmitting at least a portion of the performance-deviation data.

The method can comprise transmitting at least a portion of the heart-rate data.

The method can comprise transmitting at least a portion of the heart-rate reference data.

The method can comprise transmitting at least a portion of the skeleton data.

The method can comprise transmitting at least a portion of the skeleton-trajectory data.

The method can comprise transmitting at least a portion of the instruction data.

The method can comprise transmitting at least a portion of the user plan data.

The method can comprise transmitting said above-mentioned data or the portions of these data to the server system.

The method can comprise transmitting said above-mentioned data or the portions of these data to the end user computer device.

The end user computer device can be portable. In other words, the method can comprise transmitting said above-mentioned data or the portions thereof to the portable end user computer device.

The method can comprise using the end user computer device.

The method can comprise outputting a portion of the instruction data via the end user computer device.

This can be optionally advantageous, as it may enable the user to receive the instruction data from the same device at different training machine assemblies.

The method can comprise outputting a portion of the user plan data.

The method can comprise automatically adjusting the at least one user support element based on the comparison data.

The method can comprise comparing the skeleton data to the skeleton-reference data and thus generating the skeleton-comparison data.

The comparison data can comprise at least a portion of the skeleton-comparison data.

The method can comprise comparing the skeleton-trajectory data to the skeleton-reference data and thus generating the trajectory-comparison data.

The comparison data can comprise at least a portion of the trajectory-comparison data.

Comparing the skeleton-trajectory data to the skeleton-reference data can comprise adapting the skeleton-reference data.

The method can comprise storing the adapted skeleton-reference data.

Said adapted skeleton-reference data can be stored with data relating to the user. In other words, the method can comprise storing the adapted skeleton-reference data with data relating to the user.

Said adapted skeleton-reference data can also be deleted and/or not stored permanently. That is, the method can also comprise deleting and/or not permanently storing the adapted skeleton-reference data.

The skeleton-reference data can be generated for example based on skeleton-trajectory data of users who are exercising properly, such as instructors who use the training machine assembly. The skeleton-reference data can also be generated from a simulation of a user correctly exercising, for example a kinematics model.

The skeleton-reference data can be adapted when they are compared and the skeleton-trajectory data. In other words, the method can comprise adapting the skeleton-reference data when comparing the skeleton-reference data and the skeleton-trajectory data.

The skeleton-reference data, more particularly the portion thereof referring to the skeleton trajectory-data, can be adapted based on the skeleton-data and/or the skeleton-comparison data.

The method can comprise adjusting at least one of the at least one training resistance based on at least one of the comparison data, the skeleton-comparison data and the trajectory-comparison data.

The method can comprise outputting the instruction data based on at least one of the comparison data, the skeleton-comparison data and the trajectory-comparison data.

The method can be a method for operating the training machine assemblies for strength training.

The method can be a method for operating training machine assemblies for circuit training.

The method can comprise providing a plurality of different training resistances to the plurality of users at a same time by a plurality of contact elements of the training machine assemblies. In other words, the method can comprise operating the training machine assemblies so as to provide training resistances to multiple users at a same time.

An example thereof can for example be a circuit training with 10 machines and 8 users, wherein the 8 users are training at 8 different machines and change the machine after the exercising time for one machine is over.

Each of a plurality of the training machine assemblies can be configured for outputting data via the user interface based on the heart-rate comparison data. In other words, the method can comprise outputting data based on the heart-rate comparison data by means of the user interfaces.

Each of the training machine assemblies used in the method can be configured for at least one user exercise. At least some of the user exercises can be different from each other. In other words, the method can comprise using the training machine assemblies to provide at least some different user exercises, wherein each training machine assembly is used to provide one of the user exercises and wherein further, some of the user exercises can be different.

The method can comprise adjusting at least one of the training resistances for the next user exercise of a single user and/or each of the at least one user. That is, the method can comprise adjusting at least one of the training resistances for the next exercise of at least one user and/or respectively for all users.

The method can comprise adjusting at least one or all of the training resistances for the next user exercise of at least one of the user(s) based on a portion of the heart-rate data relating to the heart-rate of the respective user during at least one of a current exercise performed by the user and a time between the current exercise of the user and a respectively next exercise of the user. In other words, the method can comprise adjusting at least one training resistance for the next user exercise of a user based on the heart-rate data of the user relating to the current user exercise and/or during a time between the current and the next exercise. The method can comprise performing said adjusting for at least one user, of for each of a the users, when the at least one user is a plurality of users.

The advantages and details can be as disclosed and discussed in the context of the training machine assembly, the system and the data-processing system.

The method can comprise adjusting at least one or all of the training resistances for the current user exercise of the at least one user based on the heart-rate variability of the at least one user before the current exercise at the training machine assembly.

The method can comprise adapting the user plan data relating to the next exercise of the at least one user.

The adapting of the user plan data relating to the next exercise of the user can be based at least on the performance-deviation data relating to at least one of the current and the current as well as at least one preceding user exercise of the user.

The adapting of the user plan data relating to the next exercise of the user can also be based at least on the heart-rate data relating to at least one of the current and the current as well as the at least one preceding user exercise of the user.

The adapting of the user plan data relating to the next exercise of the user can be based at least on the heart-rate variability data relating to at least one of the current and the current as well as the at least one preceding user exercise of the user.

The adapting of the user plan data relating to the next exercise of the user can be based at least on the heart-rate variability data relating a period during the current and the preceding exercise of the user.

The adapting of the user plan data relating to the next exercise of the user can also be based at least on the temporal changes of the heart rate of the user during at least one of the current and the current as well as at least one preceding exercise of the user.

The adapting of the user plan data relating to the next exercise of the user can be based at least on the measure for the increase and/or the decrease of the heart-rate of the user during at least one of the current and the current as well as at least one preceding exercise of the user.

The user plan data can comprise data relating to the at least one next training resistance and wherein adapting of the user plan data can comprise adapting the data relating to the next training resistance based on the data relating to at least one of the current and the current as well as at least one preceding user exercise which data where respectively specified as suitable bases for adapting the data relating to the next training resistance(s).

In a fifth embodiment, a data-processing method is disclosed.

Advantages and definitions of terms discussed in the context of the training machine assembly, the system, the data-processing system and the method can apply respectively to the disclosed data-processing method. That is, also if certain terms, definitions and advantages are discussed again in the disclosure regarding the data-processing method, the advantages, terms and definitions disclosed with the training machine assembly, the system, the method and/or the data-processing system can be respectively applicable.

The data-processing method can comprise receiving data, sending data, and processing data.

The data-processing method can be a computer-implemented method. That is, the data-processing method can be performed by the data-processing system. In other words, the steps of the method can be performed by the data-processing system.

However, the method may comprise steps that can at least partially be performed by another system, for example an actuator in a training resistance which training resistance may be controlled by the data-processing system at least indirectly.

The consideration may for example also apply as regards sensing units, such as cameras or elements configured for heart-rate sensing.

At least some steps of the method can be performed by the data-processing system.

The data-processing method can comprise using the data-processing system.

The data-processing system can comprise the at least one end user computer device.

The end user computer device can be as discussed above.

The data-processing system can comprise the server system. In other words, the data-processing method can comprise using the data-processing system, which data-processing system can comprise the server system.

The data-processing method can comprise receiving the user plan data.

The data-processing method can comprise generating the user plan data.

The data-processing method can comprise storing the user plan data.

The user plan data can comprise data relating to the at least one user exercise, such as the next user exercise.

The user plan data can comprise data relating to a plurality of the user exercises.

The user plan data can comprise rule data for the user exercise(s), as discussed above.

The user plan data can comprise parameters for the user exercise(s), such as a corresponding training resistance value, a setting of a corresponding automatically adjustable user support element and/or an admissible range of motion during the user exercise.

The user plan data can comprise the target performance data.

The user plan data can comprise the target heart-rate data.

The target performance data can comprise the target heart-rate data.

The target heart-rate data can comprise the target range for the user heart-rate.

The user plan data can comprise the types of the user exercise(s).

The user plan data can comprise the indication of the suitable training machine assemblies for each user exercise.

The user plan data can comprise an indication of at least one order of the user exercise(s).

The user plan data can comprise the data relating to the training resistance for at least one exercise.

The user plan data can comprise the data relating to the training resistances for a plurality of exercises.

The data-processing method can comprise processing the instruction data.

The data-processing method can comprise generating the instruction data as discussed above. As discussed above, generating the instruction data can comprise selecting instruction data elements from a set of instruction data elements.

Generating the instruction data can comprise selecting the instruction data from a set of instruction data. The set of the instruction data can comprise the set of the instruction data elements. The set of the instruction data can comprise a database.

The data-processing method can comprise outputting the instruction data. That is, the data-processing method can for example comprise outputting elements of the instruction data, instructing the user to adapt his/her way of exercising and/or to start/stop exercising.

The data-processing method can comprise sending the instruction data. In other words, the data-processing method can comprise transmitting the instruction data. The sending can be on demand, for example in case of a download. The sending can also be "push-sending", that is, without prior request by the receiver.

The data-processing method can comprise generating the instruction data based on the user plan data.

The instruction data can comprise at least the indication relating to the training resistance for an exercise.

The instruction data can comprise at least the indication relating to the training resistances for a plurality of exercises.

The data-processing method can comprise controlling at least one training resistance of the at least one training machine assembly.

The at least one training machine assembly can be according to any aspect of the disclosed training machine assembly. In other words, the at least one training machine assembly can comprise any of the features disclosed in the disclosure of the training machine assembly.

The at least one training machine assembly can be a plurality of training machine assemblies.

The at least one training resistance can be a plurality of training resistances.

The data-processing method can comprise controlling the at least one training resistance based on the user plan data. The controlling can comprise a step that is performed by the control device of the training machine assembly. The controlling may comprise an operation of an actuator.

Controlling the at least one training resistance can be based on the instruction data.

In other words, the data-processing method can comprise controlling the at least one training resistance based on the instruction data.

The data-processing method can comprise controlling the at least one training machine assembly by sending data to the at least one training machine assembly by the data-processing system. That is, the method can comprise sending said data from the data-processing system to the at least one training machine assembly and thus controlling said at least one training machine assembly.

The data-processing method can comprise controlling the at least one training machine assembly by sending data to the at least one training machine assembly by the server system. In other words, the method can comprise sending data to the at least one training machine assembly from the server system and thus controlling the at least one training machine assembly.

The data-processing method can comprise controlling the at least one training machine assembly by sending data to the at least one training machine assembly by the at least one end user computer device. That is, the method can comprise sending data to the at least one training machine assembly from the at least one end user computer device and thus controlling the at least one training machine assembly.

The data-processing method can comprise storing the heart-rate data of the at least one user.

The data-processing method can comprise processing the heart-rate data of the at least one user.

The data-processing method can comprise generating the heart-rate data of the at least one user. For example, the method can comprise processing sensing inputs from a unit configured to sense the heart-rate of the at least one user.

The data-processing method can comprise storing the heart-rate variability data of the at least one user.

The data-processing method can comprise processing the heart-rate variability data of the at least one user.

The data-processing method can comprise generating the heart-rate variability data of the at least one user. For example, the method can comprise generating said heart-rate variability data from the heart-rate data or from measurements of the pulse of the user.

The data-processing method can comprise determining the temporal changes of the heart rate of the user.

The data-processing method can comprise processing the temporal changes of the heart rate of the user.

The data-processing method can comprise determining the measure for the increase or decrease of the heart-rate of the user. Said measure can be as discussed above.

The method can comprise processing the measure for the increase and/or decrease of the heart-rate of the user.

The data-processing method can comprise generating and/or receiving the image data of the at least one user. The data-processing method can comprise using the at least one camera for generating the image data.

The data-processing method can comprise generating and/or receiving the skeleton data of the at least one user. Generating the skeleton data can be performed as discussed above.

The data-processing method can comprise generating and/or receiving the skeleton-trajectory data of the at least one user. Generating the skeleton-trajectory data can be performed as discussed above.

The data-processing method can comprise generating the skeleton data of the user based on the image data of the user.

The data-processing method can comprise generating the skeleton-trajectory data of the user based on the image data of the user.

The data-processing method can comprise generating the heart-rate data of the user based on the image data of the user.

The data-processing method can comprise using the at least one boundary condition for generating the skeleton data of the user. The at least one boundary condition can be corresponding to the exercise of the user. The at least one boundary condition can also be corresponding to the training machine assembly that the user uses.

The data-processing method can comprise using at least one boundary condition for generating the skeleton-trajectory data of the user. The at least one boundary condition can be corresponding to the exercise of the user. The at least one boundary condition can also refer to the training machine assembly that the user uses.

The data-processing method can comprise using at least one boundary condition corresponding to the exercise of the user for generating the heart-rate data of the user.

At least one boundary condition can relate to the training machine assembly used to perform the user exercise.

At least one boundary condition can relate to possible positions of at least one part of the body of the user using the training machine assembly.

At least one boundary condition can relate to possible trajectories of movable parts of the respective training machine assembly. The respective training machine assembly can be the training machine assembly that the user uses and/or on which the user sits at a position where the image data are generated.

At least one boundary condition can relate to possible trajectories of at least parts of the body of the user interacting with the respective training machine assembly.

The data-processing method can comprise processing the performance data.

The data-processing method can comprise storing the performance data.

The data-processing method can comprise generating the performance data.

The data-processing method can comprise generating the performance data for the at least one user based at least on the heart-rate data of the at least one user.

The data-processing method can comprise generating the performance data for the at least one user based at least on the heart-rate variability data of the at least one user.

The data-processing method can comprise generating the performance data for the at least one user based at least on the heart-rate reference data of the at least one user.

The data-processing method can comprise generating the performance data for the at least one user based furthermore on comparing the heart-rate data and the heart-rate reference data of the user.

The data-processing method can comprise generating the performance data for the at least one user based at least on the skeleton data of the at least one user.

The data-processing method can comprise processing the history data.

The data-processing method can comprise receiving the history data.

The data-processing method can comprise generating the history data.

The data-processing method can comprises storing the history data.

The history data can relate to a plurality of users. That is, the history data can comprise information relating to each of the plurality of the users.

The history-data can comprise data relating to the training resistances.

The history-data can comprise data relating to the at least one training resistance for at least one exercise. The history data can also comprise data relating to the training resistances for a plurality of exercises.

The history-data can comprise heart-rate data. In other words, the history-data can comprise the heart-rate data or at least a portion thereof.

The history-data can comprise heart-rate variability data. That is, the history data can comprise the heart-rate variability data or at least a portion thereof.

The history-data can comprise data relating to the temporal changes of the heart rate of the user, as discussed above. The history-data can also comprise data relating to the measure for the increase and/or decrease of the heart-rate of the user, as discussed above. The history-data can also only comprise a portion of said data.

The history-data can comprise instruction data. In other words, the history-data can comprise the instruction data or at least a portion thereof.

The history-data can comprise skeleton data. That is, the history-data can comprise the skeleton data or at least a portion thereof.

The history-data can comprise skeleton-trajectory data. In other words, the history-data can comprise the instruction or at least a portion thereof.

The history-data can comprise performance data. That is, the history-data can comprise the performance data or at least a portion thereof.

The data-processing method can comprise receiving the reference data.

The data-processing method can comprise processing the reference data.

The data-processing method can comprise generating the reference data.

The data-processing method can comprise storing the reference data.

The data-processing method can comprise generating the comparison data. The method can also comprise generating at least a portion of the comparison data.

The data-processing method can comprise storing the comparison data.

The data-processing method can comprise processing the comparison data.

The data-processing method can comprise receiving the comparison data.

The data-processing method can comprise generating the comparison data by comparing data relating to the user to reference data.

The reference data can comprise skeleton-reference data. In other words, the reference data can comprise the skeleton-reference data or at least a portion thereof.

The comparison data can comprise the skeleton-comparison data. The data-processing method can comprise generating the skeleton-comparison data. The data-processing method can comprise generating the skeleton-comparison data by comparing the skeleton data to the skeleton reference-data.

The comparison data can comprise the trajectory-comparison data. The method can comprise generating the trajectory-comparison data. The method can comprise generating the trajectory-comparison data by comparing the skeleton-trajectory data to the skeleton reference-data.

The reference data can comprise the heart-rate reference data.

The comparison data can comprise the heart-rate comparison data. The data-processing method can comprise generating the heart-rate comparison data. The method can comprise generating the heart-rate comparison data by comparing the heart-rate data to the heart-rate reference data.

The data-processing method can comprises adapting the user plan data.

The data-processing system can adapt the user plan data. In other words, the method can comprise adapting the user plan data by the data-processing system.

The server system can adapt the user plan data. That is, the method can comprise adapting the user plan data by the server system.

The data-processing method can comprise adapting the user plan data based on the heart-rate data. Particularly, the method can comprise adapting the user plan data of a single user based on the heart-rate data relating to the respective user.

The data-processing method can comprise adapting the user plan data based on the heart-rate variability data. The method can comprise adapting the user plan data of a single user based on the heart-rate variability data relating to the respective user.

The data-processing method can comprise adapting the user plan data based on the temporal changes of the heart rate of the user. That is, the method can comprise adapting the user plan data corresponding to a specific user based on the temporal changes of the heart rate of said user.

The data-processing method can comprise adapting the user plan data based on the measure for the increase or decrease of the heart-rate of the user. In other words, the method can comprise adapting the user plan data corresponding to a specific user based on the measure for the increase or decrease of the heart-rate of the respective user.

The method can comprise adapting the user plan data based on the skeleton data.

That is, the method can comprise adapting the user plan data corresponding to a specific user based on the skeleton data relating to the respective user.

The data-processing method can comprise adapting the user plan data based on the skeleton-trajectory data. In other words, the data-processing method can comprise adapting the user plan data corresponding to a specific user based on the skeleton-trajectory data relating to the respective user.

The data-processing method can comprise adapting the user plan data based on the performance data. That is, the method can comprise adapting the user plan data corresponding to a specific user based on the performance data relating to said specific user.

The data-processing method can comprise adapting the user plan data based on the target performance data.

The data-processing method can comprise adapting the user plan data based on the history data.

The data-processing method can comprise controlling the at least one training resistance based on the adapted user plan data.

The data-processing method can comprise controlling the at least one training resistance based on the adapted user plan data corresponding to a specific user when the respective user interacts with the training machine assembly comprising the respective at least one training resistance.

The data-processing method can comprise controlling the at least one training resistance based on the comparison data.

The data-processing method can comprise adapting the instruction data based on the adapted user plan data.

The data-processing method can comprise adapting the instruction data based on the comparison data.

The data-processing method can comprise adapting the instruction data based on the history data. The data-processing method can also comprise adapting the user plan data based on the history data.

The data-process system can adapt the instruction data and/or the user plan data based on the history data. In other words, the data-processing method can comprise adapting at least one of the instruction data and the user plan data based on the history data by means of the data-processing system.

The data-processing method can comprise applying at least one machine learning algorithm to the history data, as discussed above.

The data-processing system can apply the at least one machine learning algorithm to the history data, as discussed above. In other words, the method can comprise applying the machine learning algorithm to the history data by the data-processing system.

The data-processing method can comprise applying at least one pattern recognition algorithm to the history data.

The data-processing method can comprise applying the at least one pattern recognition algorithm to the history data by the data-processing system applies. In other words, the data-processing system can apply the at least one pattern recognition algorithm to the history data.

The method can comprise applying the at least one reinforcement-learning algorithm to the history data.

The data-processing system can apply the at least one reinforcement-learning algorithm to the history data. In other words, the method can comprise applying the at least one reinforcement-learning algorithm to the history data by the data-processing system.

The data-processing method can comprise applying at least one neural-network algorithm to the history data.

The data-processing system can apply the at least one neural-network algorithm to the history data. That is, the method can comprise applying the at least one neural network algorithm to the history data by the data-processing system.

The data-processing method can comprise connecting the data-processing system to the at least one heart-rate sensing device.

The data-processing method can comprise connecting the at least one end user computer device to the at least one heart-rate sensing device.

The data-processing method can comprise connecting the server system to the at least one heart-rate sensing device.

The data-processing system can comprise the at least one heart-rate sensing device.

In other words, the data-processing method can comprise using the data-processing system, which can comprise the at least one heart-rate sensing device.

The at least one end user computer device can comprise the at least one heart-rate sensing device.

The at least one heart-rate sensing devices can be a plurality of heart-rate sensing devices.

At least one of the at least one end user computer device can comprise one of the at least one heart-rate sensing device.

The at least one end user computer device can be the plurality of end user computer devices, the at least one heart-rate sensing device can be the plurality of heart-rate sensing devices and further, and some of the end user computer devices can respectively comprise one of the heart-rate sensing devices. The method can respectively comprise using these pluralities of end user computer devices and heart-rate sensing devices.

Each of the at least one end user computer device can comprise a heart-rate sensing device. That is, each of the at least one end user computer device can comprise on the at least one heart-rate sensing device.

The data-processing method can comprise sensing the heart rate of the at least one user.

The data-processing method can comprise sensing the heart rate of the at least one user by means of the data-processing system. For example, the method can comprise sensing the heart-rate of the at least one user by means of the at least one heart-rate sensing device.

The data-processing method can comprise sensing the heart rate of at least one user by means of the at least one end user computer device. For example, the method can comprise sensing the heart-rate of the at least one user by means of the heart-rate sensing device, which heart-rate sensing device the end user computer device can comprise.

The data-processing method can comprise sensing the heart-rate variability of the at least one user.

The data-processing method can comprise sensing the heart-rate variability of the at least one user by means of the data-processing system. For example, the method can comprise sensing the heart-rate variability by means of the at least one heart-rate sensing device which the data-processing system can comprise.

The data-processing method can comprise sensing the heart-rate variability of the at least one user by means of the at least one end user computer device. For example, the method can comprise sensing the heart-rate variability by means of the at least one heart-rate sensing device which the end user computer device can comprise.

The data-processing method can comprise sensing the heart-rate variability of the at least one user by means of the at least one heart-rate sensing device.

The data-processing method can comprise receiving data from the at least one wearable device.

The method comprises using the at least one wearable device.

The at least one wearable device can be a plurality of wearable devices.

Each of the at least one wearable device can comprise a heart-rate sensing device.

The data-processing method can comprise sensing the heart-rate of the at least one user by means of the at least one wearable device.

The data-processing method can comprise sensing the heart-rate variability of the at least one user by means of the at least one wearable device.

The at least one end user computer device can be portable.

The end user computer device can be a smart mobile device, such as a tablet computer, a smart phone or a smart watch.

The data-processing method can comprise sending data to a third system. The third system can be an external data-processing system. The third system can for example be a data-processing system associated with a health care provider. The third system can be a third-party data-processing system. It can just be another data-processing system.

The data-processing system can send the data to the third system. In other words, the method can comprise sending data to the third system by means of the data-processing system.

The data to be sent to the third system can comprise heart-rate data. In other words, the data-processing method can comprise sending all or at least a portion of the heart-rate data to the third system.

The data to be sent to the third system can comprise performance data. That is, the data-processing method can comprise sending all or at least a portion of the heart-rate data to the third system.

The data to be sent to the third system can comprise instruction data. That is, the data-processing method can comprise sending all or at least a portion of the instruction data to the third system.

The data to be sent to the third system can comprise data relating to the at least one training resistance. In other words, the data-processing method can comprise sending all or at least a portion of the data relating to the at least one training resistance.

The data to be sent to the third system can comprise performance data. That is, the data-processing method can comprise sending all or at least a portion of the performance data to the third-data processing system.

The data to be sent to the third system can comprise comparison data. In other words, the data-processing method can comprise sending all or at least a portion of the comparison data to the third data-processing system.

The data-processing method can comprise receiving data. That is, the method can comprise receiving data to be received.

The data-processing system can receive the data. In other words, the data-processing method can comprise receiving the data by the data-processing system.

The data to be received can comprise heart-rate data, that is, the data to be received can comprise the heart-rate data as described above, or at least a portion thereof.

The data to be received can comprise data relating to the at least one training resistance. In other words, the data to be received can comprise the data relating to the at least one training resistance as discussed above, or at least a portion thereof.

The data to be received can comprise heart-rate variability data. That is, the data to be received can comprise the heart-rate variability data as discussed above, or at least a portion thereof.

The data to be received can comprise history data. That is, the data to be received can comprise the history data as discussed above, or at least a portion thereof.

The data-processing method can comprise connecting the at least one training machine assembly to the data-processing system.

The data-processing method can comprise connecting the data-processing system to a system according any of the above-disclosed aspects of the system.

The at least one end user computer device can be the plurality of end user computer devices. In other words, the data-processing method can comprise using the plurality of end user computer devices.

The data-processing method can comprise processing data relating to a plurality of users. That is, where data-processing method steps are disclosed for single users or relating to single users, these steps can be performed a plurality of times, each time for a specific user, or they can be performed once for the plurality of users.

The data-processing method can comprise receiving the data relating to the plurality of users.

The data-processing method can comprise storing the data relating to the plurality of users.

The data-processing method can comprise generating data relating to a plurality of users.

That is, where at least one of the receiving, the storing and the generating of data is disclosed, the data can relate to a plurality of users. The person ordinarily skilled in the art will easily understand that however, the data can also relate to a single user.

The at least one user can be a plurality of users. The method can be performed for a plurality of users, as well as for a single user or at least one user.

The user plan data can comprise data relating to the training resistance for at least one respectively next exercise of the at least one user.

The user plan data can comprise data relating to the training resistances for the plurality of exercises, comprising the respectively next exercise of the at least one user.

The instruction data can comprise at least an indication relating to the training resistance for the at least one respectively next exercise of the at least one user.

The instruction data can comprise at least an indication relating to the training resistances for the plurality of exercises, comprising the respectively next exercise of the at least one user.

The method can comprise controlling the at least one training resistance of the at least one training machine assembly.

The method can comprise adapting the user plan data relating to the next exercise of the at least one user.

The method can comprise adapting the user plan data relating to the next exercise of the user based at least on the performance-deviation data relating to at least one of the current and the current as well as at least one preceding user exercise of the user.

The method can comprise adapting the user plan data relating to the next exercise of the user based at least on the heart-rate data relating to at least one of the current and the current as well as at least one preceding user exercise of the user.

The method can comprise adapting the user plan data relating to the next exercise of the user based at least on the heart-rate variability data relating to the period during the current and the next and/or the preceding and the current user exercise.

The method can comprise adapting the user plan data relating to the next exercise of the user based at least on the temporal changes of the heart rate of the user during at least one of the current and the current as well as at least one preceding user exercise of the user.

The method can comprise adapting the user plan data relating to the next exercise of the user based at least on the measure for the increase and/or the decrease of the heart-rate of the user during at least one of the current and the current as well as at least one preceding user exercise of the user.

Adapting of the user plan data can comprise adapting the data relating to the next training resistance based on the data relating to at least one of the current and the current as well as at least one preceding user exercise of the user, which data were above specified as suitable bases for such adapting.

In the following, some data and data types are described again and discussed in detail. Definitions, terms, disclosed features and advantages from the above disclosure can respectively apply. That is in particular, some of the above-discussed features may not be repeated below, even though they may apply.

Each of the at least one training resistance comprises at least one training resistance value.

The training resistance value can be for example a force applied towards the user contact element of the training resistance, e.g. a handle. The training resistance value can also comprise a function or a vector, for example a function linking a speed of movement of a user and/or a user contact element and a force and/or torque applied against said movement.

The training resistance value can also be a parameter for the training resistance.

Such a parameter can e.g. be a parameter used by the control device of the training machine assembly. Such a parameter can however also be an indication of position of a weight pin or element or control for adjusting the training resistance.

The data relating to the training resistance or to a training resistance of the training resistances can comprise the training resistance value.

The heart-rate data can comprise data relating to at least one of the pulse and the heart-rate of the user.

The heart-rate data can be stored as the frequency of heart-beats.

The heart-rate data can be stored as time intervals between the heart-beats or parts thereof, such as a length of the R-R interval.

However, the heart-rate data may also be stored differently.

The heart-rate data can be generated based on the image data of the user. However, the heart-rate data can also be sensed by a heart-rate sensing device, as discussed above.

The heart-rate data as well as the heart-rate of a single user can be an indicator for the training intensity during an exercise as well as the fitness of the user.

The heart-rate variability can be a variability of the length of the time interval between the single heart-beats of the user. It can be determined based on a variation in the length of the time intervals between the heart-beats of the user. The heart-rate variability can also be referred to as the "cycle length variability".

The heart-rate variability can be a measure for the general fitness of the user. The heart-rate variability can be determined when the user is not exercising.

The heart-rate variability can also be a measure for the fitness of the user on the training day.

The heart-rate variability data can comprise the heart-rate variability of the at least one user. The heart-rate variability data can also comprise an indicator of the heart-rate variability of the at least one user.

The heart-rate variability data can be derived from the heart-rate data of the user, if said heart-rate data of the user respectively sufficiently precise.

The heart-rate variability data can be indicated by different measures well-known in the art, for example the RMSSD ("Root Mean Square of Successive Differences"), wherein the successive differences are the differences of the length of two succeeding heartbeats. Other measures are directed to a standard deviation of the lengths of the lengths of the heartbeats, such as the SDNN ("Standard Deviation of the NN Interval"). There are also measures, for example in the frequency domain. An overview of possible measures can for example be found in Shaffer, F. & Ginsberg, J. P. (2017): "An Overview of Heart Rate Variability Metrics and Norms", in *Frontiers in Public Health,* 5:258, doi: 10.3389/fpubh.2017.00258

The image data can comprise a sequence of images. The sequence of images can be timestamped.

The image data can comprise an indication of a specific camera which camera captured them. The image data can for example comprise an indication of a training machine assembly which is associated with the respective camera. This can be the case if the camera is mounted to said training machine assembly. It can also be the case if the camera captures users using said training machine assembly.

This can be optionally advantageous for further processing of the data, for example for applying the at least one boundary condition, which boundary condition may be specific to a camera or a perspective of the camera.

The skeleton data can comprise data relating to the joint positions, the distances of joints and/or other anatomical features of the user, such as the length of body parts, the asymmetries and/or the potential injuries limiting the user's movements.

The skeleton data may be inferred and/or determined from the image data as discussed above.

The skeleton data may be inferred from a 2D-image and/or from data which leave at least one mathematical degree of freedom in a calculation of the skeleton data. In such cases, the degree of freedom may optionally be reduced and/or removed based on the at least one boundary condition.

The skeleton-trajectory data can comprise data relating to the position over time of joints and/or other parts of the body of the user. In other words, the skeleton-trajectory data can relate to the trajectory of parts, portions and/or features of the body of the user, such as joints, hands or shoulders.

The skeleton-trajectory data can be derived from the skeleton data. The skeleton-trajectory data can also be inferred and/or determined based on the image data. At least one of the at least one boundary condition can be applied as discussed above in the context of the skeleton data.

The comparison data can be generated by comparing at least one of reference data and predetermined data to corresponding data relating to the user.

The comparison data can comprise at least one of the heart-rate comparison data, the skeleton-comparison data, the trajectory-comparison data.

The heart-rate comparison data can be generated by at least comparing the heart-rate data of the user to the predetermined heart-rate data.

For example, the heart-rate comparison data can be generated by comparing the heart-rate of the user to an average resting pulse as well as an average maximum pulse of the user.

The predetermined heart-rate data can be user-specific.

Comparing the heart-rate data of the user to the predetermined heart-rate data can be optionally advantageous, as the heart-rate and its changes may be user-specific and a comparison result generated using user-specific predetermined data can be more reliable than a comparison with general predetermined heart-rate data.

The skeleton-comparison data can be generated by comparing the skeleton data to the skeleton-reference data.

The skeleton-reference data can for example indicate standard measures to which settings and/or data relate. Thus, the skeleton-comparison data can indicate a difference of the user to said standard measures and possible necessary adaptions of the settings and/or the data.

The skeleton-reference data can comprise a base for generating the skeleton-comparison data. They can for example comprise a measuring scheme, indicating which measures are to be generated. They can also comprise standard data to which the generated skeleton data can be compared. The skeleton-reference data can comprise software, e.g. a software portion for generating the skeleton-comparison data.

The trajectory-comparison data can be generated by comparing the skeleton-trajectory data to the skeleton-reference data.

The trajectory-comparison data can for example indicate a proper execution of an exercise by the user, and/or mistakes during the execution of the exercise, respectively. The trajectory-comparison data can indicate an execution of the exercise by the user which may lead to suboptimal training outcomes or even lead to injuries.

The generation of the trajectory-comparison data can be optionally advantageous as the trajectory-comparison data can allow for automated detection of suboptimal exercising and can further enable an automated reaction, such as an appropriate adaption of the at least one training resistance and/or an output of corresponding instruction data.

A portion of the skeleton-reference data relating to the skeleton trajectory can be adapted based on the skeleton-comparison data and/or the skeleton data. The result of the comparison can be adapted based on the skeleton-comparison data and/or the skeleton data.

For example, in a case where the trajectory-porting of the skeleton reference data are based on an exercise of a first user with known skeleton data, the adapting can be according to differences between the skeleton data of the first user to a current user. In such a case, the first user can for example be an experienced user and/or an instructor.

In another example, where the trajectory-portion of the skeleton-reference data trajectory-comparison data are generated by a simulation, the adapting can compensate for simulation parameters which may not correspond to the current user, as discussed above.

Also, in a further example, where the trajectory-portion of the skeleton-reference data are generated by the simulation, the simulation can be performed based on the skeleton-comparison data. An optional advantage can be improved skeleton-reference data.

The skeleton-reference data can further comprise a base for generating the trajectory-comparison data, such as the portion relating to the skeleton trajectory. Said portion can for example comprise data relating to an optimal trajectory of the above-mentioned portions of the body of the user during a specific exercise.

The portion of the skeleton-reference data can be specific to the user. The portion can be adapted to specific users respectively. The portion of the skeleton-reference data can also be non-specific. The portion can be adapted temporarily, for example during comparison, or the comparison can be adapted so as to compensate for the specific user.

The portion of the skeleton-reference data can for example be specific to the user due to a specific physiology of the user, such as the measures described by the skeleton data.

The skeleton-reference data can for example be adapted based on the skeleton data.

The user plan data can be user-specific. The user plan data can comprise data relating to at least one or a set of user exercises for the user. The user plan data can comprise an indication of the type of the types of the exercises for the user.

The user plan data can further comprise an order or at least a preferred order of the user exercises.

The user plan data can further comprise rule data. The rule data can for example comprise at least one rule regarding the order of the user exercise. Such a rule regarding the order of the user exercises can for example indicate that two exercises may not be executed directly after each other or that in such a case, the corresponding training resistance(s) must be adapted correspondingly.

The user plan data can comprise data relating to the at least one training resistance for the respective exercise.

The user plan data can comprise at least one or a plurality of parameters for the user exercises respectively, such as a corresponding training resistance value, a setting of a corresponding automatically adjustable user support element and/or an admissible range of motion during the respective user exercise.

The at least one or the plurality of the parameters can be user-specific.

The user plan data can comprise the target performance data.

The user plan data can comprise the indication of the suitable training machine assembly for respective exercises. The indication can be an indication of a suitable type of the training machine assembly.

For example, the user plan data can comprise an indication of an optimal type of the training machine assembly for an exercise, and an indication of an alternative type of training machine assembly in cases where the user exercise can also be performed at training machine assemblies of another type.

An optional advantage of using the user plan data can be that the user plan data allow for a flexible adjustment of a training of the user, for example in response to available training machine assemblies and/or a fitness of the user.

The activity data can relate to the activity level of the user.

For example, the activity data can indicate whether a user is exercising, resting, or performing another activity, such as moving from one training machine assembly to another in case of a circuit training.

The instruction data can comprise data relating to a further exercise of the user, such as the next exercise and/or at least one or a plurality of possible training machine assemblies for the next exercise.

The instruction data can comprise portion corresponding to certain parts of the comparison data respectively, such as an instruction regarding proper execution of the user exercise when the trajectory-comparison data indicate that the user does not properly execute the user exercise.

The instruction data can comprise instructions regarding an activity of the user, for example an instruction to start and to stop an exercise in the context of a circuit training.

The instruction data can comprise instructions regarding an execution of an exercise.

The instructions regarding the execution of the exercise can be specific to a type of training machine assemblies. This can be optionally advantageous in a case where at least two different types of training machine assemblies can be used for the exercise, since the instructions can then be more specific.

The performance data can be an indicator for the performance and/or a readiness for performance of the user.

An optional advantage can be that the performance data can allow for an automated adjustment of the training resistance in order to provide an optimal training effect, particularly to avoid an overly high training resistance in a situation where the user cannot provide the corresponding effort.

As discussed above, the performance data can be generated based on different data.

That is, the performance and or the readiness for performance of the user can be determined based on different data. The data based on which the performance data can be generated can for example comprise at least one of the heart-rate data, the heart-rate variability data, the heart-rate reference data, the skeleton data, the skeleton-trajectory data, the training-resistance value(s) of training machine assemblies with which the user interacts and the activity data.

The performance-deviation data can be generated by identifying the deviation in the performance data relating to the user.

In other words, the performance-deviation data can comprise data relating to the deviation in the performance data corresponding to a single user. For example, the performance-deviation data can indicate a higher or lower readiness to exercise of the user.

The performance-deviation data can for example also be a measure for the exhaustion level of the user.

Below, training machine assembly embodiments will be discussed. These embodiments are abbreviated by the letter "T" followed by a number. Whenever reference is herein made to "training machine assembly embodiments", these embodiments are meant.

T1 A training machine assembly (10), comprising
(i) at least one control device (30), and
(ii) at least one training resistance (14), wherein each training resistance comprises at least one training resistance value.

T2 The training machine assembly (10) according to the preceding embodiment, further comprising at least one camera (20).

T3 The training machine assembly (10) according to any of the preceding training-machine embodiments,
wherein the at least one training resistance is automatically adjustable and the training machine assembly (10) is configured to adjust the at least one training resistance.

T4 The training machine assembly (10) according to any of the preceding training-machine embodiments,
wherein the training machine assembly (10) comprises at least one automatically adjustable user support element (16).

T5 The training machine assembly (10) according to any of the preceding training-machine embodiments, wherein the training machine assembly (10) comprises a heart-rate detection component.

T6 The training machine assembly (10) according to any of the preceding training-machine embodiments, wherein the training machine assembly (10) is configured to be connected to a heart-rate sensing device.

T7 The training machine assembly (10) according to the preceding training machine assembly embodiment, wherein the heart-rate sensing device is configured to sense the heart-rate of the user when in physical contact to the user.

T8 The training machine assembly (10) according to the preceding training machine assembly embodiment, wherein the heart-rate sensing device is portable and configured to be worn by the user.

T9 The training machine assembly (10) according to any of the three preceding training machine assembly embodiments, wherein the heart-rate sensing device can be at least one of a smart watch, a bracelet or another wearable fitness tracker device configured for heart-rate sensing.

T10 The training machine assembly (10) according to any of the preceding training machine assembly embodiments with the features of T5, wherein the heart-rate detection component is mounted to the training machine assembly.

T11 The training machine assembly (10) according to any of the preceding training machine assembly embodiments with the features of T5, wherein the heart-rate detection component is configured to be touched by the user.

T12 The training machine assembly (10) according to any of the preceding training machine assembly embodiments with the features of T5, wherein the heart-rate detection component is configured to for sensing the heart-rate of the user.

T13 The training machine assembly (10) according to any of the preceding training machine assembly embodiments with the features of T5, wherein the heart-rate detection component is configured to for sensing a heart-rate variability of the user.

T14 The training machine assembly (10) according to any of the preceding training-machine assembly embodiments, wherein the training machine assembly is configured for generating heart-rate data of the user.

T15 The training machine assembly (10) according to any of the preceding training machine assembly embodiments with the features of T5, wherein the training machine assembly (10) is configured for generating the heart-rate data of the user by means of the heart-rate detection component.

T16 The training machine assembly (10) according to any of the preceding training-machine embodiments with the features of T2, wherein the training machine assembly is configured for generating the heart-rate data of a user based on image data captured by the at least one camera (20).

T17 The training machine assembly (10) according to the preceding training-machine embodiment, wherein the training machine assembly is configured for generating the heart-rate data of the user based on the image data, wherein the image data comprise a sequence of images.

T18 The training machine assembly (10) according to any of the two preceding training-machine embodiments, wherein the training machine assembly is configured for generating the heart-rate data of the user based on the image data, wherein the image data comprise a timestamped sequence of images.

T19 The training machine assembly (10) according to any of the preceding training-machine embodiments with the features of T2, wherein the training machine assembly is configured for generating the heart-rate data of the user based on video data captured by the camera (20).

T20 The training machine assembly (10) according to any of the preceding four embodiments, wherein the image data are captured with a frequency of at least 6.67 Hz.

T21 The training machine assembly (10) according to any of the preceding five embodiments, wherein the image data are captured with a frequency of at least 7.4 Hz.

T22 The training machine assembly (10) according to any of the preceding training-machine embodiments with the features of T2, wherein the training machine assembly is configured for generating skeleton data of the user based on the image data captured by the at least one camera (20).

T23 The training machine assembly (10) according to any of the preceding training-machine embodiments with the features of T2, wherein the training machine assembly is configured for generating skeleton-trajectory data of the user based on image data captured by the at least one camera (20).

T24 The training machine assembly according to any of preceding embodiments with the features of at least one of T16, T22 and/or T23, wherein the training machine assembly is configured for generating at least one of the heart-rate data, the skeleton data and the skeleton-trajectory data, and for using at least one or a plurality of boundary condition(s) corresponding to a geometry of the training machine assembly.

T25 The training machine assembly according to the preceding embodiment, wherein at least one of the boundary condition(s) is at least one possible position of at least one part of the body of the user.

T26 The training machine assembly according to any of the two preceding embodiments, wherein at least one of the boundary condition(s) is at least one or a plurality of possible trajectories of movable parts of the training machine assembly.

T27 The training machine assembly according to any of the three preceding embodiments, wherein at least one of the boundary conditions are at least one or a plurality of possible trajectories of at least parts of the body of the user interacting with the training machine assembly.

T28 The training machine assembly (10) according to any of the preceding training-machine embodiments, wherein the training machine assembly (10) comprises a supplementary sensing unit.

T29 The training machine assembly (10) according to any of the preceding training-machine embodiments, wherein each of the at least one training resistance is configured for sensing a user's training effort.

T30 The training machine assembly (10) according to the preceding embodiment, wherein each of the at least one training resistance comprises a sensing unit that is configured for sensing the user's training effort.

T31 The training machine assembly (10) according to any of the preceding embodiments with the features of T2, wherein the training machine assembly (10) comprises not more than one camera.

T32 The training machine assembly (10) according to any of the preceding embodiments with the features of T2, wherein the at least one camera is at least one 2D-camera.

T33 The training machine assembly (10) according to any of the preceding embodiments with the features of T2, wherein the at least one camera is at least one 3D-camera.

T34 The training machine assembly (10) according to any of the preceding embodiments with the features of T2, wherein the at least one camera is a set of at least one 2D-camera and at least one 3D-camera.

T35 The training machine assembly (10) according to any of the preceding training machine assembly embodiments with the features of at least one of T32, T33 and/or T34, wherein at least one of the at least one 2D-camera is configured for sensing light in a visible spectrum.

T36 The training machine assembly (10) according to any of the preceding training machine assembly embodiments with the features of at least one of T32, T33 and/or T34, wherein the at least one of the at least one 3D-camera comprises a projected infrared depth camera.

T37 The training machine assembly (10) according to any of the preceding training machine assembly embodiments with the features of at least one of T32, T33 and/or T34, wherein the at least one of the at least one 3D-camera comprises a time-of-flight depth camera.

T38 The training machine assembly (10) according to any of the preceding training machine assembly embodiments with the features of T2, wherein the training machine assembly (10) is configured for combining data of the at least one camera.

T39 The training machine assembly (10) according to any of the preceding training machine embodiments with the features of T34, wherein the training machine assembly (10) is configured for combining data of the at least one 2D-camera and the at least one 3D-camera.

T40 The training machine assembly (10) according to any of the preceding embodiments,
wherein the training machine assembly (10) comprises a user interface that is configured for outputting data.

T41 The training machine assembly (10) according to any of the preceding embodiments with the features of T14,
wherein the training machine assembly (10) is configured for storing and/or transmitting the heart-rate data of the user.

T42 The training machine assembly (10) according to any of the preceding embodiments with the features of T14,
wherein the training machine assembly (10) is configured for comparing the heart-rate data of the user to predetermined heart-rate data.

T43 The training machine assembly (10) according to any of the preceding embodiments with the features of T14,
wherein the training machine assembly (10) is configured for comparing the heart-rate data of the user to at least one of the at least one training resistance value.

T44 The training machine assembly (10) according to any of the preceding embodiments with the features of T14,
wherein the training machine assembly (10) is configured for comparing the heart-rate data of the user corresponding to different activity levels of the user.

T45 The training machine assembly (10) according to any of the preceding embodiments with the feature of T14,
wherein the training machine assembly (10) is configured for generating heart-rate comparison data by at least one of
comparing the heart-rate data of the user to the predetermined heart-rate data,
comparing the heart-rate data of the user corresponding to different activity levels of the user, and
comparing the heart-rate data of the user to at least one of the at least one training resistance value.

T46 The training machine assembly (10) according to any of the preceding embodiments with the features of T14,
wherein the training machine assembly (10) is configured for generating the heart-rate comparison data by determining the heart-rate variability.

T47 The training machine assembly (10) according to any of the preceding embodiments with the features of T14,
wherein the training machine assembly (10) is configured for determining the heart-rate variability based on the heart-rate data.

T48 The training machine assembly (10) according to any of the preceding embodiments with the features of T14,
wherein the heart-rate comparison data comprise heart-rate variability data.

T49 The training machine assembly (10) according to any of the preceding embodiments with the features of T22,
wherein the training machine assembly (10) is configured for comparing the skeleton data to skeleton-reference data and to thus generating skeleton-comparison data.

T50 The training machine assembly (10) according to any of the preceding embodiments with the features of T23,
wherein the training machine assembly (10) is configured for comparing the skeleton-trajectory data to skeleton-reference data and to thus generating trajectory-comparison data.

T51 The training machine assembly (10) according to the preceding embodiment, wherein the training machine assembly (10) is configured for comparing the skeleton-trajectory data to skeleton-reference data and adapting the skeleton-reference data; and to thus generating trajectory-comparison data.

T52 The training machine assembly (10) according to the preceding embodiment, wherein adapting the skeleton-reference data is based at least one the skeleton data.

T53 The training machine assembly (10) according to any of the preceding embodiments,
wherein the training machine assembly (10) is configured to transmit at least one of the heart-rate comparison data, the skeleton-comparison data and the trajectory-comparison data.

T54 The training machine assembly according to the preceding embodiment,
wherein the training machine assembly (10) is configured to transmit said data to a data-processing system.

T55 The training machine assembly according to any of the preceding two embodiments,
wherein the training machine assembly (10) is configured to transmit said data to an end user computer device.

T56 The training machine assembly according to the preceding embodiment, wherein the end user computer device is a portable end user computer device.

T57 The training machine assembly according to any of the preceding embodiments with the features of T53, wherein the training machine assembly (10) is configured to transmit said data to a server system.

T58 The training machine assembly according to any of the preceding embodiments with the features of T53, wherein the training machine assembly (10) is configured to transmit said data to at least one or a plurality of further training machine assemblies.

T59 The training machine assembly (10) according to any of the preceding embodiments,
wherein the training machine assembly (10) is configured to receive at least one of the heart-rate comparison data, the skeleton-comparison data and the trajectory-comparison data.

T60 The training machine assembly according to the preceding embodiment,
wherein the training machine assembly (10) is configured to receive said data from the data-processing system.

T61 The training machine assembly according to any of the two preceding embodiments,
wherein the training machine assembly (10) is configured to receive said data from the at least one or a plurality of further training machine assemblies.

T62 The training machine assembly (10) according to any of the preceding embodiments,
wherein the training machine assembly (10) is configured for adjusting at least one of the at least one automatically adjustable user support element based on at least one of the skeleton-comparison data and the trajectory-comparison data.

T63 The training machine assembly according to any of the preceding embodiments with the features of T49 and/or T50, wherein the training machine assembly (10) is configured for adjusting at least one of the at least one training resistance based on at least one of the skeleton-comparison data and the trajectory-comparison data.

T64 The training machine assembly (10) according to any of the preceding embodiments with the features of T40 and at least one of T49 and T50,
wherein the training machine assembly (10) is configured for outputting data via the user interface based on at least one of the skeleton-comparison data and the trajectory-comparison data.

T65 The training machine assembly (10) according to any of the preceding embodiments with the features of T40 and T45,
wherein the training machine assembly (10) is configured for outputting data via the user interface based on the heart-rate comparison data.

T66 The training machine assembly (10) according to any of the preceding embodiments,
wherein the training machine assembly (10) is configured for receiving user plan data.

T67 The training machine assembly (10) according to the preceding embodiment,
wherein the training machine assembly (10) is configured for adjusting the training resistance based on the user plan data.

T68 The training machine assembly (10) according to any of the preceding embodiments,
wherein the training machine assembly (10) is a strength training machine assembly (10).

T69 The training machine assembly (10) according to any of the preceding embodiments,
wherein the training machine assembly (10) is configured for user identification.

T70 The training machine assembly (10) according to the preceding embodiment,
wherein the training machine assembly is configured for user identification by a user identification device.

T71 The training machine assembly (10) according to any of the two preceding embodiments with the features of T2,
wherein the training machine assembly is configured for user identification by facial recognition.

T72 The training machine assembly (10) according to any of the preceding embodiments with the features of T2, wherein the camera (20) is mounted to the control device.

T73 The training machine assembly (10) according to any of the preceding embodiments,
wherein the camera (20) is connected to the control device via a wired connection.

T74 The training machine assembly (10) according to any of the preceding embodiments,
wherein the camera (20) is connected to the control device via a wireless connection.

T75 The training machine assembly (10) according to any of the preceding embodiments with the features of at least one of T12 and T14, wherein the training machine assembly (10) is configured to adjust the at least one training resistance based on the heart-rate of the user.

T76 The training machine assembly (10) according to any of the preceding embodiments with the features of at least one of T13 and T14, wherein the training machine assembly (10) is configured to adjust the at least one training resistance based on the heart-rate variability of the user.

T77 The training machine assembly (10) according to any of the preceding embodiments,
wherein the training machine assembly (10) is configured to receive data indicating the heart-rate of the user and to adjust the at least one training resistance based on the data indicating the heart-rate of the user.

T78 The training machine assembly (10) according to any of the preceding embodiments,
wherein the training machine assembly (10) is configured to receive data indicating the heart-rate variability of the user and to adjust the at least one training resistance based on the data indicating the heart-rate variability of the user.

T79 The training machine assembly (10) according to any of the preceding embodiments with the features of T67,
wherein the training machine assembly (10) is configured for adjusting the training resistance based on the user plan data which user plan data were updated at a preceding exercise of the user.

T80 The training machine assembly (10) according to any of the preceding embodiments with the features T75, wherein the training machine assembly (10) is configured to adjust the at least one training resistance based on the heart-rate of the user during at least one of the preceding exercise of the user and a time between the preceding exercise of the user and a current exercise at the training machine assembly (10).

T81 The training machine assembly (10) according to any of the preceding embodiments with the features of T76, wherein the training machine assembly (10) is configured to adjust the at least one training resistance based on the heart-rate variability of the user before the current exercise at the training machine assembly (10).

T82 The training machine assembly (10) according to any of the preceding embodiments with the features of T77, wherein the training machine assembly (10) is configured to receive data indicating the heart-rate of the user at least at the preceding exercise of the user and to adjust the at least one training resistance based on the data indicating the heart-rate of the user.

Below, system embodiments will be discussed. These embodiments are abbreviated by the letter "S" followed by a number. Whenever reference is herein made to "system embodiments", these embodiments are meant.

S1 A system, comprising at least one or a plurality of training machine assemblies (10), each of the training machine assemblies comprising at least one training resistance, wherein each training resistance comprises at least one training resistance value.

S2 The system according to the preceding embodiment, wherein a plurality of the training machine assemblies (10) are according to any of the training machine assembly embodiments.

S3 The system according to any of the two preceding embodiments, wherein all training machine assemblies (10) are according to any of the training machine assembly embodiments.

S4 The system according to any of the preceding system embodiments, wherein the system comprises a communication network that is configured to enable data transmission between a plurality of the training machine assemblies (10) of the system.

S5 The system according to the preceding system embodiment, wherein the communication network is configured to enable data transmission between all training machine assemblies (10) of the system.

S6 The system according to any of the preceding system embodiments, wherein the system is configured for data transmission to the server system.

S7 The system according to any of the preceding system embodiments, wherein the system is configured for receiving data from the server system.

S8 The system according to any of the preceding system embodiments, wherein the system comprises a data processing system (32).

S9 The system according to any of the preceding system embodiments with the features of S8, wherein the data processing system is configured for storing user data.

S10 The system according to any of the preceding system embodiments with the features of S8, wherein the data-processing system comprises a plurality of devices that are portable.

S11 The system according to any of the preceding system embodiments with the features of S8, wherein the data-processing system comprises a plurality of data-devices that are configured to be worn, carried and/or hold the by users.

S12 The system according to the preceding system embodiment, wherein the data-devices are configured for identification of a user.

S13 The system according to any of the preceding embodiments with the features of S11, wherein the data-devices are configured for data storage.

S14 The system according to any of the preceding embodiments with the features of S11, wherein the data-devices are configured for data transmission to another portion of the system.

S15 The system according to any of the preceding embodiments with the features of S11, wherein the system is configured for storing user data on the data-devices.

S16 The system according to any of the preceding embodiments with the features of S11, wherein the data-devices are configured for receiving data from another portion of the system.

S17 The system according to any of the preceding embodiments with the features of S11, wherein the data-devices comprise a transmission element configured for wired communication.

S18 The system according to any of the preceding embodiments with the features of S11, wherein the data-devices comprise a transmission element configured for wireless communication.

S19 The system according to any of the preceding system embodiments, wherein the system comprises at least one camera.

S20 The system according to the preceding system embodiment, wherein the at least one camera is a 2D-camera.

S21 The system according to the preceding system embodiment, wherein the system does not comprise more cameras than training machine assemblies (10).

S22 The system according to any of the preceding system embodiments with the features of S19, wherein the at least one camera is at least one 2D-camera.

S23 The system according to any of the preceding system embodiments with the features of S19, wherein the at least one camera is at least one 3D-camera.

S24 The system according to any of the preceding system embodiments with the features of S19, wherein the at least one camera is a set of at least one 3D-camera and at least one 2D-camera.

S25 The system according to any of the preceding system embodiments with the features of S19, wherein the at least one camera is a set of at least one 3D-camera and a plurality of 2D-cameras.

S26 The system according to any of the preceding system embodiments with the features of S19, wherein the at least one camera is a set of a plurality of 3D-cameras and a plurality of 2D-cameras.

S27 The system according to any of the preceding system embodiments with the features of at least one of S22, S23 and/or S24, wherein at least one of the at least one 3D-camera is a time-of-flight depth camera.

S28 The system according to any of the preceding system embodiments with the features of at least one of S22, S23 and/or S24, wherein at least one of the at least one 3D-camera is a projected infrared depth camera.

S29 The system according to any of the preceding system embodiments with the features of at least one of S22, S23 and/or S24, wherein at least one of the at least one 2D-camera is configured for sensing light in the visible spectrum.

S30 The system according to any of the preceding system embodiments with the features of at least one of S22, S23 and/or S24, wherein at least one of the at least one 2D-camera is configured for sensing light in the infrared spectrum.

S31 The system according to any of the preceding system embodiments with the features of at least one of S22, S23 and/or S24, wherein at least one of the at least one 2D-camera is configured for sensing a reflection of ultrasonic waves and wherein the system comprises a source of ultrasonic waves.

S32 The system according to any of the preceding system embodiments with the features of at least one of S22, S23 and/or S24, wherein at least one of the at least one 2D-camera is configured for sensing a reflection of radar and wherein the system comprises a radar sender.

S33 The system according to any of the preceding system embodiments with the features of at least one of S22, S23 and/or S24, wherein at least one of the at least one 2D-camera is configured for sensing a reflection of laser light and wherein the system comprises a source of laser light.

S34 The system according to any of the system embodiments with the features of S19, wherein a plurality or all of the training machine assemblies are according to T31.

S35 The system according to any of the preceding system embodiments, wherein the system is configured for generating heart-rate data of the user.

S36 The system according to any of the preceding system embodiments with the features of S35, wherein the heart-rate data comprise heart-rate variability data.

S37 The system according to the preceding system embodiment, wherein a plurality of training machine assemblies (10) of the system are according to any of the training machine assembly embodiments with the features of T13.

S38 The system according to any of the two preceding embodiments, wherein a plurality of training machine assemblies (10) of the system are according to any of the training machine assembly embodiments with the features of T4.

S39 The system according to any of the preceding system embodiments with the features of S35, wherein the system is configured for generating the heart-rate data of the user based on image data captured by at least one of the cameras (20).

S40 The system according to the preceding system embodiment, wherein the training machine assembly is configured for generating the heart-rate data of the user based on timestamped image data.

S41 The system according to the preceding system embodiment, wherein the system is configured for generating the heart-rate data of the user based on video data captured by the at least one camera (20).

S42 The system according to any of the preceding system embodiments with the features of S35, wherein the system comprises a plurality of heart-rate sensing devices.

S43 The system according to the preceding system embodiment, wherein the heart-rate sensing devices are configured to generate heart-rate data when in physical contact to the user.

S44 The system according to any of the preceding system embodiments with the features of S42, wherein of a plurality of the training machine assemblies, each one comprises at least one of the heart-rate sensing devices.

S45 The system according to any of the preceding system embodiments with the features of S42, wherein the heart-rate sensing devices are portable and configured to be worn by a user.

S46 The system according to the preceding embodiment, wherein the heart-rate sensing devices are at least one of smart watches, bracelets and another wearable fitness tracker device configured for heart-rate sensing.

S47 The system according to any of the preceding system embodiments with the features of S45 and S11, wherein each data-device comprises at least one of the heart-rate sensing devices.

S48 The system according to any of the preceding system embodiments,
wherein the system is configured for generating skeleton data of the user.

S49 The system according to any of the preceding system embodiments,
wherein the system is configured for generating the skeleton data of the user based on the image data captured by at least one of the at least one camera (20).

S50 The system according to any of the preceding system embodiments, wherein the system is configured for generating skeleton-trajectory data of the user based on image data captured by at least one of the at least one camera (20).

S51 The system according to any of the preceding system embodiments with the features of at least one of S35, S49 and/or S50,
wherein the system is configured for
at least one of the generating of the heart-rate data, the generating of the skeleton data and/or the generating of the skeleton-trajectory data of at least one or a plurality of users using training machine assemblies of the system, and
using at least one boundary condition corresponding to the respective training machine assemblies' geometries.

S52 The system according to the preceding embodiment,
wherein at least one of the at least one boundary condition are possible positions of at least one part of the body of the user.

S53 The system according to any of the two preceding embodiments,
wherein at least one of the at least one boundary condition are possible trajectories of movable parts of at least one of the respective training machine assembly.

S54 The system according to any of the three preceding embodiments,
wherein at least one of the at least one boundary condition are possible trajectories of at least parts of the body of the user interacting with at least one of the respective training machine assemblies.

S55 The system according to any of the preceding system embodiments,
wherein the system is configured to sense the training effort of the user at a group of training machine assemblies (10).

S56 The system according to the preceding system embodiment, wherein the group of training machine assemblies (10) comprises at least one training machine assembly (10), which at least one training machine is configured for effort sensing.

S57 The system according to the penultimate system embodiment, wherein the group of training machine assemblies (10) comprises a plurality of the training machine assemblies (10) of the system, of which plurality each training machine is configured for effort sensing.

S58 The system according to the antepenultimate system embodiment, wherein the group of training machine assemblies comprises all training machine assemblies

(10) of the system, which training machine assemblies are each configured for effort sensing.

S59 The system according to any of the preceding system embodiments with the features of S55,
wherein the training machine assemblies (10) of the group of training machine assemblies (10) are according to T24 or an embodiment depending on T24.

S60 The system according to any of the preceding system embodiments with the features of S55, wherein each training resistance of the group of training machine assemblies (10) comprises a sensing unit that is configured for sensing the user's training effort.

S61 The system according to any of the preceding system embodiments with the features of S8,
wherein the data processing system is configured for storing data relating to the training-resistance value for at least one user at at least one training machine assembly.

S62 The system according to any of the preceding system embodiments with the features of S61,
wherein the system is configured for generating activity data of the user based at least on an interaction of the user with at least one of the training machine assemblies (10).

S63 The system according to any of the preceding system embodiments with the features of S61,
wherein the system is configured for generating heart-rate reference data based on at least one of
the predetermined heart-rate data,
the heart-rate data of the user corresponding to different activity levels of the user,
the heart-rate data of the user corresponding to at least one of the at least one training resistance value,
a comparison of portions or points of the heart-rate data of the user, and
a gradient in the heart-rate data of the user.

S64 The system according to any of the preceding system embodiments with the features of S61,
wherein at least a plurality of the training machine assemblies of the system are according to T3 or any depending embodiment of T3.

S65 The system according to any of the preceding system embodiments with the features of S8, wherein the system is configured for generating performance data for at least one user.

S66 The system according to any of the preceding system embodiments with the features of S65 and S35, wherein generating the performance data for the at least one user is based at least on the heart-rate data of the at least one user.

S67 The system according to any of the preceding system embodiments with the features of S65 and S36, wherein the wherein generating the performance data for the at least one user is based at least on the heart-rate variability data of the at least one user.

S68 The system according to any of the preceding system embodiments with the features of S65 and S63, wherein generating the performance data for the at least one user is based at least on the heart-rate reference data of the at least one user.

S69 The system according to any of the two preceding system embodiments, wherein generating the performance data is based furthermore on comparing the heart-rate data and the heart-rate reference data.

S70 The system according to any of the preceding system embodiments with the features of S65 and S48, wherein generating the performance data for the at least one user is based at least on the skeleton data of the at least one user.

S71 The system according to any of the preceding system embodiments with the features of S65 and S50, wherein generating the performance data for the at least one user is based at least on the skeleton-trajectory data of the at least one user.

S72 The system according to any of the preceding system embodiments with the features of S65, wherein generating the performance data for the at least one user is based at least on the training resistance value of the training resistance used by the at least one user.

S73 The system according to any of the preceding system embodiments with the features of S65, S62 and S35, wherein generating the performance data for the at least one user is based at least on comparing a change of activity data and a change of the heart-rate data.

S74 The system according to any of the preceding system embodiments with the features of S65 and S35, wherein generating the performance data for the at least one user is based at least on comparing the training resistance value of the training resistance used by the at least one user and the heart-rate reference data.

S75 The system according to any of the preceding system embodiments with the features of S65, wherein the system is configured for identifying a deviation in the performance data relating to the user and to thus generate performance-deviation data for the user.

S76 The system according to any of the preceding system embodiments with the features of S75, wherein the performance-deviation data comprise data relating to an exhaustion level of the user.

S77 The system according to the preceding system embodiment and with the features of S67, wherein the data relating to the exhaustion level of the user are generated at least based on the heart-rate variability data.

S78 The system according to any of the preceding system embodiments, wherein the system is configured to generate instruction data.

S79 The system according to any of the preceding system embodiments, wherein the system is further configured for outputting the instruction data.

S80 The system according to any of the preceding system embodiments, wherein the system comprises at least one user interface that is configured for outputting the instruction data.

S81 The system according to any of the preceding system embodiments, wherein the system comprises a plurality of user interfaces that are configured for outputting the instruction data.

S82 The system according to any of the preceding system embodiments with the features of S65 and S78, wherein the system is configured to generate the instruction data based at least on the performance data.

S83 The system according to any of the preceding system embodiments with the features of S75 and S78, wherein the system is configured to generate the instruction data based at least on the performance-deviation data S84 The system according to any of the preceding system embodiments, wherein the system is configured for adjusting at least one of the training resistances.

S85 The system according to any of the preceding system embodiments, wherein the system is configured for adjusting all training resistances.

S86 The system according to any of the preceding system embodiments, wherein
- at least one or a plurality of the training machine assemblies of the system (10) are according to T4, and
- the system is configured for automatically adjusting at least one or all automatically adjustable user support elements.

S87 The system according to any of the preceding system embodiments with the features of S86, wherein at least one or a plurality of the training machine assemblies of the system are according to T61.

S88 The system according to any of the preceding embodiments with the features of S84, wherein the system is configured for adjusting at least one or all of the training resistances based on the heart-rate data.

S89 The system according to any of the preceding embodiments with the features of S84, wherein the system is configured for adjusting at least one or all of the training resistances based on the heart-rate variability data.

S90 The system according to any of the preceding system embodiments, wherein the system is configured to process user plan data.

S91 The system according to the preceding system embodiment, wherein the user plan data comprise data relating to at least one user exercise.

S92 The system according to any of the preceding system embodiments with the features of S90, wherein the user plan data comprise data relating to a plurality of user exercises.

S93 The system according to any of the preceding system embodiments with the features of S90, wherein the user plan data comprise rule data for the user exercise(s).

S94 The system according to any of the preceding system embodiments with the features of S90, wherein the user plan data comprise parameters for the user exercise(s).

S95 The system according to any of the preceding system embodiments with the features of S90, wherein the user plan data comprise target performance data.

S96 The system according to any of the preceding system embodiments with the features of S90, wherein the user plan data comprise target heart-rate data.

S97 The system according to the preceding system embodiment, wherein the target heart-rate data comprise a target range for the user heart-rate.

S98 The system according to any of the preceding system embodiments with the features of S90, wherein the user plan data comprise types of the user exercise(s).

S99 The system according to any of the preceding system embodiments with the features of S90, wherein the user plan data comprise an indication of suitable training machine assemblies (10) for each user exercise(s).

S100 The system according to any of the preceding system embodiments with the features of S90, wherein the user plan data comprise an indication of at least one order of user exercise(s).

S101 The system according to any of the preceding system embodiments with the features of S90, wherein the user plan data comprise data relating to a training resistance for at least one exercise.

S102 The system according to any of the preceding system embodiments with the features of S90, wherein the user plan data comprise data relating to training resistances for a plurality of exercises.

S103 The system according to any of the preceding system embodiments with the features of S90, wherein the system is configured for receiving the user plan data.

S104 The system according to any of the preceding system embodiments with the features of S90, wherein the system is configured for transmitting the user plan data.

S105 The system according to any of the preceding system embodiments with the features of S90, wherein the system is configured for adapting the user plan data.

S106 The system according to the preceding system embodiment and S75, wherein the adapting the user plan data is based at least on the performance-deviation data of the user.

S107 The system according to any of the preceding system embodiments with the features of S105 and S35, wherein the adapting the user plan data is based at least on the heart-rate data.

S108 The system according to any of the preceding system embodiments with the features of S105 and S36, wherein the adapting the user plan data is based at least on the heart-rate variability data.

S109 The system according to any of the preceding system embodiments with the features of S105, wherein the adapting of the user plan data is based at least on temporal changes of the heart rate of the user.

S110 The system according to any of the preceding system embodiments with the features of S105, wherein the adapting of the user plan data is based at least on a measure for an increase and/or a decrease of the heart-rate of the user.

S111 The system according to any of the preceding system embodiments with the features of S105, wherein the user plan data comprise data relating to the training resistance and wherein adapting of the user plan data comprises adapting the data relating to the training resistance based on the performance data and the target performance data.

S112 The system according to any of the preceding system embodiments with the features of S105, wherein the user plan data comprise data relating to the training resistance and wherein adapting of the user plan data comprises adapting the data relating to the training resistance based on the heart-rate variability of the user.

S113 The system according to any of the preceding system embodiments with the features of S105, wherein the user plan data comprise data relating to the training resistance and wherein adapting of the user plan data comprises adapting the data relating to the training resistance based on the heart-rate data and the target heart-rate data.

S114 The system according to any of the preceding system embodiments with the features of S105, wherein the user plan data comprise data relating to the training resistance and wherein adapting of the user plan data comprises adapting the data relating to the training resistance based on the measure for the increase and/or the decrease of the heart-rate of the user.

S115 The system according to any of the four preceding system embodiments, wherein the adapting of the data relating to the training resistance is based on history data relating to adapting the training resistance and a change of the respective measure for the user performance.

S116 The system according to the preceding embodiment, wherein the system is configured to perform the adapting based on the history data by a machine-learning algorithm trained with the history data.

S117 The system according to any of the preceding system embodiments with the features of S90 and S84, wherein the system is configured for adjusting at least one of the training resistances based on at least a portion of the user plan data.

S118 The system according to any of the preceding system embodiments with the features of S90 and S78, wherein the system is configured to generate the instruction data based on at least a portion of the user plan data.

S119 The system according to any of the preceding system embodiments with the features of S90 and S78, wherein the instruction data comprise data relating to a further exercise of the user.

S120 The system according to any of the preceding system embodiments with the features of S65, wherein the system is configured to transmit at least a portion of the performance data.

S121 The system according to any of the preceding system embodiments with the features of S75, wherein the system is configured to transmit at least a portion of the performance-deviation data.

S122 The system according to any of the preceding system embodiments with the features of S35, wherein the system is configured to transmit at least a portion of the heart-rate data.

S123 The system according to any of the preceding system embodiments with the features of S35, wherein the system is configured to transmit at least a portion of the heart-rate reference data.

S124 The system according to any of the preceding system embodiments with the features of S48, wherein the system is configured to transmit at least a portion of the skeleton data.

S125 The system according to any of the preceding system embodiments with the features of S50, wherein the system is configured to transmit at least a portion of the skeleton-trajectory data.

S126 The system according to any of the preceding system embodiments with the features of S78, wherein the system is configured to transmit at least a portion of the instruction data.

S127 The system according to any of the preceding system embodiments with the features of S90, wherein the system is configured to transmit at least a portion of the user plan data.

S128 The system according to any of the preceding embodiments S120-S127, wherein the system is configured to transmit the data to the server system.

S129 The system according to any of the preceding embodiments S120-S128, wherein the system is configured to transmit the data to the end user computer device.

S130 The system according to the preceding embodiment, wherein the end user computer device is portable.

S131 The system according to any of the preceding embodiments with the features of S129, wherein system comprises the end user computer device.

S132 The system according to any of the preceding embodiments with the features of S129 and S78, wherein the end user computer device is configured for outputting at least a part of the instruction data.

S133 The system according to any of the preceding embodiments with the features of S129 and S90, wherein the end user computer device is configured for outputting at least a part of the user plan data.

S134 The system according to any of the preceding embodiments with the features of at least one of S86, wherein the system is configured for automatically adjusting at least one or all automatically adjustable user support elements based on comparison data.

S135 The system according to any of the preceding embodiments with the features of S134 and S48, wherein
the system is configured for comparing the skeleton data to skeleton-reference data and to thus generating skeleton-comparison data, and
the comparison data comprise at least a portion of the skeleton-comparison data.

S136 The system according to any of the preceding embodiments with the features of S134 and S50, wherein
the system is configured for comparing the skeleton-trajectory data to skeleton-reference data and to thus generating trajectory-comparison data, and
the comparison data comprise at least a portion of the trajectory-comparison data.

S137 The system according to any of the preceding embodiments with the features of S134 and S50, wherein
the system is configured for comparing the skeleton-trajectory data to skeleton-reference data and adapting the skeleton-reference data; and to thus generating trajectory-comparison data, and
the comparison data comprise at least a portion of the trajectory-comparison data.

S138 The system according to the preceding embodiment, wherein adapting the skeleton-reference data is based at least one the skeleton data.

S139 The system according to any of the preceding embodiments with the features of S134, wherein the system is configured for adjusting at least one of the at least one training resistance based on at least one of the comparison data, the skeleton-comparison data and the trajectory-comparison data.

S140 The system according to any of the preceding embodiments with the features of S134 and S78, wherein the system configured for outputting the instruction data based on at least one of the comparison data, the skeleton-comparison data and the trajectory-comparison data.

S141 The system according to any of the preceding embodiments, wherein the system is a system for strength training.

S142 The system according to any of the preceding system embodiments, wherein a plurality of the training machine assemblies (10) of the system are according to T67.

S143 The system according to any of the preceding system embodiments, wherein the system is configured for user identification.

S144 The system according to the preceding system embodiment, wherein the system is further configured for user identification by facial recognition.

S145 The system according any of the preceding system embodiments, wherein the system is a system for circuit training.

S146 The system according to the preceding system embodiment, wherein each of the training machine assemblies is configured for at least one user exercise and wherein at least some user exercises are different from each other.

S147 The system according to any of the preceding system embodiments, wherein the at least one user is a plurality of users and wherein the system is configured to perform the steps that it performs for the at least one user for each of the plurality of the users respectively.

S148 The system according to any of the preceding embodiments with the features of S88, wherein the system is configured for adjusting at least one or all of the training resistances for at least one of the user(s) based on a portion of the heart-rate data relating to the heart-rate of the respective user during at least one of a preceding exercise performed by the user and a time between the preceding exercise of the user and a respectively current exercise at the training machine assembly (10) of the system that the user uses.

S149 The system according to any of the preceding embodiments with the features of S89, wherein the system is configured for adjusting at least one or all of the training resistances for the at least one user based on the heart-rate variability of the at least one user before the current exercise at the training machine assembly.

S150 The system according to any of the preceding system embodiments with the features of 105, wherein the system is configured for adapting the user plan data relating to a next exercise of the at least one user.

S151 The system according to the preceding system embodiment and S75, wherein the adapting the user plan data relating to the next exercise of the user is based at least on the performance-deviation data relating to at least one of the current and the current as well as at least one preceding user exercise of the user.

S152 The system according to any of the preceding system embodiments with the features of S150 and S35, wherein the adapting the user plan data relating to the next exercise of the user is based at least on the heart-rate data relating to at least one of the current and the current as well as at least one preceding user exercise of the user.

S153 The system according to any of the preceding system embodiments with the features of S150 and S36, wherein the adapting the user plan data relating to the next exercise of the user is based at least on the heart-rate variability data relating to at least one of the current and the current as well as at least one preceding user exercise of the user.

S154 The system according to any of the preceding system embodiments with the features of S150, wherein the adapting the user plan data relating to the next exercise of the user is based at least on temporal changes of the heart rate of the user during at least one of the current and the current as well as at least one preceding user exercise of the user.

S155 The system according to any of the preceding system embodiments with the features of S150, wherein the adapting the user plan data relating to the next exercise of the user is based at least on a measure for an increase and/or a decrease of the heart-rate of the user during at least one of the current and the current as well as at least one preceding user exercise of the user.

S156 The system according to any of the preceding system embodiments with the features of at least one of S111-S116, wherein the user plan data comprise data relating to the at least one next training resistance and wherein adapting of the user plan data comprises adapting the data relating to the next training resistance based on the respectively specified data relating to at least one of the current and the current as well as at least one preceding user exercise of the user.

Below, data-processing system embodiments will be discussed. These embodiments are abbreviated by the letter "D" followed by a number. Whenever reference is herein made to "data-processing system embodiments", these embodiments are meant.

D1 A data-processing system (32), wherein the data-processing system (32) is configured to receive data, send data and process data.

D2 The data-processing system (32) according to the preceding embodiment, wherein the data-processing system (32) is configured to receive the user plan data.

D3 The data-processing system (32) according to any of the preceding embodiments, wherein the data-processing system (32) is configured to generate the user plan data.

D4 The data-processing system (32) according to any of the preceding embodiments, wherein the data-processing system (32) is configured to receive and/or store the user plan data.

D5 The data-processing system (32) according to any of the preceding data-processing system embodiments with the features of at least one of D2, D3 and D4, wherein the user plan data comprise data relating to at least one user exercise.

D6 The data-processing system (32) according to any of the preceding data-processing system embodiments with the features of at least one of D2, D3 and D4, wherein the user plan data comprise data relating to a plurality of user exercises.

D7 The data-processing system (32) according to any of the preceding data-processing system embodiments with the features of at least one of D2, D3 and D4, wherein the user plan data comprise rule data for the user exercise(s).

D8 The data-processing system (32) according to any of the preceding data-processing system embodiments with the features of at least one of D2, D3 and D4, wherein the user plan data comprise parameters for the user exercise(s).

D9 The data-processing system (32) according to any of the preceding data-processing system embodiments with the features of at least one of D2, D3 and D4, wherein the user plan data comprise target performance data.

D10 The data-processing system (32) according to any of the preceding data-processing system embodiments with the features of at least one of D2, D3 and D4, wherein the user plan data comprise target heart-rate data.

D11 The data-processing system (32) according to any of the two preceding data-processing system embodiments, wherein the target performance data comprise the target heart-rate data.

D12 The data-processing system (32) according to any of the two preceding embodiments, wherein the target heart-rate data comprise a target range for the user heart-rate.

D13 The data-processing system (32) according to any of the preceding data-processing system embodiments with the features of at least one of D2, D3 and D4, wherein the user plan data comprise types of the user exercise(s).

D14 The data-processing system (32) according to any of the preceding data-processing system embodiments with the features of at least one of D2, D3 and D4, wherein the user plan data comprise an indication of suitable training machine assemblies (10) for each user exercise(s).

D15 The data-processing system (32) according to any of the preceding data-processing system embodiments with the features of at least one of D2, D3 and D4, wherein the user plan data comprise an indication of at least one order of the user exercise(s).

D16 The data-processing system (32) according to any of the preceding data-processing system embodiments with the features of at least one of D2, D3 and D4, wherein the user plan data comprise data relating to a training resistance for at least one exercise.

D17 The data-processing system (32) according to any of the preceding data-processing system embodiments with the features of at least one of D2, D3 and D4, wherein the user plan data comprise data relating to training resistances for a plurality of exercises.

D18 The data-processing system (32) according to the any of the preceding embodiments, wherein data-processing system is configured for processing the instruction data.

D19 The data-processing system (32) according to the any of the preceding embodiments with the features of D18, wherein data-processing system is configured for generating the instruction data.

D20 The data-processing system (32) according to the preceding embodiment, wherein generating the instruction data comprises selecting the instruction data from a set of instruction data.

D21 The data-processing system (32) according to the any of the preceding embodiments with the features of D18, wherein the data-processing system is configured for outputting and/or sending instruction data.

D22 The data-processing system (32) according to the any of the preceding embodiments with the features of D18, wherein the data-processing system is configured for generating the instruction data based on the user plan data.

D23 The data-processing system (32) according to the any of the preceding embodiments with the features of D18, wherein the instruction data comprise at least an indication relating to a training resistance for at least one exercise.

D24 The data-processing system (32) according to the any of the preceding embodiments with the features of D18, wherein the instruction data comprise at least an indication relating to training resistances for a plurality of exercises.

D25 The data processing system (32) according to any of the preceding embodiments, wherein the data-processing system is configured for controlling at least one training resistance of at least one training machine assembly.

D26 The data-processing system (32) according to the preceding embodiment, wherein the at least one training machine assembly is according to any of the training machine assembly embodiments.

D27 The data-processing system (32) according to any of the two preceding embodiments, wherein the at least one training machine assembly is a plurality of training machine assemblies and the at least one training resistance is a plurality of training resistances.

D28 The data-processing system (32) according to any of the preceding three data-processing system embodiments, wherein data-processing system is configured for controlling the at least one training resistance based on the user plan data.

D29 The data-processing system (32) according to any of the preceding three data-processing system embodiments, wherein data-processing system is configured for controlling the at least one training resistance based on the instruction data.

D30 The data-processing system (32) according to any of the preceding four data-processing system embodiments, wherein the data-processing system is configured for controlling the at least one training machine assembly by sending data to the at least one training machine assembly.

D31 The data-processing system (32) according to any of the preceding data-processing system embodiments, wherein the data-processing system is configured for storing and/or processing heart-rate data of the user.

D32 The data-processing system (32) according to any of the preceding data-processing system embodiments, wherein the data-processing system is configured for generating heart-rate data of the user.

D33 The data-processing system (32) according to any of the preceding data-processing system embodiments, wherein the data-processing system is configured for storing and/or processing heart-rate variability data of the user.

D34 The data-processing system (32) according to any of the preceding two data-processing system embodiments, wherein the data-processing system is configured for generating heart-rate variability data of the user.

D35 The data-processing system (32) according to any of the preceding data-processing system embodiments with the features of D31, wherein the data-processing system (32) is configured determining the temporal changes of the heart rate of the user.

D36 The data-processing system (32) according to any of the preceding data-processing system embodiments with the features of D31, wherein the data-processing system (32) is configured processing the temporal changes of the heart rate of the user.

D37 The data-processing system (32) according to any of the preceding data-processing system embodiments with the features of D31, wherein the data-processing system (32) is configured determining the measure for an increase and/or a decrease of the heart-rate of the user.

D38 The data-processing system (32) according to any of the preceding data-processing system embodiments with the features of D31, wherein the data-processing system (32) is configured processing the measure for the increase and/or decrease of the heart-rate of the user.

D39 The data-processing system (32) according to any of the preceding data-processing system embodiments, wherein the data-processing system (32) is configured for generating and/or receiving image data of the user.

D40 The data-processing system (32) according to any of the preceding data-processing system embodiments, wherein the data-processing system (32) is configured for generating and/or receiving skeleton data and/or skeleton-trajectory data of the user.

D41 The data-processing system (32) according to any of the preceding data-processing system embodiments with the features of D39, wherein the data-processing system (32) is configured for generating the skeleton data and/or the skeleton-trajectory data of the user based on the image data of the user.

D42 The data-processing system (32) according to any of the preceding data-processing system embodiments with the features of D39, wherein the data-processing system (32) is configured for generating the heart-rate data of the user based on the image data of the user.

D43 The data-processing system (32) according to any of the preceding data-processing system embodiments with the features of D41, wherein the data-processing system (32) is configured for using at least one boundary condition corresponding to an exercise of the user for generating the skeleton data of the user.

D44 The data-processing system (32) according to any of the preceding data-processing system embodiments with the features of D42, wherein the data-processing system (32) is configured for using at least one boundary condition corresponding to an exercise of the user for generating the heart-rate data of the user.

D45 The data-processing system (32) according to any of the preceding two data-processing system embodiments, wherein at least one of the at least one boundary condition relates to a training machine assembly used to perform the user exercise.

D46 The data-processing system (32) according to any of the preceding three data-processing system embodiments, wherein at least one of at least one boundary condition relates to possible positions of at least one part of the body of the user using the training machine assembly.

D47 The data-processing system (32) according to any of the preceding four data-processing system embodiments, wherein at least one of the at least one boundary condition relates to possible trajectories of movable parts of at least one of the respective training machine assembly.

D48 The data-processing system (32) according to any of the preceding five data-processing system embodiments, wherein at least one of at least one boundary condition relates to possible trajectories of at least parts of the body of the user interacting with at least one of the respective training machine assemblies.

D49 The data-processing system (32) according to any of the preceding data-processing system embodiments, wherein the data-processing system (32) is configured for storing and/or processing the performance data.

D50 The data-processing system (32) according to any of the preceding data-processing system embodiments, wherein the data-processing system (32) is configured for generating the performance data.

D51 The data-processing system (32) according to any of the preceding data-processing system embodiments with the features of D50, wherein the data-processing system (32) is configured for generating the performance data for the at least one user based at least on the heart-rate data of the at least one user.

D52 The data-processing system (32) according to any of the preceding data-processing system embodiments with the features of D50, wherein the data-processing system (32) is configured for generating the performance data for the at least one user based at least on the heart-rate variability data of the at least one user.

D53 The data-processing system (32) according to any of the preceding data-processing system embodiments with the features of D50, wherein the data-processing system (32) is configured for generating the performance data for the at least one user based at least on the heart-rate reference data of the at least one user.

D54 The data-processing system (32) according to any of the preceding data-processing system embodiments with the features of D50, wherein the data-processing system (32) is configured for generating the performance data for the at least one user based furthermore on comparing the heart-rate data and the heart-rate reference data of the user.

D55 The data-processing system (32) according to any of the preceding data-processing system embodiments with the features of D50, wherein the data-processing system (32) is configured for generating the performance data for the at least one user based at least on the skeleton data of the at least one user.

D56 The data-processing system (32) according to any of the preceding data-processing system embodiments, wherein the data-processing system (32) is configured for processing and/or receiving the history data.

D57 The data-processing system (32) according to any of the preceding data-processing system embodiments, wherein the data-processing system (32) is configured for generating the history data.

D58 The data-processing system (32) according to any of the preceding data-processing system embodiments, wherein the data-processing system (32) is configured for storing the history data.

D59 The data-processing system (32) according to any of the preceding data-processing system embodiments with the features of at least one of D56, D57 and D58, wherein the history-data comprise data relating to the training resistances.

D60 The data-processing system (32) according to any of the preceding data-processing system embodiments with the features of at least one of D56, D57 and D58, wherein the history-data comprise data relating to at least one training resistance for at least one exercise and/or to training resistances for a plurality of exercises.

D61 The data-processing system (32) according to any of the preceding data-processing system embodiments with the features of at least one of D56, D57 and D58, wherein the history-data comprise heart-rate data.

D62 The data-processing system (32) according to any of the preceding data-processing system embodiments with the features of at least one of D56, D57 and D58, wherein the history-data comprise heart-rate variability data.

D63 The data-processing system (32) according to any of the preceding data-processing system embodiments with the features of at least one of D56, D57 and D58, wherein the history-data comprise data relating to at least one of
the temporal changes of the heart rate of the user, and
the measure for the increase and/or the decrease of the heart-rate of the user.

D64 The data-processing system (32) according to any of the preceding data-processing system embodiments with the features of at least one of D56, D57 and D58, wherein the history-data comprise instruction data.

D65 The data-processing system (32) according to any of the preceding data-processing system embodiments with the features of at least one of D56, D57 and D58, wherein the history-data comprise skeleton data.

D66 The data-processing system (32) according to any of the preceding data-processing system embodiments with the features of at least one of D56, D57 and D58, wherein the history-data comprise skeleton-trajectory data.

D67 The data-processing system (32) according to any of the preceding data-processing system embodiments with the features of at least one of D56, D57 and D58, wherein the history-data comprise performance data.

D68 The data-processing system (32) according to any of the preceding data-processing system embodiments, wherein the data-processing system (32) is configured for receiving and/or processing the reference data.

D69 The data-processing system (32) according to any of the preceding data-processing system embodiments, wherein the data-processing system (32) is configured for generating the reference data.

D70 The data-processing system (32) according to any of the preceding data-processing system embodiments, wherein the data-processing system (32) is configured for storing the reference data.

D71 The data-processing system (32) according to any of the preceding data-processing system embodiments, wherein the data-processing system (32) is configured for generating the comparison data.

D72 The data-processing system (32) according to any of the preceding data-processing system embodiments, wherein the data-processing system (32) is configured for storing the comparison data.

D73 The data-processing system (32) according to any of the preceding data-processing system embodiments, wherein the data-processing system (32) is configured for processing and/or receiving the comparison data.

D74 The data-processing system (32) according to any of the preceding data-processing system embodiments with the features of D71, wherein the data-processing system (32) is configured for generating the comparison data by comparing data relating to the user to reference data.

D75 The data-processing system (32) according to any of the preceding data-processing system embodiments with the features of at least one of D68, D69 and D70, wherein the reference data comprise skeleton-reference data.

D76 The data-processing system (32) according to any of the preceding data-processing system embodiments with the features of D71 and D75, wherein the comparison data comprise skeleton-comparison data and the data-processing system (32) is configured to generate the skeleton-comparison data by comparing the skeleton data to the skeleton reference-data.

D77 The data-processing system (32) according to any of the preceding data-processing system embodiments with the features of D71 and D75, wherein the comparison data comprise trajectory-comparison data and the data-processing system (32) is configured to generate the trajectory-comparison data by comparing the skeleton-trajectory data to the skeleton reference-data.

D78 The data-processing system (32) according to any of the preceding data-processing system embodiments with the features of D71 and D75, wherein the system is configured for comparing the skeleton-trajectory data to skeleton-reference data and adapting the skeleton-reference data; and to thus generating trajectory-comparison data, and the comparison data comprise at least a portion of the trajectory-comparison data.

D79 The data-processing system (32) according to the preceding data-processing system embodiment, wherein adapting the skeleton-reference data is based at least one the skeleton data.

D80 The data-processing system (32) according to any of the preceding data-processing system embodiments with the features of at least one of D68, D69 and D70, wherein the reference data comprise heart-rate reference data.

D81 The data-processing system (32) according to any of the preceding data-processing system embodiments with the features of D71 and D80, wherein the comparison data comprise heart-rate comparison data and the data-processing system (32) is configured to generate the heart-rate comparison data by comparing the heart-rate data to the heart-rate reference data.

D82 The data-processing system (32) according to any of the preceding data-processing system embodiments with the features of at least one of D2, D3 and D4, wherein the data-processing system (32) is configured for adapting the user plan data.

D83 The data-processing system (32) according to any of the preceding data-processing system embodiments with the features of D80, wherein the data-processing system is configured for adapting the user plan data based on the heart-rate data.

D84 The data-processing system (32) according to any of the preceding data-processing system embodiments with the features of D82, wherein the data-processing system is configured for adapting the user plan data based on the heart-rate variability data.

D85 The data-processing system (32) according to any of the preceding data-processing system embodiments with the features of D82, wherein the data-processing system is configured for adapting the user plan data based on the heart-rate variability data.

D86 The data-processing system (32) according to any of the preceding data-processing system embodiments with the features of D82, wherein the data-processing system is configured for adapting the user plan data based on the temporal changes of the heart rate of the user.

D87 The data-processing system (32) according to any of the preceding data-processing system embodiments with the features of D82, wherein the data-processing system is configured for adapting the user plan data based on the measure for the increase and/or the decrease of the heart-rate of the user.

D88 The data-processing system (32) according to any of the preceding data-processing system embodiments with the features of D82, wherein the data-processing system is configured for adapting the user plan data based on the skeleton data.

D89 The data-processing system (32) according to any of the preceding data-processing system embodiments with the features of D82, wherein the data-processing system is configured for adapting the user plan data based on the skeleton-trajectory data.

D90 The data-processing system (32) according to any of the preceding data-processing system embodiments with the features of D82 and with the features of at least one D49, D50 and D51, wherein the data-processing system is configured for adapting the user plan data based on the performance data.

D91 The data-processing system (32) according to any of the preceding data-processing system embodiments with the features of D82 and D9, wherein the data-processing system is configured for adapting the user plan data based on the performance target data.

D92 The data-processing system (32) according to any of the preceding data-processing system embodiments with the features of D82 and at least one of D56, D57 and D58, wherein the data-processing system is configured for adapting the user plan data based on the history data.

D93 The data-processing system according to any of the preceding data-processing system embodiments with the features of D28 and D82, wherein data-processing system is configured for controlling the at least one training resistance based on the adapted user plan data.

D94 The data-processing system according to any of the preceding data-processing system embodiments with the features of D28 and D71, wherein data-processing system is configured for controlling the at least one training resistance based on the comparison data.

D95 The data-processing system according to any of the preceding data-processing system embodiments with the features of D18 and D82, wherein data-processing system is configured for adapting the instruction data based on the adapted user plan data.

D96 The data-processing system according to any of the preceding data-processing system embodiments with the features of D18 and D71, wherein data-processing system is configured for adapting the instruction data based on the comparison data.

D97 The data-processing system according to any of the preceding data-processing system embodiments with the features of D56 and at least one of D93 and D95, wherein the data-processing system (32) is configured for adapting the instruction data and/or the user plan data based on the history data.

D98 The data-processing system according to the preceding data-processing system embodiment, wherein the data-processing system (32) is configured for applying machine learning algorithms to the history data.

D99 The data-processing system according to any of the preceding two data-processing system embodiments, wherein the data-processing system (32) is configured for applying pattern recognition algorithms to the history data.

D100 The data-processing system according to any of the preceding three data-processing system embodiments, wherein the data-processing system (32) is configured for applying reinforcement-learning algorithms to the history data.

D101 The data-processing system according to any of the preceding three data-processing system embodiments, wherein the data-processing system (32) is configured for applying neural-network algorithms to the history data.

D102 The data-processing system according to any of the preceding data-processing system embodiments, wherein the data-processing system is configured to be connected to the heart-rate sensing device.

D103 The data-processing system according to any of the preceding data-processing system embodiments, wherein the data-processing system comprises the heart-rate sensing device.

D104 The data-processing system according to any of the preceding data-processing system embodiments, wherein the data-processing system is configured for sensing the heart rate of the user.

D105 The data-processing system according to any of the preceding data-processing system embodiments, wherein the data-processing system is further configured for sensing the heart-rate variability of the user.

D106 The data-processing system according to any of the preceding system embodiments with the features of D105 and at least one of D102 and D103, wherein the heart-rate sensing device is configured for sensing the heart-rate variability of the user.

D107 The data-processing system according to any of the preceding data-processing system embodiments, wherein the data-processing system is configured to receive data from at least one wearable device.

D108 The data-processing system according to the preceding data-processing system embodiment, wherein the at least one wearable device is a plurality of wearable devices.

D109 The data-processing system according to any of the preceding data-processing system embodiments with the features of D107, wherein each of the at least one wearable device comprises a heart-rate sensing device.

D110 The data-processing system according to any of the preceding data-processing system embodiments with the features of D107, wherein the at least one wearable device is further configured for sensing the heart-rate of the user.

D111 The data-processing system according to any of the preceding data-processing system embodiments with the features of D107, wherein the at least one wearable device is further configured for sensing the heart-rate variability of the user.

D112 The data-processing system according to any of the preceding data-processing system embodiments, wherein the data-processing system comprises an end user computer device.

D113 The data-processing system according to the preceding data-processing system embodiment, wherein the end user computer device is portable.

D114 The data-processing system according to any of the preceding two data-processing system embodiments, wherein the end user computer device is a smart mobile device.

D115 The data-processing system according to any of the preceding data-processing system embodiments, wherein the data-processing system comprises a server system.

D116 The data-processing system according to any of the preceding data-processing system embodiments, wherein the data-processing system is configured for sending data.

D117 The data-processing system according to any of the preceding data-processing system embodiments with the features of D116, wherein the data to be sent by the data-processing system comprise heart-rate data.

D118 The data-processing system according to any of the preceding data-processing system embodiments with the features of D116, wherein the data to be sent by the data-processing system comprise performance data.

D119 The data-processing system according to any of the preceding data-processing system embodiments with the features of D116, wherein the data to be sent by the data-processing system comprise instruction data.

D120 The data-processing system according to any of the preceding data-processing system embodiments with the features of D116, wherein the data to be sent by the data-processing system comprise data relating to the at least one training resistance.

D121 The data-processing system according to any of the preceding data-processing system embodiments with the features of D116, wherein the data to be sent by the data-processing system comprise data relating to the plurality of training resistances.

D122 The data-processing system according to any of the preceding data-processing system embodiments with the features of D116, wherein the data to be sent by the data-processing system comprise performance data.

D123 The data-processing system according to any of the preceding data-processing system embodiments with the features of D116, wherein the data to be sent by the data-processing system comprise comparison data.

D124 The data-processing system according to any of the preceding data-processing system embodiments, wherein the data-processing system is configured for receiving data.

D125 The data-processing system according to any of the preceding data-processing system embodiments with the features of D124, wherein the data to be received by the data-processing system comprise heart-rate data.

D126 The data-processing system according to any of the preceding data-processing system embodiments with the features of D124, wherein the data to be received by the data-processing system comprise data relating to the at least one training resistance.

D127 The data-processing system according to any of the preceding data-processing system embodiments with the features of D124, wherein the data to be received by the data-processing system comprise heart-rate variability data.

D128 The data-processing system according to any of the preceding data-processing system embodiments with the features of D124, wherein the data to be received by the data-processing system comprise history data.

D129 The data-processing system according to any of the preceding data-processing system embodiments, wherein the data-processing system is configured to be connected to at least one training machine assembly according to any of the training machine assembly embodiments.

D130 The data-processing system according to the preceding data-processing system embodiment, wherein the at least one training machine assembly is a plurality of training machine assemblies.

D131 The data-processing system according to any of the preceding data-processing system embodiments, wherein the data-processing system is configured to be connected to a system according to any of the system embodiments.

D132 The data-processing system according to any of the preceding data-processing system embodiments, wherein the user is a plurality of users and wherein the data-processing system is configured for processing data for a plurality of users.

D133 The data-processing system according to any of the preceding data-processing system embodiments, wherein the user is a plurality of users and wherein the data-processing system is configured for performing the steps that it performs for the user for each of the plurality of the users respectively.

D134 The data-processing system according to any of the preceding two data-processing system embodiments, wherein the data-processing system is configured for performing the steps that it is configured to perform at a plurality of times.

D135 The data-processing system (32) according to any of the preceding data-processing system embodiments with the features of D16, wherein the user plan data comprise data relating to a training resistance for at least one next exercise of the user.

D136 The data-processing system (32) according to any of the preceding data-processing system embodiments with the features of D17, wherein the user plan data comprise data relating to training resistances for a plurality of exercises, comprising the at least one next exercise of the user.

D137 The data-processing system (32) according to the any of the preceding embodiments with the features of D23, wherein the instruction data comprise at least an indication relating to a training resistance for the at least one next exercise of the user.

D138 The data-processing system (32) according to the any of the preceding embodiments with the features of D24, wherein the instruction data comprise at least an indication relating to training resistances for a plurality of exercises, comprising the at least one next exercise of the user.

D139 The data-processing system (32) according to any of the preceding data-processing system embodiments with the features of D82, wherein the data-processing system (32) is configured for adapting the user plan data the user plan data relating to the next exercise of the at least one user.

D140 The data-processing system (32) according to any of the preceding data-processing system embodiments with the features of D139, wherein the data-processing system is configured for adapting the user plan data relating to the next exercise of the user based on the heart-rate data relating to at least one of the current and the current as well as at least one preceding user exercise of the user D141 The data-processing system (32) according to any of the preceding data-processing system embodiments with the features of D139, wherein the data-processing system is configured for adapting the user plan data relating to the next exercise of the user based on the heart-rate variability data relating to at least one of the current and the current as well as at least one preceding user exercise of the user D142 The data-processing system (32) according to any of the preceding data-processing system embodiments with the features of D139, wherein the data-processing system is configured for adapting the user plan data relating to the next exercise of the user based on the temporal changes of the heart rate of the user relating to at least one of the current and the current as well as at least one preceding user exercise of the user D143 The data-processing system (32) according to any of the preceding data-processing system embodiments with the features of D139, wherein the data-processing system is configured for adapting the user plan data relating to the next exercise of the user based on the measure for the increase and/or the decrease of the heart-rate of the user relating to at least one of the current and the current as well as at least one preceding user exercise of the user D144 The data-processing system (32) according to any of the preceding data-processing system embodiments with the features of D88-D94, wherein the data-processing system is configured for adapting the user plan data relating to the training resistance of the next exercise of the user based on the respectively specified data relating to at least one of the current and the current as well as at least one preceding user exercise of the user.

S148 The system according to any of the preceding system embodiments, wherein the system comprises a data-processing system according to any of the data-processing system embodiments.

Below, method embodiments will be discussed. These embodiments are abbreviated by the letter "M" followed by a number. Whenever reference is herein made to "method embodiments", these embodiments are meant.

M1 A method, comprising using the at least one training machine assembly.

M2 The method according to the preceding method embodiment, wherein the at least one training machine assembly is according to any of the training machine assembly embodiments.

M3 The method according to any of the preceding method embodiments, wherein the method comprises sensing image data.

M4 The method according to any of the preceding method embodiments, wherein the method comprises using the at least one camera.

M5 The method according to any of the preceding method embodiments, wherein the method comprises controlling the at least one training machine assembly.

M6 The method according to any of the preceding method embodiments, wherein the method further comprises providing at least one training resistance to the user.

M7 The method according to any of the preceding method embodiments, wherein the method further comprises providing at least one of a training force and a training torque to the user by at least one or a plurality of contact elements of the machine.

M8 The method according to any of the two preceding method embodiments, wherein each training resistance, training force and/or training torque comprises a training resistance value.

M9 The method according to any of the preceding method embodiments, wherein the method comprises automatically adjusting the at least one training resistance, training force and/or training torque.

M10 The method according to any of the preceding method embodiments, wherein the method further comprises automatically adjusting the at least one user support element.

M11 The method according to any of the preceding method embodiments, wherein the method comprises detecting the heart-rate of the user.

M12 The method according to the preceding method embodiment, wherein the method comprises detecting the heart-rate of the user by the heart-rate detection component.

M13 The method according to any of the two preceding method embodiments, wherein the method comprises detecting the heart-rate of the user by the heart-rate sensing device M14 The method according to the preceding method embodiment, wherein the method comprises sending data from the heart-rate sensing device to the training machine assembly.

M15 The method according to any of the two preceding method embodiments, wherein the method comprises connecting the heart-rate sensing device to the training machine assembly.

M16 The method according to any of the preceding method embodiments with the features of M11, wherein the method comprises generating the heart-rate data of the user.

M17 The method according to the preceding method embodiment, wherein the method comprises generating the heart-rate data of the user when the heart-rate sensing device is in contact with the user.

M18 The method according to the penultimate method embodiment, wherein the method comprises generating the heart-rate data of the user when the heart-rate detection component is in contact with the user.

M19 The method according to any of the preceding method embodiments, wherein the method comprises using the heart-rate sensing device.

M20 The method according to the preceding method embodiment, wherein the heart-rate sensing device is portable and configured to be worn by the user.

M21 The method according to any of the two preceding method embodiments, wherein the heart-rate sensing device is at least one of a smart watch, a bracelet or another wearable fitness tracker device.

M22 The method according to any of the preceding method embodiments with the features of M12, wherein the heart-rate detection component is mounted to the training machine assembly.

M23 The method according to any of the preceding method embodiments with the features of M12, wherein the heart-rate detection component is configured to be touched by the user.

M24 The method according to any of the preceding method embodiments, wherein the method comprises sensing the heart-rate of the user by the heart-rate detection component.

M25 The method according to any of the preceding method embodiments, wherein the method comprises sensing the heart-rate variability of the user.

M26 The method according to the preceding method embodiment, wherein the method comprises sensing the heart-rate variability of the user by the heart-rate detection component.

M27 The method according to any of the preceding method embodiments, wherein the training machine assembly generates the heart-rate data of the user.

M28 The method according to the preceding method embodiment, wherein the method comprises generating the heart-rate data of the user based at least on the image data.

M29 The method according to the preceding method embodiment, wherein the image data comprise a sequence of images.

M30 The method according to any of the two preceding method embodiments, wherein the image data comprise a timestamped sequence of images.

M31 The method according to any of the preceding method embodiments, wherein the method comprises sensing video data.

M32 The method according to the preceding method embodiment, wherein the method further comprises generating heart-rate data of the user by the training machine assembly based on video data captured by the camera.

M33 The method according to any of the preceding method embodiments with the features of M3, wherein the method comprises capturing the image data with a frequency of at least 6.6 Hz.

M34 The method according to any of the preceding method embodiments with the features of M3, wherein the method comprises capturing the image data with a frequency of at least 7.4 Hz.

M35 The method according to any of the preceding method embodiments, wherein the method comprises generating skeleton data.

M36 The method according to the preceding method embodiment and with the features of M3, wherein the method comprises generating the skeleton data based at least on the image data.

M37 The method according to any of the preceding method embodiments, wherein the method comprises generating skeleton-trajectory data.

M38 The method according to any of the preceding method embodiments with the features of M3 and M37, wherein the method comprises generating the skeleton-trajectory data based at least on the sensed image data.

M39 The method according to any of the preceding method embodiments with the features of M3, wherein the method comprises using boundary conditions.

M40 The method according to the preceding method embodiment, wherein the boundary conditions correspond to a training geometry of the training machine assembly.

M41 The method according to any of the two preceding method embodiments and with the features of M37 and/or M38, wherein the method comprises using the boundary conditions for generating the skeleton-trajectory data based at least one the image data.

M42 The method according to any of the three preceding method embodiments and with the features of M27 and/or M28, wherein the method comprises using the boundary conditions for generating the heart-rate data based at least one the image data.

M43 The method according to any of the four preceding method embodiments and with the features of M35 and/or M36, wherein the method comprises using the boundary conditions for generating the skeleton data based at least one the image data.

M44 The method according to any of the preceding method embodiments with the features of M39, wherein at least one of the boundary conditions are possible positions of at least one part of the body of the user.

M45 The method according to any of the preceding method embodiments with the features of M39, wherein at least one of the boundary conditions is a possible trajectory of at least one movable part of the training machine assembly.

M46 The method according to any of the preceding method embodiments with the features of M39, wherein at least one of the boundary conditions are possible trajectories of at least parts of the body of the user interacting with the training machine assembly.

M47 The method according to any of the preceding method embodiments, wherein the method comprises using a supplementary sensing unit.

M48 The method according to any of the preceding method embodiments, wherein the method comprises sensing the user's training effort.

M49 The method according to the preceding method embodiment, wherein the method comprises sensing the user's training effort by the training resistance(s).

M50 The method according to any of the preceding method embodiments with the features of M47 and M48, wherein the method comprises sensing the user's training effort by the supplementary sensing unit.

M51 The method according to any of the preceding method embodiments, wherein the method comprises using not more than one camera.

M52 The method according to any of the preceding method embodiments, wherein the method comprises sensing the image data with the at least one 2D-camera.

M53 The method according to any of the preceding method embodiments with the features of M3, wherein sensing the image data is sensing the image data with the at least one 2D-camera.

M54 The method according to any of the preceding method embodiments, wherein the at least one camera is at least one 3D-camera.

M55 The method according to any of the preceding method embodiments, wherein the at least one camera is a set of at least one 2D-camera and at least one 3D-camera.

M56 The method according to any of the preceding five method embodiments, wherein at least one of the at least one 2D-camera senses light in the visible spectrum.

M57 The method according to any of the preceding method embodiments with the features of at least one of M54 and M55, wherein the at least one 3D-camera comprises a projected infrared depth camera.

M58 The method according to any of the preceding method embodiments with the features of at least one of M54 and M55, wherein the at least one 3D-camera comprises a time-of-flight depth camera.

M59 The method according to any of the preceding method embodiments with the features of M3, wherein the method comprises combining data of the at least one camera.

M60 The method according to any of the preceding method embodiments with the features of 52, wherein the method comprises combining data of the at least one 2D-camera and the at least one 3D-camera.

M61 The method according to any of the preceding method embodiments, wherein the method comprises outputting data.

M62 The method according to any of the preceding method embodiments, wherein the method comprises using a user interface.

M63 The method according to any of the preceding method embodiments with the features of M61 and M62, wherein the method comprises outputting data by the user interface.

M64 The method according to any of the preceding method embodiments with the features of M27, wherein the method comprises storing the heart-rate data of the user.

M65 The method according to the preceding embodiment, wherein the training machine assembly stores the heart-rate data of the user.

M66 The method according to any of the preceding method embodiments with the features of M27, wherein the method comprises transmitting the heart-rate data of the user.

M67 The method according to the preceding method embodiment, wherein the training machine assembly transmits the heart-rate data of the user.

M68 The method according to any of the preceding method embodiments with the features of M27, wherein the method comprises comparing the heart-rate data of the user to predetermined heart-rate data.

M69 The method according to any of the preceding method embodiments with the features of M27, wherein the method comprises comparing the heart-rate data of the user to at least one of the at least one training resistance value.

M70 The method according to the preceding method embodiment, wherein the training machine assembly compares the heart-rate data of the user to at least one of the at least one training resistance value.

M71 The method according to any of the preceding method embodiments with the features of M27, wherein the method comprises comparing heart-rate data of the user which heart-rate data correspond to different activity levels.

M72 The method according to the preceding method embodiment, wherein the method comprises the training machine assembly comparing the heart-rate data of the user which heart-rate data correspond to different activity levels.

M73 The method according to any of the preceding method embodiments with the features of M27, wherein the method comprises generating the heart-rate comparison data by at least one of
  comparing the heart-rate data of the user to the predetermined heart-rate data,
  comparing the heart-rate data of the user which heart-rate data are corresponding to different activity levels of the user, and
  comparing the heart-rate data of the user to at least one of the at least one training resistance value.

M74 The method according to any of the preceding method embodiments with the features of M27, wherein the method comprises generating the heart-rate comparison data by determining the heart-rate variability.

M75 The method according to any of the preceding method embodiments with the features of M27, wherein the method comprises determining the heart-rate variability based on the heart-rate data.

M76 The method according to any of the preceding method embodiments with the features of M73, wherein the heart-rate comparison data comprise heart-rate variability data.

M77 The method according to any of the preceding method embodiments with the features of M35, wherein the method comprises comparing the skeleton data to the skeleton-reference data and to thus generate the skeleton-comparison data.

M78 The method according to the preceding method embodiment, wherein the training machine assembly compares the skeleton data to the skeleton-reference data.

M79 The method according to any of the preceding method embodiments with the features of M35, wherein the method comprises comparing the skeleton-trajectory data to the skeleton-reference data and to thus generate the trajectory-comparison data.

M80 The method according to the preceding method embodiment, wherein the training machine assembly compares the skeleton-trajectory data to the skeleton-reference data.

M81 The method according to any of the preceding method embodiments, wherein the method comprises transmitting at least one of the heart-rate comparison data, the skeleton-comparison data and the trajectory-comparison data.

M82 The method according to the preceding method embodiment, wherein the training machine assembly transmits the at least one of the heart-rate comparison data, the skeleton-comparison data and the trajectory-comparison data.

M83 The method according to any of the two preceding method embodiments, wherein the method comprises transmitting said data to the data-processing system.

M84 The method according to any of the preceding three method embodiments, wherein the method comprises transmitting said data to the end user computer device.

M85 The method according to the preceding method embodiment, wherein the end user computer device is a portable end user computer device.

M86 The method according to any of the preceding method embodiments with the features of M81, wherein the method comprises transmitting said data to the server system.

M87 The method according to any of the preceding method embodiments with the features of M81, wherein the method comprises transmitting said data to at least one or a plurality of further training machine assemblies.

M88 The method according to any of the preceding method embodiments, wherein the method comprises receiving at least one of the heart-rate comparison data, the skeleton-comparison data and the trajectory-comparison data.

M89 The method according to the preceding method embodiment, wherein the training machine assembly receives the at least one of the heart-rate comparison data, the skeleton comparison data and the trajectory-comparison data.

M90 The method according to any of the two preceding method embodiments, wherein the method comprises receiving said data from the data-processing system.

M91 The method according to any of the two preceding method embodiments, wherein the method comprises receiving said data from the at least one or a plurality of further training machine assemblies.

M92 The method according to any of the preceding method embodiments, wherein the method comprises adjusting the at least one automatically adjustable user support element based on at least one of the skeleton-comparison data and the trajectory-comparison data.

M93 The method according to any of the preceding method embodiments, wherein the method comprises adjusting the at least one training resistance based on at least one of the skeleton-comparison data and the trajectory-comparison data.

M94 The method according to any of the preceding method embodiments with the features of M61, wherein the method comprises outputting data based on at least one of the skeleton-comparison data and the trajectory-comparison data.

M95 The method according to any of the preceding method embodiments with the features of M61, wherein the method comprises outputting data based on the heart-rate comparison data.

M96 The method according to any of the preceding method embodiments, wherein the method comprises receiving user plan data.

M97 The method according to the preceding method embodiment, wherein the training machine assembly receives the user plan data.

M98 The method according to any of the two preceding method embodiments, wherein the method comprises adjusting the training resistance based on the user plan data.

M99 The method according to the preceding method embodiment, wherein the training machine assembly adjusts the training resistance based on the user plan data.

M100 The method according to any of the preceding method embodiments, wherein the method is a method for strength training.

M101 The method according to any of the preceding method embodiments, wherein the method is a method for operating a strength training machine.

M102 The method according to any of the preceding method embodiments, wherein the method is a method for operating the training machine assembly in a circuit training.

M103 The method according to any of the preceding method embodiments, wherein the method comprises performing a user identification step.

M104 The method according to any of the preceding method embodiments, wherein the method comprises using a user identification device.

M105 The method according to any of the preceding method embodiments with the features of M103 and M104, wherein the user identification step comprises using the user identification device.

M106 The method according to any of the preceding method embodiments with the features of M103, wherein the user identification step comprises identifying the user by facial recognition.

M107 The method according to any of the preceding method embodiments with the features of M3, wherein the image data are sensed with the at least one camera.

M108 The method according to any of the preceding method embodiments with the features of M9, where the method comprises adjusting the at least one of the at least one training resistance, training force and/or training torque based on the heart-rate of the user.

M109 The method according to any of the preceding method embodiments with the features of M9, where the method comprises adjusting the at least one of the at least one training resistance, training force and/or training torque based on the heart-rate variability of the user.

M110 The method according to any of the preceding method embodiments, wherein the at least one training machine assembly is a plurality of training machine assemblies and wherein the at least one training resistance is a plurality of training resistances.

M111 The method according to any of the preceding method embodiments, wherein the method comprises performing at least one method step according to any of the preceding method embodiments, wherein the at least one step is performed a plurality of times by different training machine assemblies of the plurality of training machine assemblies.

M112 The method according to any of the preceding method embodiments with the features of M110, wherein the method comprises performing method steps according to any of the method embodiments M1-M109 for each of the training machine assemblies.

M113 The method according to any of the preceding method embodiments with the features of M110, wherein a plurality of the plurality of training machine assemblies (10) are according to any of the training machine assembly embodiments.

M114 The method according to any of the preceding method embodiments with the features of M110, wherein all of the plurality of training machine assemblies (10) are according to any of the training machine assembly embodiments.

M115 The method according to any of the preceding method embodiments with the features of M110, wherein the method comprises transmitting data between the training machine assemblies.

M116 The method according to the preceding method embodiment, wherein the method comprises operating a communication network that links the training machine assemblies.

M117 The method according to any of the preceding method embodiments with the features of M110, wherein the method comprises transmitting data to the server system.

M118 The method according to any of the preceding method embodiments with the features of M110, wherein the method comprises receiving data from the server system.

M119 The method according to any of the preceding method embodiments, wherein the method comprises using the data processing system.

M120 The method according to any of the preceding method embodiments with the features of M119, wherein the method comprises storing the user data.

M121 The method according to the preceding method embodiment, wherein the data processing system stores the user data.

M122 The method according to any of the preceding method embodiments with the features of M119, wherein the data-processing system comprises a plurality of devices that are portable.

M123 The method according to any of the preceding method embodiments with the features of M119, wherein the data-processing system comprises a plurality of data-devices that are configured to be worn, carried and/or hold the by users.

M124 The method according to the preceding method embodiment, wherein the method comprises identifying single users by means of at least one data-device.

M125 The method according to any of the preceding method embodiments with the features of M123, wherein the method comprises storing data on the data-devices.

M126 The method according to any of the preceding method embodiments with the features of M123, wherein the data-devices transmit data.

M127 The method according to any of the preceding method embodiments with the features of M123, wherein the method comprises storing the user data on data-devices.

M128 The method according to any of the preceding method embodiments with the features of M123, wherein the data-devices receive data.

M129 The method according to any of the preceding method embodiments with the features of M123, wherein the data-devices communicate by wired communication.

M130 The method according to any of the preceding method embodiments with the features of M123, wherein the data-devices communicate by wireless communication.

M131 The method according to any of the preceding method embodiments with the features of M110, wherein the method comprises using the at least one camera.

M132 The method according to any of the preceding method embodiments with the features of M131, wherein the at least one camera is a 2D-camera.

M133 The method according to the preceding method embodiment, wherein the method comprises not using more cameras than training machine assemblies.

M134 The method according to any of the preceding method embodiments with the features of M131, wherein the at least one camera is at least one 2D-camera.

M135 The method according to any of the preceding method embodiments with the features of M131, wherein the at least one camera is at least one 3D-camera.

M136 The method according to any of the preceding method embodiments with the features of M131, wherein the at least one camera is a set of at least one 3D-camera and at least one 2D-camera.

M137 The method according to any of the preceding method embodiments with the features of M131, wherein the at least one camera is a set of at least one 3D-camera and a plurality of 2D-cameras.

M138 The method according to any of the preceding method embodiments with the features of M131, wherein the at least one camera is a set of a plurality of 3D-cameras and a plurality of 2D-cameras.

M139 The method according to any of the preceding method embodiments with the features of at least one of M135, M136, M137 and M138, wherein the at least one 3D-camera comprises a time-of-flight depth camera.

M140 The method according to any of the preceding method embodiments with the features of at least one of M135, M136, M137 and M138, wherein the at least one 3D-camera comprises a projected infrared depth camera.

M141 The method according to any of the preceding method embodiments with the features of at least one of M134, M136, M137 and M138, wherein the at least one 2D-camera senses light in the visible spectrum.

M142 The method according to any of the preceding method embodiments with the features of at least one of M134, M136, M137 and M138, wherein at least one 2D-camera senses light in the infrared spectrum.

M143 The method according to any of the preceding method embodiments with the features of at least one of M134, M136, M137 and M138, wherein the at least one 2D-camera senses a reflection of ultrasonic waves and wherein the system comprises a source of ultrasonic waves.

M144 The method according to any of the preceding method embodiments with the features of at least one of M134, M136, M137 and M138, wherein the at least one 2D-camera senses a reflection of radar and wherein the method further comprises emitting radio waves.

M145 The method according to any of the preceding method embodiments with the features of at least one of M134, M136, M137 and M138, wherein the method comprises sensing a reflection of laser light with at least one 2D-camera, and wherein the method comprises emitting laser light.

M146 The method according to any of the preceding method embodiments with the features of M131, wherein a plurality or all of the training machine assemblies that are used are with the features of T31.

M147 The method according to any of the preceding method embodiments with the features of M110, wherein the method comprises generating the heart-rate data of the user.

M148 The method according to any of the preceding method embodiments with the features of M147, wherein the heart-rate data comprise the heart-rate variability data.

M149 The method according to the preceding method embodiment, wherein a plurality of the training machine assemblies that are used in the method are according to any of the training machine assembly embodiments with the features of T13.

M150 The method according to any of the two preceding embodiments, wherein a plurality of the training machine assemblies that are used in the method are according to any of the training machine assembly embodiments with the features of T14.

M151 The method according to any of the preceding method embodiments with the features of M147, wherein the method comprises using a plurality of the heart-rate sensing devices.

M152 The method according to the preceding embodiment, wherein the heart-rate sensing devices generate the heart-rate data when in physical contact to the user.

M153 The method according to any of the preceding method embodiments with the features of M147, wherein at least some or each step of generating the heart-rate data of the user is according to any of the preceding embodiments M28-M34.

M154 The method according to the preceding method embodiment, wherein the heart-rate sensing devices are at least one of smart watches, bracelets or another wearable fitness tracker device configured for heart-rate sensing.

M155 The method according to any of the preceding method embodiments with the features of M151, wherein each data-device comprises at least one of the heart-rate sensing devices.

M156 The method according to any of the preceding method embodiments with the features of M110, wherein the method comprises generating the skeleton data of the user.

M157 The method according to any of the preceding method embodiments with the features of M110, wherein the method comprises generating skeleton data of the user based on the image data captured by at least one of the at least one camera (20).

M158 The method according to any of the preceding method embodiments with the features of M110, wherein the method comprises generating skeleton-trajectory data of the user based on the image data captured by at least one of the at least one camera (20).

M159 The method according to any of the preceding method embodiments with the features of at least one of M147, M157 and M158,
wherein the method comprises generating respectively at least one of the heart-rate data, the generating of the skeleton data and the generating of the skeleton-trajectory data of at least one or a plurality of users using the training machine assemblies; and using the boundary conditions corresponding to the geometries of the respective training machine assemblies.

M160 The method according to the preceding embodiment, wherein at least one of the boundary conditions are possible positions of at least one part of the body of the user using a respective training machine assembly.

M161 The method according to any of the two preceding embodiments, wherein at least one of the boundary conditions are possible trajectories of movable parts of a respective training machine assembly.

M162 The method according to any of the three preceding embodiments, wherein at least one of the boundary conditions are possible trajectories of at least a part of the body of the user interacting with a respective training machine assembly.

M163 The method according to any of the preceding method embodiments with the features of M110, wherein the method comprises sensing efforts of the user at different training machine assemblies.

M164 The method according to the preceding method embodiment, wherein the method comprises sensing efforts of users at different training machine assemblies.

M165 The method according to any of the two preceding method embodiments, wherein the method further comprises the features of M48.

M166 The method according to any of the preceding method embodiments with the features of M110, wherein the method comprises storing data relating to the training-resistance value for at least one user using at least one of the training machine assemblies.

M167 The method according to the preceding method embodiment, wherein the data-processing system stores the data relating to the training-resistance value.

M172 The method according to any of the preceding method embodiments with the features of M166, wherein the method comprises generating the activity data of the user based at least on an interaction of the user with at least one of the training machine assemblies.

M173 The method according to any of the preceding method embodiments with the features of M166, wherein the method comprises generating the heart-rate reference data based on at least one of
the predetermined heart-rate data,
the heart-rate data of the user corresponding to different activity levels of the user,
the heart-rate data of the user corresponding to at least one of the at least one training resistance value,
a comparison of portions or points of the heart-rate data of the user, and
a gradient in the heart-rate data of the user.

M174 The method according to any of the preceding method embodiments with the features of M166, wherein the used training machine assemblies are according to T2 or any depending embodiment of T2.

M175 The method according to any of the preceding method embodiments with the features of M110, wherein the method comprises generating the performance data for at least one user.

M176 The method according to any of the preceding method embodiments with the features of M175, wherein the performance data for the at least one user are generated based at least on the heart-rate data of the at least one user.

M177 The method according to any of the preceding method embodiments with the features of M175, wherein the performance data for the at least one user are generated based at least on the heart-rate variability data of the at least one user.

M178 The method according to any of the preceding method embodiments with the features of M175, wherein the performance data for the at least one user are generated based at least on the heart-rate reference data of the at least one user.

M179 The method according to any of the preceding method embodiments with the features of M175, wherein the performance data for the at least one user are generated based at least on comparing the heart-rate data and the heart-rate reference data.

M180 The method according to any of the preceding method embodiments with the features of M175, wherein the performance data for the at least one user are generated based at least on the skeleton data of the at least one user.

M181 The method according to any of the preceding method embodiments with the features of M175, wherein generating the performance data for the at least one user is based at least on the skeleton-trajectory data of the at least one user.

M182 The method according to any of the preceding method embodiments with the features of M175, wherein generating the performance data for the at least one user is based at least on the training resistance value of the training resistance used by the at least one user.

M183 The method according to any of the preceding method embodiments with the features of M175, wherein generating the performance data for the at least one user is based at least on comparing the change of the activity data and the change of the heart-rate data.

M184 The method according to any of the preceding method embodiments with the features of M175, wherein generating the performance data for the at least one user is based at least on comparing the training resistance value of the training resistance used by the at least one user and the heart-rate reference data.

M185 The method according to any of the preceding method embodiments with the features of M110, wherein the method comprises generating the performance-deviation data for the user.

M186 The method according to the preceding method embodiment and with the features of M175, wherein the performance-deviation data are generated by identifying a deviation in the performance data relating to the user.

M187 The method according to any of the preceding method embodiments with the features of M185, wherein the performance-deviation data comprise data relating to the exhaustion level of the user and wherein the method comprises generating said data relating to the exhaustion level of the user.

M188 The method according to the preceding method embodiment, wherein the method comprises generating the data relating to the exhaustion level of the user at least based on the heart-rate variability data.

M189 The method according to any of the preceding method embodiments with the features of M110, wherein the method comprises generating instruction data.

M190 The method according to any of the preceding method embodiments with the features of M110, wherein the method further comprises outputting the instruction data.

M191 The method according to any of the preceding method embodiments with the features of M110, wherein the method comprises using the at least one user interface.

M192 The method according to any of the preceding method embodiments with the features of M190 and M191, wherein the at least one user interface outputs the instruction data.

M193 The method according to any of the preceding method embodiments with the features of M191, wherein the at least one user interface used in the method is a plurality of user interfaces.

M194 The method according to any of the preceding method embodiments with the features of M189, wherein the instruction data are generated at least based on the performance data.

M195 The method according to any of the preceding method embodiments with the features of M189, wherein the instruction data are generated at least based on the performance-deviation data M196 The method according to any of the preceding method embodiments with the features of M110, wherein the method comprises adjusting at least one of the training resistances.

M197 The method according to any of the preceding method embodiments with the features of M110, wherein the method comprises adjusting all training resistances.

M198 The method according to any of the preceding method embodiments with the features of M110, wherein the method comprises automatically adjusting the at least one user support element.

M199 The method according to the preceding embodiment, wherein the method comprises automatically adjusting a plurality of user support elements.

M200 The method according to any of the two preceding method embodiments, wherein the method comprises automatically adjusting at least one user support element of each of the training machine assemblies.

M201 The method according to any of the three preceding method embodiments, wherein the used training machine assemblies are according to T3.

M202 The method according to any of the preceding method embodiments with the features of M110, wherein at least one or a plurality of the used training machine assemblies are according to T62.

M203 The method according to any of the preceding method embodiments with the features of M196, wherein the method comprises adjusting the at least one training resistance based on the heart-rate data.

M204 The method according to any of the preceding method embodiments with the features of M196, wherein the method comprises adjusting the at least one training resistance based on the heart-rate variability data.

M205 The method according to any of the preceding method embodiments, wherein the method comprises processing the user plan data.

M206 The method according to the preceding method embodiment, wherein the user plan data comprise data relating to at least one user exercise.

M207 The method according to any of the preceding method embodiments with the features of M205, wherein the user plan data comprise data relating to a plurality of user exercises.

M208 The method according to any of the preceding method embodiments with the features of M205, wherein the user plan data comprise the rule data for the user exercise(s).

M209 The method according to any of the preceding method embodiments with the features of M205, wherein the user plan data comprise the parameters for the user exercise(s).

M210 The method according to any of the preceding method embodiments with the features of M205, wherein the user plan data comprise target performance data.

M211 The method according to any of the preceding method embodiments with the features of M205, wherein the user plan data comprise target heart-rate data.

M212 The method according to the preceding method embodiment, wherein the target heart-rate data comprise a target range for the user heart-rate.

M213 The method according to any of the preceding method embodiments with the features of M205, wherein the user plan data comprise the types of the user exercise(s).

M214 The method according to any of the preceding method embodiments with the features of M205, wherein the user plan data comprise an indication of suitable training machine assemblies (10) for each user exercise(s).

M215 The method according to any of the preceding method embodiments with the features of M205, wherein the user plan data comprise an indication of at least one order of the user exercise(s).

M216 The method according to any of the preceding method embodiments with the features of M205, wherein the user plan data comprise data relating to a training resistance for at least one user exercise.

M217 The method according to any of the preceding method embodiments with the features of M205, wherein the user plan data comprise data relating to training resistances for a plurality of the exercises.

M218 The method according to any of the preceding method embodiments with the features of M205, wherein the method comprises receiving the user plan data.

M219 The method according to any of the preceding method embodiments with the features of M205, wherein the method comprises transmitting the user plan data.

M220 The method according to any of the preceding method embodiments with the features of M205, wherein the method comprises adapting the user plan data.

M221 The method according to any of the preceding method embodiments with the features of M220, wherein the adapting the user plan data is based at least on the performance-deviation data of the user.

M222 The method according to any of the preceding method embodiments with the features of M220, wherein the adapting the user plan data is based at least on the heart-rate data.

M223 The method according to any of the preceding method embodiments with the features of M220, wherein the adapting the user plan data is based at least on the heart-rate variability data.

M224 The method according to any of the preceding method embodiments with the features of M220, wherein the adapting the user plan data is based at least on temporal changes of the heart rate of the user.

M225 The method according to any of the preceding method embodiments with the features of M220, wherein the adapting the user plan data is based at least on the measure for the increase or decrease of the heart-rate of the user.

M226 The method according to any of the preceding method embodiments with the features of M205, wherein the user plan data comprise the data relating to the training resistance.

M227 The method according to any of the preceding method embodiments with the features of M220 and M226, wherein adapting the user plan data comprises adapting the data relating to the training resistance.

M228 The method according to any of the preceding method embodiments with the features of M227, wherein the adapting the data relating to the training resistance is based at least on the performance data and the target performance data.

M229 The method according to any of the preceding method embodiments with the features of M227, wherein the adapting the data relating to the training resistance is based at least on the heart-rate variability of the user.

M230 The method according to any of the preceding method embodiments with the features of M227, wherein the adapting the data relating to the training resistance is based at least on the heart-rate data and the target heart-rate data.

M231 The method according to any of the preceding method embodiments with the features of M227, wherein the adapting the data relating to the training resistance is based at least on the measure for the increase or decrease of the heart-rate of the user.

M232 The method according to any of the four preceding method embodiments, wherein the adapting of the data relating to the training resistance is based on history data relating to adapting the training resistance and the change of the respective measure for the user performance.

M233 The method according to the preceding embodiment, wherein the method comprises adapting the data relating to the training resistance based on the history data by a machine-learning algorithm trained with the history data.

M234 The method according to any of the preceding method embodiments with the features of M196, wherein the method comprises adjusting at least one of the training resistances based on at least a portion of the user plan data.

M235 The method according to any of the preceding method embodiments with the features of M189, wherein the method comprises generating the instruction data based on at least a portion of the user plan data.

M236 The method according to any of the preceding method embodiments with the features of M189, wherein the instruction data comprise data relating to a further exercise of the user.

M237 The method according to any of the preceding method embodiments, wherein the method comprises transmitting at least a portion of the performance data.

M238 The method according to any of the preceding method embodiments, wherein the method comprises transmitting at least a portion of the performance-deviation data.

M239 The method according to any of the preceding method embodiments, wherein the method comprises transmitting at least a portion of the heart-rate data.

M240 The method according to any of the preceding method embodiments, wherein the method comprises transmitting at least a portion of the heart-rate reference data.

M241 The method according to any of the preceding method embodiments, wherein the method comprises transmitting at least a portion of the skeleton data.

M242 The method according to any of the preceding method embodiments, wherein the method comprises transmitting at least a portion of the skeleton-trajectory data.

M243 The method according to any of the preceding method embodiments, wherein the method comprises transmitting at least a portion of the instruction data.

M244 The method according to any of the preceding method embodiments, wherein the method comprises transmitting at least a portion of the user plan data.

M245 The method according to any of the preceding embodiments M237-M244, wherein the method comprises transmitting the data to the server system.

M246 The method according to any of the preceding embodiments M237-M245, wherein the method comprises transmitting the data to the end user computer device.

M247 The method according to the preceding embodiment, wherein the end user computer device is portable.

M248 The method according to any of the preceding method embodiments, wherein the method comprises using the end user computer device.

M249 The method according to any of the preceding method embodiments with the features of M246 and M190, wherein the method comprises outputting a portion of the instruction data via the end user computer device.

M250 The method according to any of the preceding method embodiments with the features of M246 and M205, wherein the method comprises outputting a portion of the user plan data.

M251 The method according to any of the preceding method embodiments with the features of M198, wherein the method comprises automatically adjusting the at least one user support element based on the comparison data.

M252 The method according to any of the preceding method embodiments with the features of M251 and M156, wherein
the method comprises comparing the skeleton data to the skeleton-reference data and thus generating skeleton-comparison data, and
wherein the comparison data comprise at least a portion of the skeleton-comparison data.

M253 The method according to any of the preceding method embodiments with the features of M251 and M158, wherein
the method comprises comparing the skeleton-trajectory data to the skeleton-reference data and thus generating trajectory-comparison data, and the comparison data comprise at least a portion of the trajectory-comparison data.

M254 The method according to any of the preceding method embodiments with the features of M251, wherein the method comprises adjusting at least one of the at least one training resistance based on at least one of the comparison data, the skeleton-comparison data and the trajectory-comparison data.

M255 The system according to any of the preceding embodiments with the features of M251 and M189, wherein the method comprises outputting the instruction data based on at least one of the comparison data, the skeleton-comparison data and the trajectory-comparison data.

M256 The method according to any of the preceding embodiments with the features of M110, wherein the method is a method for operating training machine assemblies for strength training.

M257 The method according to any of the preceding embodiments with the features of M110, wherein the method is a method for operating training machine assemblies for circuit training.

M258 The method according to any of the preceding embodiments, wherein the method comprises providing a plurality of different training resistances to the plurality of users at a same time by a plurality of contact elements of the training machine assemblies.

M259 The method according to any of the preceding method embodiments with the features of M110, wherein each of a plurality of the training machine assemblies are according to T66.

M260 The method according to any of the preceding method embodiments with the features of M110, wherein each of the training machine assemblies used in the method is configured for at least one user exercise and wherein at least some of the user exercises are different from each other.

M261 The method according to any of the preceding method embodiments with the features of M196, wherein the method comprises adjusting at least one of the training resistances for a next user exercise of a single user and/or each of the at least one user.

M262 The method according to any of the preceding method embodiments with the features of M261, wherein the method comprises adjusting at least one or all of the training resistances for the next user exercise of at least one of the user(s) based on a portion of the heart-rate data relating to the heart-rate of the respective user during at least one of a current exercise performed by the user and a time between the current exercise of the user and a respectively next exercise of the user.

M263 The method according to any of the preceding method embodiments with the features of M261, wherein the method comprises adjusting at least one or all of the training resistances for the current user exercise of the at least one user based on the heart-rate variability of the at least one user before the current exercise at the training machine assembly.

M264 The method according to any of the preceding method embodiments with the features of M205, wherein the method comprises adapting the user plan data relating to the next exercise of the at least one user.

M265 The method according to any of the preceding method embodiments with the features of M264, wherein the adapting the user plan data relating to the next exercise of the user is based at least on the performance-deviation data relating to at least one of the current and the current as well as at least one preceding user exercise of the user.

M266 The method according to any of the preceding method embodiments with the features of M264, wherein the adapting the user plan data relating to the next exercise of the user is based at least on the heart-rate data relating to at least one of the current and the current as well as the at least one preceding user exercise of the user.

M267 The method according to any of the preceding method embodiments with the features of M264, wherein the adapting of the user plan data relating to the next exercise of the user is based at least on the heart-rate variability data relating a period during the current and the preceding exercise of the user.

M268 The method according to any of the preceding method embodiments with the features of M264, wherein the adapting the user plan data relating to the next exercise of the user is based at least on the temporal changes of the heart rate of the user during at least one of the current and the current as well as at least one preceding user exercise of the user.

M269 The method according to any of the preceding method embodiments with the features of M264, wherein the adapting the user plan data relating to the next exercise of the user is based at least on the measure for the increase and/or the decrease of the heart-rate of the user during at least one of the current and the current as well as at least one preceding user exercise of the user.

M270 The method according to any of the preceding method embodiments with the features of at least one of M226-234, wherein the user plan data comprise data relating to the at least one next training resistance and wherein adapting of the user plan data comprises adapting the data relating to the next training resistance based on the respectively specified data relating to at least one of the current and the current as well as at least one preceding user exercise of the user.

Below, data-processing method embodiments will be discussed. These embodiments are abbreviated by the letter "DM" followed by a number. Whenever reference is herein made to "data-processing method embodiments", these embodiments are meant.

DM1 A method, comprising
receiving data,
sending data, and
processing data.

DM2 The method according to any of the preceding data-processing method embodiments, wherein the method is a computer-implemented method.

DM3 The method according to any of the preceding data-processing method embodiments, wherein the method comprises using a data-processing system.

DM4 The method according to any of the preceding data-processing method embodiments, wherein the data-processing system comprises at least one end user computer device.

DM5 The method according to any of the preceding data-processing method embodiments, wherein the data-processing system comprises the server system.

DM6 The method according to any of the preceding data-processing method embodiments, wherein the method comprises receiving user plan data.

DM7 The method according to any of the preceding data-processing method embodiments, wherein the method comprises generating the user plan data.

DM8 The method according to any of the preceding data-processing method embodiments, wherein the method comprises storing the user plan data.

DM9 The method according to any of the preceding data-processing method embodiments with the features of at least one of DM6, DM7 and DM8, wherein the user plan data comprise data relating to at least one user exercise.

DM10 The method according to any of the preceding data-processing method embodiments with the features of at least one of DM6, DM7 and DM8, wherein the user plan data comprise data relating to a plurality of user exercises.

DM11 The method according to any of the preceding data-processing method embodiments with the features of at least one of DM6, DM7 and DM8, wherein the user plan data comprise rule data for the user exercise(s).

DM12 The method according to any of the preceding data-processing method embodiments with the features of at least one of DM6, DM7 and DM8, wherein the user plan data comprise parameters for the user exercise(s).

DM13 The method according to any of the preceding data-processing method embodiments with the features of at least one of DM6, DM7 and DM8, wherein the user plan data comprise the target performance data.

DM14 The method according to any of the preceding data-processing method embodiments with the features of at least one of DM6, DM7 and DM8, wherein the user plan data comprise the target heart-rate data.

DM15 The method according to any of the preceding data-processing method embodiments with the features of DM13 and DM14, wherein the target performance data comprise the target heart-rate data.

DM16 The method according to any of the preceding data-processing method embodiments with the features of any of the two preceding embodiments, wherein the target heart-rate data comprise a target range for the user heart-rate.

DM17 The data-processing system (32) according to any of the preceding data-processing system embodiments with the features of at least one of D2, D3 and D4, wherein the user plan data comprise types of the user exercise(s).

DM18 The method according to any of the preceding data-processing method embodiments with the features of at least one of DM6, DM7 and DM8, wherein the user plan data comprise an indication of suitable training machine assemblies (10) for each user exercise.

DM19 The method according to any of the preceding data-processing method embodiments with the features of at least one of DM6, DM7 and DM8, wherein the user plan data comprise an indication of at least one order of the user exercise(s).

DM20 The method according to any of the preceding data-processing method embodiments with the features of at least one of DM6, DM7 and DM8, wherein the user plan data comprise data relating to a training resistance for at least one exercise.

DM21 The method according to any of the preceding data-processing method embodiments with the features of at least one of DM6, DM7 and DM8, wherein the user plan data comprise data relating to the training resistances for a plurality of exercises.

DM22 The method according to any of the preceding data-processing method embodiments, wherein the method comprises processing instruction data.

DM23 The method according to the preceding embodiment, wherein the method comprises generating the instruction data.

DM24 The method according to the preceding embodiment, wherein the generating the instruction data comprises selecting the instruction data from a set of instruction data.

DM25 The method according to any of the preceding data-processing method embodiments with the features of DM22, wherein the method comprises outputting the instruction data.

DM26 The method according to any of the preceding data-processing method embodiments with the features of DM22, wherein the method comprises sending the instruction data.

DM27 The method according to any of the preceding data-processing method embodiments with the features of DM22, wherein the method comprises generating the instruction data based on the user plan data.

DM28 The method according to any of the preceding data-processing method embodiments with the features of DM22, wherein the instruction data comprise at least an indication relating to the training resistance for an exercise.

DM29 The method according to any of the preceding data-processing method embodiments with the features of DM22, wherein the instruction data comprise at least an indication relating to the training resistances for a plurality of exercises.

DM30 The method according to any of the preceding data-processing method embodiments, wherein the method comprises controlling at least one training resistance of the at least one training machine assembly.

DM31 The method according to the preceding data-processing method embodiment, wherein the at least one training machine assembly is according to any of the training machine assembly embodiments.

DM32 The method according to any of the two preceding embodiments, wherein the at least one training machine assembly is a plurality of training machine assemblies and the at least one training resistance is a plurality of training resistances.

DM33 The method according to any of the three preceding embodiments, wherein the method comprises controlling the at least one training resistance based on the user plan data.

DM34 The method according to any of the three preceding embodiments, wherein controlling the at least one training resistance is based on the instruction data.

DM35 The method according to any of the four preceding embodiments, wherein the method comprises controlling the at least one training machine assembly by sending data to the at least one training machine assembly by the data-processing system.

DM36 The method according to any of the five preceding embodiments, wherein the method comprises controlling the at least one training machine assembly by sending data to the at least one training machine assembly by the server system.

DM37 The method according to any of the five preceding embodiments, wherein the method comprises controlling the at least one training machine assembly by sending data to the at least one training machine assembly by the at least one end user computer device.

DM38 The method according to any of the preceding data-processing method embodiments, wherein the method comprises storing heart-rate data of the at least one user.

DM39 The method according to any of the preceding data-processing method embodiments, wherein the method comprises processing the heart-rate data of the at least one user.

DM40 The method according to any of the preceding data-processing method embodiments, wherein the method comprises generating the heart-rate data of the at least one user.

DM41 The method according to any of the preceding data-processing method embodiments, wherein the method comprises storing heart-rate variability data of the at least one user.

DM42 The method according to any of the preceding data-processing method embodiments, wherein the method comprises processing the heart-rate variability data of the at least one user.

DM43 The method according to any of the two preceding embodiments, wherein the method comprises generating the heart-rate variability data of the at least one user.

DM44 The method according to any of the preceding data-processing method embodiments with the features of DM38, wherein the method comprises determining the temporal changes of the heart rate of the user.

DM45 The method according to any of the preceding data-processing method embodiments with the features of DM38, wherein the method comprises processing the temporal changes of the heart rate of the user.

DM46 The method according to any of the preceding data-processing method embodiments with the features of DM38, wherein the method comprises determining the measure for an increase or decrease of the heart-rate of the user.

DM47 The method according to any of the preceding data-processing method embodiments with the features of DM38, wherein the method comprises processing the measure for the increase and/or decrease of the heart-rate of the user.

DM48 The method according to any of the preceding data-processing method embodiments, wherein the method comprises generating and/or receiving image data of the at least one user.

DM49 The method according to any of the preceding data-processing method embodiments, wherein the method comprises generating and/or receiving skeleton data of the at least one user.

DM50 The method according to any of the preceding data-processing method embodiments, wherein the method comprises generating and/or receiving skeleton-trajectory data of the at least one user.

DM51 The method according to any of the preceding data-processing method embodiments with the features of DM48, wherein the method comprises generating the skeleton data of the user based on the image data of the user.

DM52 The method according to any of the preceding data-processing method embodiments with the features of DM48, wherein the method comprises generating the skeleton-trajectory data of the user based on the image data of the user.

DM53 The method according to any of the preceding data-processing method embodiments with the features of DM48, wherein the method comprises generating the heart-rate data of the user based on the image data of the user.

DM54 The method according to any of the preceding data-processing method embodiments with the features of at least one of DM51, DM52 and DM53, wherein the method comprises using at least one boundary condition for generating the skeleton data of the user, wherein the boundary condition is corresponding to an exercise of the user and/or a training machine assembly that the user uses.

DM55 The method according to any of the preceding data-processing method embodiments with the features of at least one of DM51, DM52 and DM53, wherein the method comprises using at least one boundary condition for generating the skeleton-trajectory data of the user, wherein the boundary condition is corresponding to the exercise of the user and/or the training machine assembly that the user uses.

DM56 The method according to any of the preceding data-processing method embodiments with the features of DM53, wherein the method comprises using at least one boundary condition corresponding to an exercise of the user for generating the heart-rate data of the user.

DM57 The method according to any of the three preceding embodiments, wherein the at least one boundary condition relates to a training machine assembly used to perform the user exercise.

DM58 The method according to any of the four preceding embodiments, wherein at least one boundary condition relates to possible positions of at least one part of the body of the user using the training machine assembly.

DM59 The method according to any of the five preceding embodiments, wherein at least one boundary condition relates to possible trajectories of movable parts of a respective training machine assembly.

DM60 The method according to any of the six preceding embodiments, wherein at least one boundary condition relates to possible trajectories of at least parts of the body of the user interacting with the respective training machine assembly.

DM61 The method according to any of the preceding data-processing method embodiments, wherein the method comprises processing performance data.

DM62 The method according to any of the preceding data-processing method embodiments, wherein the method comprises storing the performance data.

DM63 The method according to any of the preceding data-processing method embodiments, wherein the method comprises generating the performance data.

DM64 The method according to any of the preceding data-processing method embodiments with the features of DM63, wherein the method comprises generating the performance data for the at least one user based at least on the heart-rate data of the at least one user.

DM65 The method according to any of the preceding data-processing method embodiments with the features of DM63, wherein the method comprises generating the performance data for the at least one user based at least on the heart-rate variability data of the at least one user.

DM66 The method according to any of the preceding data-processing method embodiments with the features of DM63, wherein the method comprises generating the performance data for the at least one user based at least on the heart-rate reference data of the at least one user.

DM67 The method according to any of the preceding data-processing method embodiments with the features of DM63, wherein the method comprises generating the performance data for the at least one user based furthermore on comparing the heart-rate data and the heart-rate reference data of the user.

DM68 The method according to any of the preceding data-processing method embodiments with the features of DM63, wherein the method comprises generating the performance data for the at least one user based at least on the skeleton data of the at least one user.

DM69 The method according to any of the preceding data-processing method embodiments, wherein the method comprises processing history data.

DM70 The method according to any of the preceding data-processing method embodiments, wherein the method comprises receiving the history data.

DM71 The method according to any of the preceding data-processing method embodiments, wherein the method comprises generating the history data.

DM72 The method according to any of the preceding data-processing method embodiments, wherein the method comprises storing the history data.

DM73 The method according to any of the preceding four embodiments, wherein the history data relate to a plurality of users.

DM74 The method according to any of the preceding data-processing method embodiments with the features of at least one of DM69, DM70, DM71 and DM72, wherein the history-data comprise data relating to the training resistances.

DM75 The method according to any of the preceding data-processing method embodiments with the features of at least one of DM69, DM70, DM71 and DM72, wherein the history-data comprise data relating to the at least one training resistance for at least one exercise and/or to the training resistances for a plurality of exercises.

DM76 The method according to any of the preceding data-processing method embodiments with the features of at least one of DM69, DM70, DM71 and DM72, wherein the history-data comprise heart-rate data.

DM77 The method according to any of the preceding data-processing method embodiments with the features of at least one of DM69, DM70, DM71 and DM72, wherein the history-data comprise heart-rate variability data.

DM78 The method according to any of the preceding data-processing method embodiments with the features of at least one of DM69, DM70, DM71 and DM72, wherein the history-data comprise data relating to at least one of
the temporal changes of the heart rate of the user, and
the measure for the increase and/or decrease of the heart-rate of the user.

DM79 The method according to any of the preceding data-processing method embodiments with the features of at least one of DM69, DM70, DM71 and DM72, wherein the history-data comprise instruction data.

DM80 The method according to any of the preceding data-processing method embodiments with the features of at least one of DM69, DM70, DM71 and DM72, wherein the history-data comprise skeleton data.

DM81 The method according to any of the preceding data-processing method embodiments with the features of at least one of DM69, DM70, DM71 and DM72, wherein the history-data comprise skeleton-trajectory data.

DM82 The method according to any of the preceding data-processing method embodiments with the features of at least one of DM69, DM70, DM71 and DM72, wherein the history-data comprise performance data.

DM83 The method according to any of the preceding data-processing method embodiments, wherein the method comprises receiving reference data.

DM84 The method according to any of the preceding data-processing method embodiments, wherein the method comprises processing the reference data.

DM85 The method according to any of the preceding data-processing method embodiments, wherein the method comprises generating the reference data.

DM86 The method according to any of the preceding data-processing method embodiments, wherein the method comprises storing the reference data.

DM87 The method according to any of the preceding data-processing method embodiments, wherein the method comprises generating comparison data.

DM88 The method according to any of the preceding data-processing method embodiments, wherein the method comprises storing the comparison data.

DM89 The method according to any of the preceding data-processing method embodiments, wherein the method comprises processing the comparison data.

DM90 The method according to any of the preceding data-processing method embodiments, wherein the method comprises receiving the comparison data.

DM91 The method according to any of the preceding data-processing method embodiments with the features of DM87, wherein the method comprises generating the comparison data by comparing data relating to the user to reference data.

DM92 The method according to any of the preceding data-processing method embodiments with the features of at least one of DM83, DM84, D70 and D71, wherein the reference data comprise skeleton-reference data.

DM93 The method according to any of the preceding data-processing method embodiments with the features of DM87 and DM92, wherein the comparison data comprise skeleton-comparison data and wherein the method comprises generating the skeleton-comparison data by comparing the skeleton data to the skeleton reference-data.

DM94 The method according to any of the preceding data-processing method embodiments with the features of DM87 and DM92, wherein the comparison data comprise trajectory-comparison data and the method comprises generating the trajectory-comparison data by comparing the skeleton-trajectory data to the skeleton reference-data.

DM95 The method according to any of the preceding data-processing method embodiments with the features of at least one of DM83, DM84, D70 and D71, wherein the reference data comprise heart-rate reference data.

DM96 The method according to any of the preceding data-processing method embodiments with the features of DM87 and DM95, wherein the comparison data comprise heart-rate comparison data and the method comprises generating the heart-rate comparison data by comparing the heart-rate data to the heart-rate reference data.

DM97 The method according to any of the preceding data-processing method embodiments, wherein the method comprises adapting the user plan data.

DM98 The method according to any of the preceding data-processing method embodiments with the features of DM97 and DM3, wherein the data-processing system adapts the user plan data.

DM99 The method according to any of the preceding data-processing method embodiments with the features of DM97 and at least one of DM3 and DM5, wherein the server system adapts the user plan data.

DM100 The method according to any of the preceding data-processing method embodiments with the features of DM97, wherein the method comprises adapting the user plan data based on the heart-rate data.

DM101 The method according to any of the preceding data-processing method embodiments with the features of DM97, wherein the method comprises adapting the user plan data based on the heart-rate variability data.

DM102 The method according to any of the preceding data-processing method embodiments with the features of DM97, wherein the method comprises adapting the user plan data based on the temporal changes of the heart rate of the user.

DM103 The method according to any of the preceding data-processing method embodiments with the features of DM97, wherein the method comprises adapting the user plan data based on the measure for the increase or decrease of the heart-rate of the user.

DM104 The method according to any of the preceding data-processing method embodiments with the features of DM97, wherein the method comprises adapting the user plan data based on the skeleton data.

DM105 The method according to any of the preceding data-processing method embodiments with the features of DM97, wherein the method comprises adapting the user plan data based on the skeleton-trajectory data.

DM106 The method according to any of the preceding data-processing method embodiments with the features of DM97 and with the features of at least one DM61, DM62 and DM63, wherein the method comprises adapting the user plan data based on the performance data.

DM107 The method according to any of the preceding data-processing method embodiments with the features of DM97 and DM13, wherein the method comprises adapting the user plan data based on the target performance data.

DM108 The method according to any of the preceding data-processing method embodiments with the features of DM97 and at least one of DM69, DM70, DM71 and DM72, wherein the method comprises adapting the user plan data based on the history data.

DM109 The method according to any of the preceding data-processing method embodiments with the features of DM33 and DM97, wherein the method comprises controlling the at least one training resistance based on the adapted user plan data.

DM110 The method according to any of the preceding data-processing method embodiments with the features of DM33 and at least one of DM87-DM90, wherein the method comprises controlling the at least one training resistance based on the comparison data.

DM111 The method according to any of the preceding data-processing method embodiments with the features of DM97 and at least one of DM22 and DM23, wherein the method comprises adapting the instruction data based on the adapted user plan data.

DM112 The method according to any of the preceding data-processing method embodiments with the features of at least one of DM87-DM90 and at least one of DM22 and DM23, wherein the method comprises adapting the instruction data based on the comparison data.

DM113 The method according to any of the preceding data-processing method embodiments with the features of at least one of DM69-DM72, wherein the method comprises adapting the instruction data and/or the user plan data based on the history data.

DM114 The method according to the preceding data-processing method embodiment, wherein the data-process system adapts the instruction data and/or the user plan data based on the history data.

DM115 The method according to any of the preceding two data-processing method embodiments, wherein the method comprises applying at least one machine learning algorithm to the history data.

DM116 The method according to the preceding data-processing method embodiment, wherein the data-processing system applies the at least one machine learning algorithm to the history data.

DM117 The method according to any of the preceding data-processing method embodiments with the features of DM113, wherein the method comprises applying at least one pattern recognition algorithm to the history data.

DM118 The method according to the preceding data-processing method embodiment, wherein the data-processing system applies the at least one pattern recognition algorithm to the history data.

DM119 The method according to any of the preceding data-processing method embodiments with the features of DM113, wherein the method comprises applying at least one reinforcement-learning algorithm to the history data.

DM120 The method according to the preceding embodiment, wherein data-processing system applies the at least one reinforcement-learning algorithm to the history data.

DM121 The method according to any of the preceding data-processing method embodiments with the features of DM115, wherein the method comprises applying at least one neural-network algorithm to the history data.

DM122 The method according to the preceding embodiment, wherein the data-processing system applies the at least one neural-network algorithm to the history data.

DM123 The method according to any of the preceding data-processing method embodiments, wherein the method comprises connecting the data-processing system to the at least one heart-rate sensing device.

DM124 The method according to any of the preceding data-processing method embodiments with the features of DM4, wherein the method comprises connecting the at least one end user computer device to the at least one heart-rate sensing device.

DM125 The method according to any of the preceding data-processing method embodiments with the features of DMS, wherein the method comprises connecting the server system to the at least one heart-rate sensing device.

DM126 The method according to any of the preceding data-processing method embodiments with the features of D3, wherein the data-processing system comprises the at least one heart-rate sensing device.

DM127 The method according to any of the preceding data-processing method embodiments with the features of D4, wherein the at least one end user computer device comprises the at least one heart-rate sensing device.

DM128 The method according to any of the preceding data-processing method embodiments with the features of at least one of DM123, DM126 and DM127, wherein the at least one heart-rate sensing device is a plurality of heart-rate sensing devices.

DM129 The method according to any of the preceding data-processing method embodiments with the features of DM127 and DM128, wherein at least one of the at least one end user computer device comprises a heart-rate sensing device.

DM130 The method according to any of the preceding data-processing method embodiments with the features of DM129 and DM130, wherein each of the at least one end user computer device comprises a heart-rate sensing device.

DM131 The method according to any of the preceding data-processing method embodiments, wherein the method comprises sensing the heart rate of the at least one user.

DM132 The method according to any of the preceding data-processing method embodiments with the features of DM3, wherein the method comprises sensing the heart rate of the at least one user by means of the data-processing system.

DM133 The method according to any of the preceding data-processing method embodiments with the features of DM4, wherein the method comprises sensing the heart rate of at least one user by means of the at least one end user computer device.

DM134 The method according to any of the preceding data-processing method embodiments, wherein the method comprises sensing the heart-rate variability of the at least one user.

DM135 The method according to any of the preceding data-processing method embodiments with the features of DM3, wherein the method comprises sensing the heart-rate variability of the at least one user by means of the data-processing system.

DM136 The method according to any of the preceding data-processing method embodiments with the features of DM4, wherein the method comprises sensing the heart-rate variability of the at least one user by means of the at least one end user computer device.

DM137 The method according to any of the preceding data-processing method embodiments with the features of DM4, wherein the method comprises sensing the heart-rate variability of the at least one user by means of the at least one heart-rate sensing device.

DM138 The method according to any of the preceding data-processing method embodiments, wherein the method comprises receiving data from at least one wearable device.

DM139 The method according to any of the preceding data-processing method embodiments, wherein the method comprises using the at least one wearable device.

DM140 The method according to the preceding embodiment, wherein the at least one wearable device is a plurality of wearable devices.

DM141 The method according to any of the three preceding embodiments, wherein each of the at least one wearable device comprises a heart-rate sensing device.

DM142 The method according to any of the preceding data-processing method embodiments with the features of DM140 and/or DM141, wherein the method comprises sensing the heart-rate of the at least one user by means of the at least one wearable device.

DM143 The method according to any of the preceding data-processing method embodiments with the features of DM140 and/or DM141, wherein the method comprises sensing the heart-rate variability of the at least one user by means of the at least one wearable device.

DM144 The method according to any of the preceding data-processing method embodiments with the features of DM4, wherein the at least one end user computer device is portable.

DM145 The method according to any of the preceding data-processing method embodiments with the features of DM4, wherein the end user computer device is a smart mobile device.

DM146 The method according to any of the preceding data-processing method embodiments with the features of DM2, wherein the method comprises sending data to a third system.

DM147 The method according to the preceding embodiment, wherein the data-processing system sends the data to the third system.

DM148 The method according to any of the preceding data-processing method embodiments with the features of DM146, wherein the data to be sent to the third system comprise heart-rate data.

DM149 The method according to any of the preceding data-processing method embodiments with the features of DM146, wherein the data to be sent to the third system comprise performance data.

DM150 The method according to any of the preceding data-processing method embodiments with the features of DM146, wherein the data to be sent to the third system comprise instruction data.

DM151 The method according to any of the preceding data-processing method embodiments with the features of DM146, wherein the data to be sent to the third system comprise data relating to the at least one training resistance.

DM152 The method according to any of the preceding data-processing method embodiments with the features of DM146, wherein the data to be sent to the third system comprise performance data.

DM153 The method according to any of the preceding data-processing method embodiments with the features of DM146, wherein the data to be sent to the third system comprise comparison data.

DM154 The method according to any of the preceding data-processing method embodiments, wherein the method comprises receiving data.

DM155 The method according to the preceding embodiment and with the features of DM3, wherein the data-processing system receives the data.

DM156 The method according to any of the preceding data-processing method embodiments with the features of DM154, wherein the data to be received comprise heart-rate data.

DM157 The method according to any of the preceding data-processing method embodiments with the features of DM154, wherein the data to be received comprise data relating to the at least one training resistance.

DM158 The method according to any of the preceding data-processing method embodiments with the features of DM154, wherein the data to be received comprise heart-rate variability data.

DM159 The method according to any of the preceding data-processing method embodiments with the features of DM154, wherein the data to be received comprise history data.

DM160 The method according to any of the preceding data-processing method embodiments with the features of DM3, wherein the method comprises connecting the at least one training machine assembly to the data-processing system.

DM161 The method according to any of the preceding data-processing method embodiments with the features of DM3, wherein the method comprises connecting the data-processing system to a system according to any of the system embodiments.

DM162 The method according to any of the preceding data-processing method embodiments with the features of DM4, wherein the at least one end user computer device is a plurality of end user computer devices.

DM163 The method according to any of the preceding data-processing method embodiments, wherein the method comprises processing data relating to a plurality of users.

DM164 The method according to any of the preceding data-processing method embodiments, wherein the method comprises receiving the data relating to the plurality of users.

DM165 The method according to any of the preceding data-processing method embodiments, wherein the method comprises storing the data relating to the plurality of users.

DM166 The method according to any of the preceding data-processing method embodiments, wherein the method comprises generating data relating to a plurality of users.

DM167 The method according to any of the preceding data-processing method embodiments, wherein the at least one user is a plurality of users.

DM168 The method according to any of the preceding data-processing method embodiments with the features of DM20, wherein the user plan data comprise data relating to a training resistance for at least one respectively next exercise of the at least one user.

DM169 The method according to any of the preceding data-processing method embodiments with the features of DM21, wherein the user plan data comprise data relating to the training resistances for a plurality of exercises, comprising the respectively next exercise of the at least one user.

DM170 The method according to any of the preceding data-processing method embodiments with the features of DM22, wherein the instruction data comprise at least an indication relating to the training resistance for the at least one respectively next exercise of the at least one user.

DM171 The method according to any of the preceding data-processing method embodiments with the features of DM22, wherein the instruction data comprise at least an indication relating to the training resistances for a plurality of exercises, comprising the respectively next exercise of the at least one user.

DM172 The method according to any of the preceding data-processing method embodiments, wherein the method comprises controlling at least one training resistance of the at least one training machine assembly.

DM173 The method according to any of the preceding data-processing method embodiments with the features of DM97, wherein the method comprises adapting the user plan data relating to the next exercise of the at least one user.

DM174 The method according to any of the preceding data-processing method embodiments with the features of DM173, wherein the method comprises adapting the user plan data relating to the next exercise of the user is based at least on the performance-deviation data relating to at least one of the current and the current as well as at least one preceding user exercise of the user.

DM175 The method according to any of the preceding data-processing method embodiments with the features of DM173, wherein the method comprises adapting the user plan data relating to the next exercise of the user is based at least on the heart-rate data relating to at least one of the current and the current as well as at least one preceding user exercise of the user.

DM176 The method according to any of the preceding data-processing method embodiments with the features of DM173, wherein the method comprises adapting the user plan data relating to the next exercise of the user is based at least on the heart-rate variability data relating to the period during the current and the next and/or the preceding and the current user exercise.

DM177 The method according to any of the preceding data-processing method embodiments with the features of DM173, wherein the method comprises adapting the user plan data relating to the next exercise of the user is based at least on the temporal changes of the heart rate of the user during at least one of the current and the current as well as at least one preceding user exercise of the user.

DM178 The method according to any of the preceding data-processing method embodiments with the features of DM173, wherein the method comprises adapting the user plan data relating to the next exercise of the user is based at least on the measure for the increase and/or the decrease of the heart-rate of the user during at least one of the current and the current as well as at least one preceding user exercise of the user.

DM179 The method according to any of the preceding data-processing method embodiments with the features of DM104-110, wherein the user plan data comprise data relating to the at least one next training resistance and wherein adapting of the user plan data comprises adapting the data relating to the next training resistance based on the respectively specified data relating to at least one of the current and the current as well as at least one preceding user exercise of the user.

BRIEF FIGURE DESCRIPTION

DETAILED FIGURE DESCRIPTION

Figure 1:
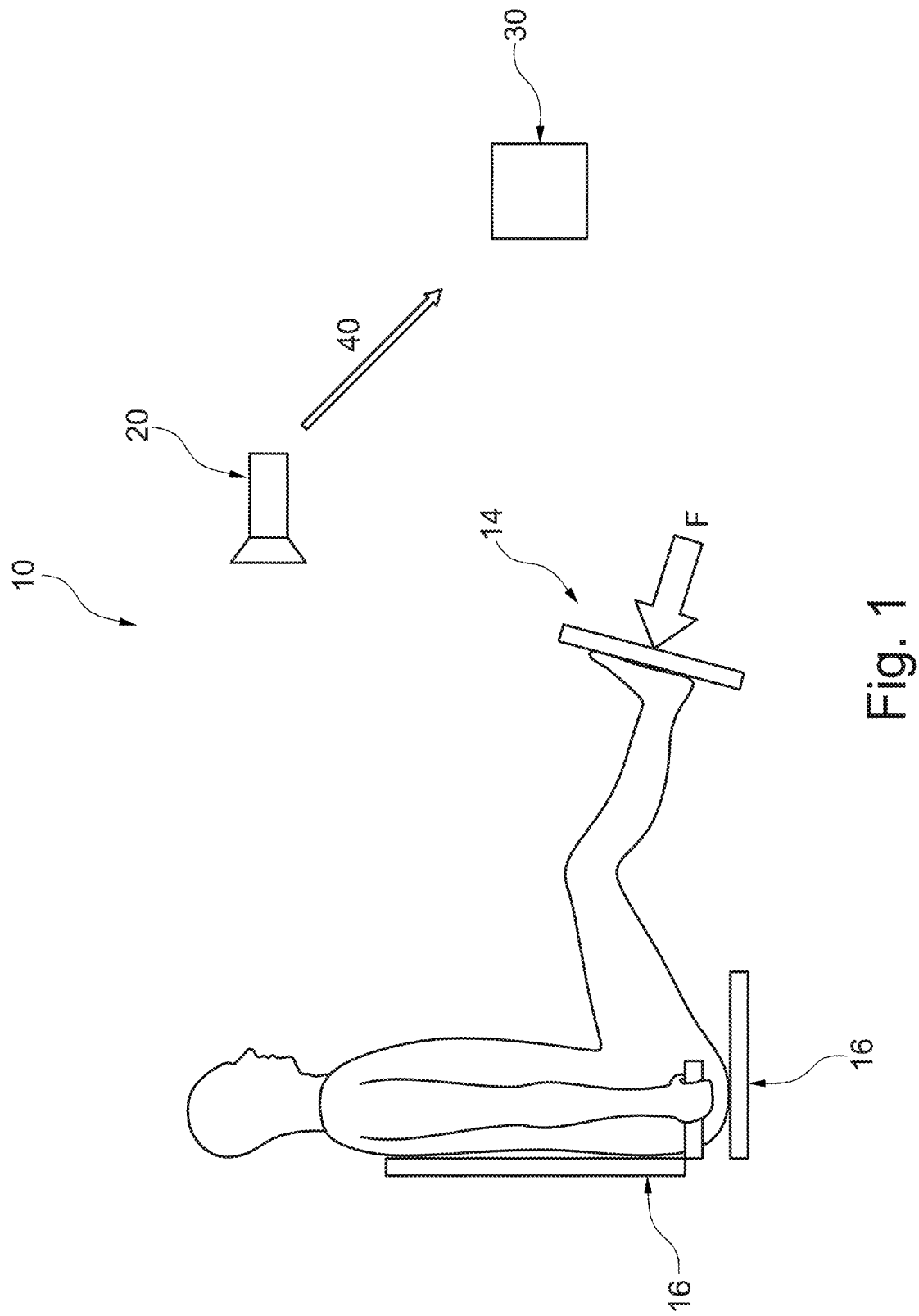
FIG. 1 shows a user training at a training machine assembly.

FIG. 1 shows a user using a training machine assembly 10. The training machine assembly 10 comprises at least one user support element 16. The training machine assembly in this case is a leg press, however, the exact training machine assembly is merely exemplary. For example, the training machine assembly can be a training machine assembly for strength training.

In FIG. 1, the at least one user support element 16 are two user support elements: A seat on which the user sits, as well as a back rest. The user support element can be automatically adjusted by the training machine assembly.

The training machine assembly further comprises a contact element, here, a sliding foot rest, to which the training resistance 14 is applied. The training resistance 14 can be for example generated by at least one of an electric motor, a pneumatic or a hydraulic cylinder and weight stack. Here, the training resistance 14 is a force, indicated by the letter F in FIG. 1.

The training machine assembly 10 further comprises a camera 20. The camera 20 captures image data 40 of the user using the training machine assembly. The image data 40 that the camera captures can be video data.

The training machine assembly 10 further comprises a control device 30. However, the training machine assembly can also only be connected to the control device 30, for example in a case where there is a system comprising a plurality of training machine assemblies and the system comprises at least one control device 30 controlling the training machine assemblies 10.

The camera 20 is configured to transmitting the image data 40 to the control device 30. However, the camera can also be configured for transmitting the image data 40 to a data processing system 32.

Figure 2:
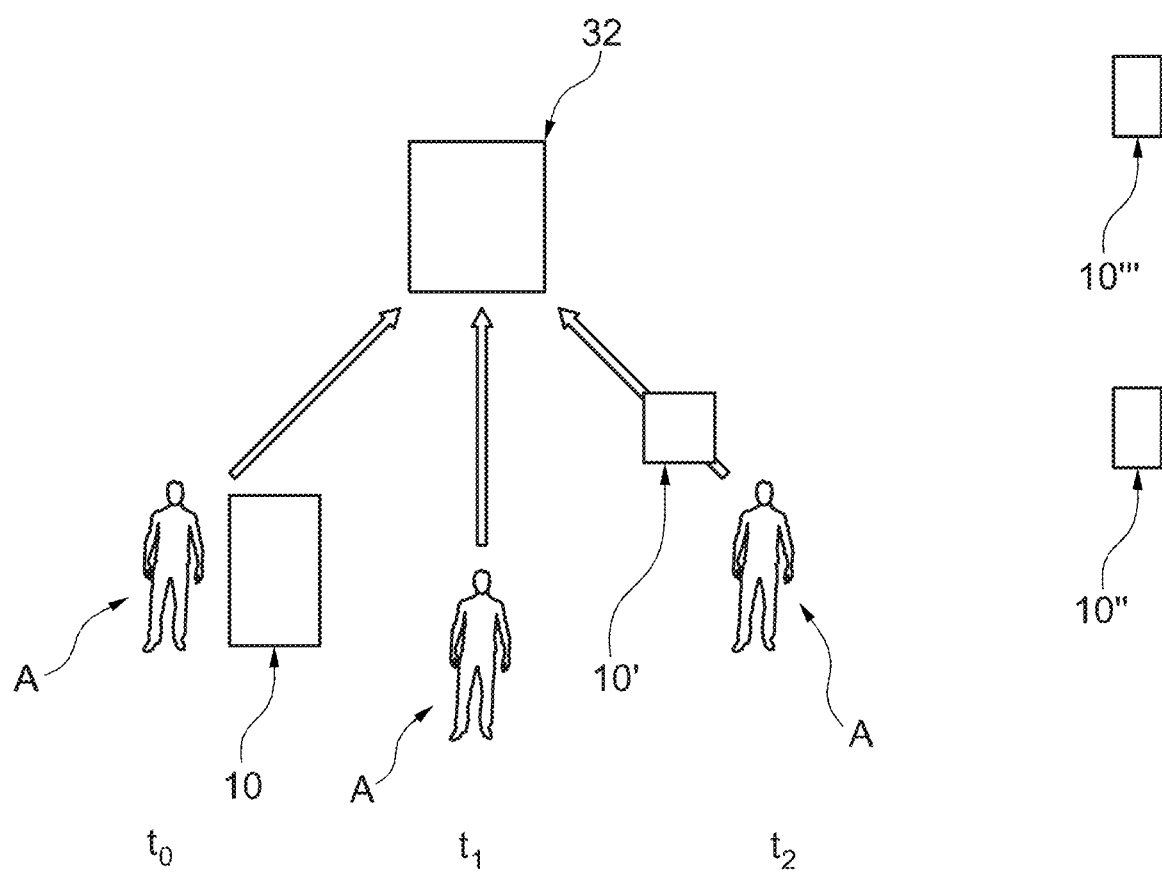
FIG. 2 shows a user at different points in time using a system in a circuit training.

FIG. 2 shows a system, comprising four training machine assemblies 10, 10', 10" and 10'". FIG. 2 further shows the user, indicated by the letter A, at three different points in time, $t_0$, $t_1$ and $t_2$. The system is set up for circuit training.

The user starts to exercise at t0 at the training machine assembly 10. The user then goes to the second machine 10', for example t1, where he rests and then continues training, for example at t2. The user continues this training mode also for the following training machine assemblies 10" and 10'". In FIG. 2, four training machine assemblies 10 are shown, however, there could also be more or less training machine assemblies, and the user can interact with all or just with some of them.

While the user exercises, the training machine assembly 10, 10', 10", 10'" generates data, for example regarding the heart-rate of the user or regarding a proper exercising style, as will be discussed in the context of FIG. 3. The training machine assemblies can for example also generate image data 40, as discussed in the context of FIG. 1. The training machine assemblies transmit these data to the data-processing system 32.

The system is configured to operate based on the generated data.

For example, when the user exercises improperly, the system can instruct the user to exercise properly. The system can be configured for outputting corresponding instruction data in such a case. The system can also be configured for generating corresponding instruction data in such a case.

The system can also be configured for adapting the training resistances of the training machine assemblies based on the generated data.

The system can be configured for generating further data based on the image data, such as heart-rate data corresponding to the user, skeleton data, which may refer to a physiology of the user, and skeleton-trajectory data, which may refer to a trajectory of parts or portions of the body of the user, for example to joints of the user.

Figure 3:
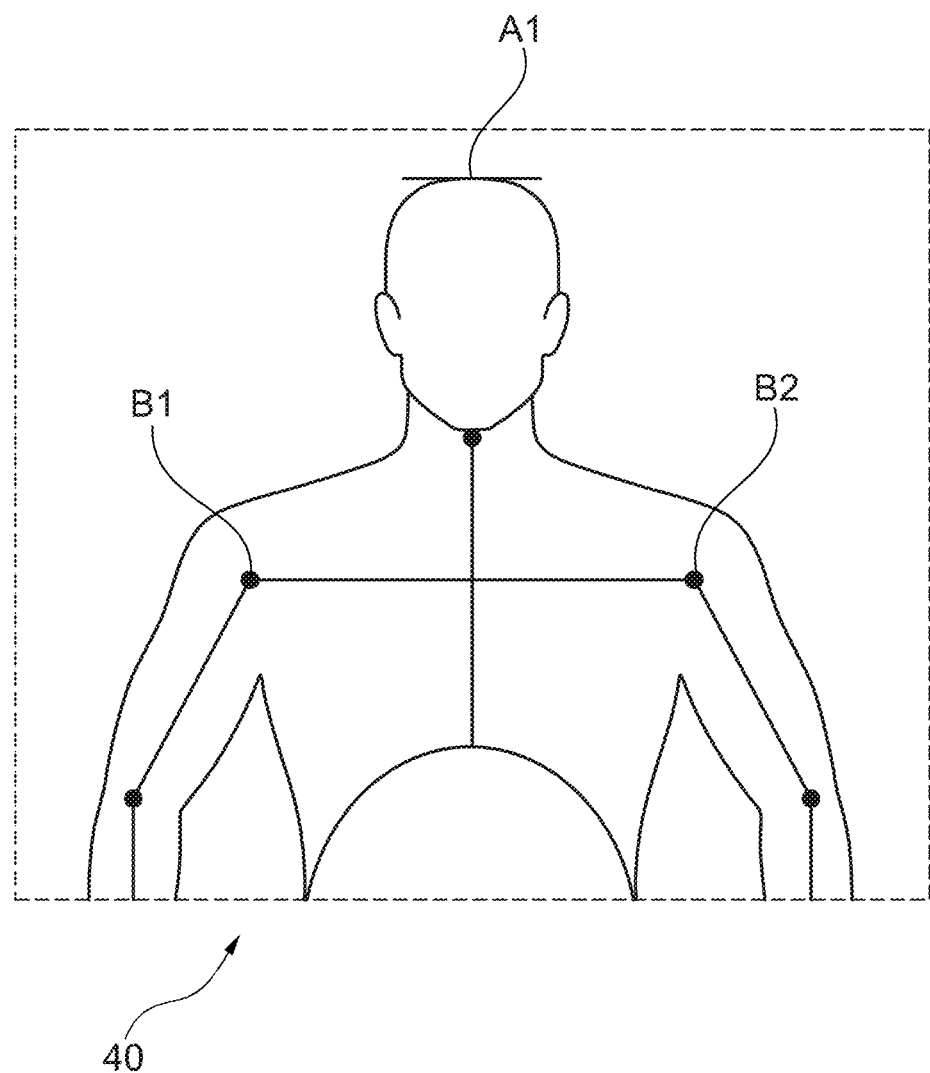
FIG. 3 shows a perspective of a camera on a user using a training machine assembly.

FIG. 3 shows image data 40 corresponding to a camera 20 associated with a training machine assembly 10.

The system can be configured for generating skeleton trajectory data based on the image data. As can be seen in FIG. 3, the system can for example be configured for determining a vertical position A1 of the upper end of the head of the user. The system is can further be configured for determining the positions B1 and B2 relating to a left and right upper arm or shoulder of the user.

The system is configured for comparing the skeleton trajectory data to skeleton reference data. The system can thus for example identify improper exercising of the user.

The system uses boundary conditions for generating the skeleton trajectory data, which boundary conditions relate to the position of the user. When the user sits on the training machine assembly 10, then his/her chest, arms and head are visible. Also, the user faces the camera 20. Hence, an orientation of the user relative to the training machine assembly is known. One boundary condition can for example relate to the orientation of the user. Another boundary condition can relate to an expected position of the chest of the user.

These boundary conditions can for example lead to a reduced need of computing power. They can also lead to an improved reliability of the generated data.

The system can further be configured for generating the heart-rate data of the user based on the image data 40, as discussed above. The system can then be configured for also using boundary conditions. A boundary condition can for example be a limitation of where the head of the user can be located while the user sits on the machine.

Figure 4:
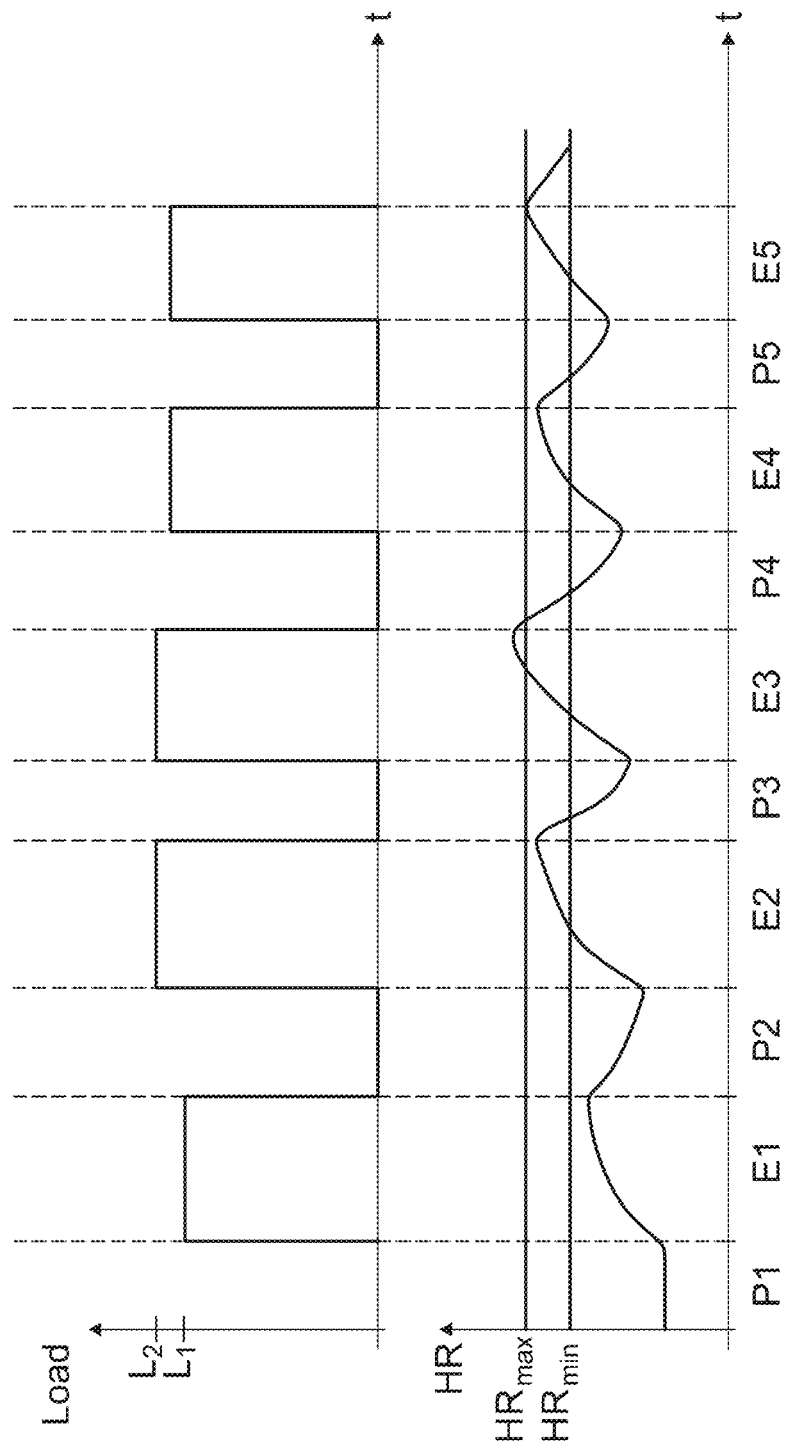
FIG. 4 shows a heart-rate as well as training resistances of a user training in a circuit setup.

FIG. 4 shows the heart-rate of the user training in a circuit setup on the lower half of the figure (indicated by "HR"/$HR_{max}$/$HR_{min}$) and a measure for the training resistance value of the training resistance associated with a respective user exercise on the upper half (indicated by "Load"/L1/L2). The training resistance value is indicated relative to a standard training resistance value corresponding to the exercise and the user.

In FIG. 4, the circuit training comprises five exercises. Obviously, the training could also comprise less or more exercises.

At the beginning of an exercise, the heart-rate of the user typically rises. For an optimal training effect, the heart rate of the user should be between $HR_{min}$ and $HR_{max}$ at the end of each exercise.

As can be seen, the heart-rate of the user is below $HR_{min}$ at the end of the first exercise E1. In such a case, the system is configured to increase the training resistance value. This can for example be performed during an exercise. It can also be performed at a next exercise, as can be seen in FIG. 4: The system increases the training resistance of the second exercise E2 with respect to the normal user-specific training resistance corresponding to E2. As can be seen, the heart-rate of the user increases during the second exercise so that it is between $HR_{max}$ and $HR_{min}$ at the end of the second exercise.

As regards the training resistance value, the system applies the same setting also to the third exercise E3. In other words, the training value is increase to a similar or same degree as it was for E2. However, the heart-rate of the user exceeds the range of $HR_{min}$ and $HR_{max}$ at the end of E3. The system reacts by reducing the training resistance value for E4 and E5.

The system can also be configured to determine the level to which the heart-rate of the user drops in between the exercises, as well as a steepness of the heart-rate of the user. These can all be measures for a fitness and/or the exhaustion of the user.

Whenever a relative term, such as "about", "substantially" or "approximately" is used in this specification, such a term should also be construed to also include the exact term. That is, e.g., "substantially straight" should be construed to also include "(exactly) straight".

Whenever steps were recited in the above or also in the appended claims, it should be noted that the order in which the steps are recited in this text may be accidental. That is, unless otherwise specified or unless clear to the skilled person, the order in which steps are recited may be accidental. That is, when the present document states, e.g., that a method comprises steps (A) and (B), this does not necessarily mean that step (A) precedes step (B), but it is also possible that step (A) is performed (at least partly) simultaneously with step (B) or that step (B) precedes step (A). Furthermore, when a step (X) is said to precede another step (Z), this does not imply that there is no step between steps (X) and (Z). That is, step (X) preceding step (Z) encompasses the situation that step (X) is performed directly before step (Z), but also the situation that (X) is performed before one or more steps (Y1), . . . , followed by step (Z). Corresponding considerations apply when terms like "after" or "before" are used.

While in the above, a preferred embodiment has been described with reference to the accompanying drawings, the skilled person will understand that this embodiment was provided for illustrative purpose only and should by no means be construed to limit the scope of the present invention, which is defined by the claims.

I claim:

1. A training machine assembly, comprising:
   (i) at least one control device, and
   (ii) at least one training resistance,
   wherein each training resistance comprises at least one training resistance value, and
   wherein the at least one training resistance is automatically adjustable, and the training machine assembly is configured to adjust the at least one training resistance, and
   wherein the training machine assembly is configured to
   (a) generate skeleton data of a user based on image data of the user captured by at least one camera, wherein the skeleton data comprise data relating to one or more anatomical features of the user, said one or more anatomical features including one or more of: joint positions, distances of joints, length of body parts, and asymmetries;
   (b) compare the skeleton data to skeleton-reference data; and to
   (c) thus generate skeleton-comparison data.

2. The training machine assembly according to claim 1, wherein the training machine assembly is configured for adjusting at least one of the at least one training resistance based on the skeleton-comparison data.

3. The training machine assembly according to claim 2, comprising at least one automatically adjustable user support element, the user support element configured to stay fixed during an exercise by the user.

4. The training machine assembly according to claim 3, wherein the training machine assembly is configured to
   (d) generate skeleton-trajectory data of a user based on image data of the user captured by the at least one camera; and
   (e) compare the skeleton-trajectory data to skeleton-reference data and to thus generate trajectory-comparison data.

5. The training machine assembly according to claim 4, wherein the training machine assembly is configured to adjust at least one of the at least one automatically adjustable user support element based on at least one of the skeleton-comparison data and the trajectory-comparison data.

6. The training machine assembly according to claim 1, wherein the training machine assembly is configured to receive the skeleton-comparison data from at least one or a plurality of further training machine assemblies.

7. The training machine assembly according to claim 1, wherein the training machine assembly is configured for user identification by facial recognition.

8. A system comprising:
   (a) a plurality of training machine assemblies, each comprising at least one or more training resistances, wherein each training resistance comprises at least one training resistance value;
   (b) a communication network that is configured to enable data transmission between a plurality of the training machine assemblies of the system; and
   (c) a data processing system; and
   (d) at least one camera,
   wherein the system is configured to adjust at least one of the one or more training resistances, and
   wherein the system is configured to
   (A) generate skeleton data of a user based on image data of the user captured by at least one camera, wherein the skeleton data comprise data relating to one or more anatomical features of the user, said one or more anatomical features including one or more of: joint positions, distances of joints, length of body parts, and asymmetries;
   (B) compare the skeleton data to skeleton-reference data; and to
   (C) thus generate skeleton-comparison data.

9. The system according to claim 8, wherein the system is configured to use at least one boundary condition corresponding to geometries of the respective training machine assemblies, wherein said at least one boundary condition is used for the generation of said skeleton data.

10. The system according to claim 9, wherein
    (e) at least one training machine assembly of the system comprises at least one automatically adjustable user support element; and
    (f) the system is configured to automatically adjust at least one automatically adjustable user support element based on comparison data; and
    (g) the comparison data comprise at least a portion of the skeleton-comparison data.

11. The system according to claim 8, wherein
    (h) the system is configured to process user plan data; and
    (i) the user plan data comprise data relating to a training resistance for at least one exercise; and
    (j) the system is configured to adjust at least one of the training resistances based on at least a portion of the user plan data.

12. The system according to claim 11, wherein the system is configured to adapt the user plan data.

13. The system according to claim 8,
wherein the system is configured to generate heart rate data of the user based on image data captured by the at least one camera, and
wherein the system is configured to adjust at least one of the training resistances based on the heart rate data.

14. A method comprising:
(a) using a plurality of training machine assemblies;
(b) providing a plurality of training resistances to at least one user, each training resistance comprising a training resistance value;
(c) automatically adjusting the plurality of training resistances;
(d) transmitting data between the training machine assemblies; and
(e) using a data processing system,
(f) sensing image data of the at least one user using at least one camera, and
(g) generating skeleton data of the at least one user based on image data of the at least one user captured by at least one camera, wherein the skeleton data comprise data relating to one or more anatomical features of the at least one user, said one or more anatomical features including one or more of: joint positions, distances of joints, length of body parts, and asymmetries;
(h) comparing the skeleton data to skeleton-reference data; and
(i) generating skeleton-comparison data.

15. The method according to claim 14, wherein the method comprises adjusting at least one training resistance based on the skeleton-comparison data.

16. The method according to claim 14, wherein the method further comprises:
(j) generating the skeleton data of the user based on image data of the user captured by at least one of at least one camera; and wherein
(k) said generating the skeleton data in (j) uses boundary conditions corresponding to geometries of the respective training machine assemblies.

17. The method according to claim 14, wherein the method further comprises:
(j) automatically adjusting at least one user support element based on comparison data; and
(k) comparing the skeleton data to skeleton-reference data and thus generating skeleton-comparison data, wherein the comparison data comprise at least a portion of the skeleton-comparison data.

18. The method according to claim 14, wherein
(j) the method comprises processing user plan data;
(k) the user plan data comprise data relating to a training resistance for at least one user exercise; and
(l) the method comprises adjusting at least one of the training resistances based on at least a portion of the user plan data.

19. The method according to claim 14, wherein the method comprises adjusting the plurality of training resistances based on the user's heart rate.

* * * * *